(12) United States Patent
Lee et al.

(10) Patent No.: US 7,699,835 B2
(45) Date of Patent: Apr. 20, 2010

(54) ROBOTICALLY CONTROLLED SURGICAL INSTRUMENTS

(75) Inventors: Woojin Lee, Hopkinton, MA (US); Andres Chamorro, III, Arlington, MA (US); Robert Ailinger, Norwood, MA (US); Dwight Meglan, Westwood, MA (US)

(73) Assignee: Hansen Medical, Inc., Mountain View, CA (US)

( * ) Notice: Subject to any disclaimer, the term of this patent is extended or adjusted under 35 U.S.C. 154(b) by 1728 days.

(21) Appl. No.: 10/715,339

(22) Filed: Nov. 17, 2003

(65) Prior Publication Data

US 2004/0193146 A1    Sep. 30, 2004

Related U.S. Application Data

(63) Continuation-in-part of application No. 10/014,143, filed on Nov. 16, 2001, now abandoned, and a continuation-in-part of application No. 10/008,964, filed on Nov. 16, 2001, now abandoned, and a continuation-in-part of application No. 10/013,046, filed on Nov. 16, 2001, now abandoned, and a continuation-in-part of application No. 10/011,450, filed on Nov. 16, 2001, now abandoned, and a continuation-in-part of application No. 10/008,457, filed on Nov. 16, 2001, now Pat. No. 6,949,106, and a continuation-in-part of application No. 10/008,871, filed on Nov. 16, 2001, now Pat. No. 6,843,793, and a continuation-in-part of application No. 10/012,845, filed on Nov. 16, 2001, and a continuation-in-part of application No. 10/023,024, filed on Nov. 16, 2001, now abandoned, and a continuation-in-part of application No. 10/011,371, filed on Nov. 16, 2001, now Pat. No. 7,090,683, and a continuation-in-part of application No. 10/011,449, filed on Nov. 16, 2001, now abandoned, and a continuation-in-part of application No. 10/010,150, filed on Nov. 16, 2001, and a continuation-in-part of application No. 10/022,038, filed on Nov. 16, 2001, now abandoned, and a continuation-in-part of application No. 10/012,586, filed on Nov. 16, 2001.

(60) Provisional application No. 60/427,525, filed on Nov. 18, 2002, provisional application No. 60/493,425, filed on Aug. 7, 2003, provisional application No. 60/279,087, filed on Mar. 27, 2001, provisional application No. 60/269,200, filed on Feb. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/293,346, filed on May 24, 2001.

(51) Int. Cl.
*A61B 17/00* (2006.01)

(52) U.S. Cl. .......................... 606/1; 606/130; 606/205

(58) Field of Classification Search ................ 606/1, 606/130, 205, 206, 207, 208, 147, 148; 600/109, 600/118, 114, 37

See application file for complete search history.

(56) References Cited

U.S. PATENT DOCUMENTS 2,709,570 A * 5/1955 Henry .......................... 254/18

(Continued)

FOREIGN PATENT DOCUMENTS

EP        0683016       5/1995

(Continued)

OTHER PUBLICATIONS

Ikuta, et al., "Shape Memory Alloy Servo Actuator System with Electric Resistance Feedback and Application for Active Endoscope", 1988 IEEE, CH2555-1/88/000/0427-430 (16 Pages).

(Continued)

*Primary Examiner*—Pedro Philogene
(74) *Attorney, Agent, or Firm*—Vista IP Law Group, LLP

(57) ABSTRACT

A robotically controlled surgical instrument includes a first jaw and a second jaw used to grasp an item, and a drive mechanism that increases the force applied to the item grasped. The drive mechanism and the jaws can be provided with an accommodating mechanism that allows continued movement of the drive mechanism towards a locked position even after the jaws contact a larger item so that the drive mechanism can move to the locked position when grasping items of different sizes.

29 Claims, 34 Drawing Sheets

U.S. PATENT DOCUMENTS

| | | | |
|---|---|---|---|
| 2,765,930 A | 10/1956 | Greer et al. | |
| 3,111,230 A | 11/1963 | Presenti | |
| 3,190,286 A | 6/1965 | Stokes | |
| 3,266,059 A | 8/1966 | Stelle | |
| 3,414,137 A | 12/1968 | Fortin | |
| 3,497,083 A | 2/1970 | Anderson et al. | |
| 3,659,890 A | 5/1972 | Renfroe | |
| 3,759,563 A | 9/1973 | Kitamura | |
| 3,782,666 A | 1/1974 | Sandrone et al. | |
| 4,078,766 A * | 3/1978 | Saurwein | 254/18 |
| 4,495,423 A | 1/1985 | Rogers | |
| 4,604,016 A | 8/1986 | Joyce | |
| 4,654,024 A | 3/1987 | Crittenden et al. | |
| 4,702,250 A | 10/1987 | Ovil et al. | |
| 4,750,475 A | 6/1988 | Yoshihashi | |
| 4,853,874 A | 8/1989 | Iwamoto et al. | |
| 4,887,612 A * | 12/1989 | Esser et al. | 600/564 |
| 4,941,454 A | 7/1990 | Wood et al. | |
| 4,977,886 A | 12/1990 | Takehana et al. | |
| 4,979,949 A | 12/1990 | Matsen, III et al. | |
| 5,052,402 A | 10/1991 | Bencini et al. | |
| 5,072,361 A | 12/1991 | Davis et al. | |
| 5,078,140 A | 1/1992 | Kwoh | |
| 5,084,054 A | 1/1992 | Bencini et al. | |
| 5,085,401 A | 2/1992 | Glassman et al. | |
| 5,116,180 A | 5/1992 | Fung et al. | |
| 5,154,717 A | 10/1992 | Matsen, III et al. | |
| 5,171,258 A | 12/1992 | Bales et al. | |
| 5,172,700 A | 12/1992 | Bencini et al. | |
| 5,174,278 A | 12/1992 | Babkow | |
| 5,174,300 A | 12/1992 | Bales et al. | |
| 5,184,601 A | 2/1993 | Putman | |
| 5,209,747 A | 5/1993 | Knoepfler | |
| 5,217,003 A | 6/1993 | Wilk | |
| 5,236,432 A | 8/1993 | Matsen, III et al. | |
| 5,238,002 A | 8/1993 | Devlin et al. | |
| 5,238,005 A | 8/1993 | Imran | |
| 5,254,130 A | 10/1993 | Poncet et al. | |
| 5,271,381 A | 12/1993 | Ailenger et al. | |
| 5,287,861 A | 2/1994 | Wilk | |
| 5,295,958 A | 3/1994 | Shturman | |
| 5,299,288 A | 3/1994 | Glassman et al. | |
| 5,339,799 A | 8/1994 | Kami et al. | |
| 5,347,987 A | 9/1994 | Feldstein et al. | |
| 5,350,355 A | 9/1994 | Sklar | |
| 5,354,311 A | 10/1994 | Kambin et al. | |
| 5,368,015 A | 11/1994 | Wilk | |
| 5,372,147 A | 12/1994 | Lathrop, Jr. et al. | |
| 5,382,685 A | 1/1995 | Klein et al. | |
| 5,382,885 A | 1/1995 | Salcudean et al. | |
| 5,389,100 A | 2/1995 | Bacich et al. | |
| 5,395,367 A | 3/1995 | Wilk | |
| 5,397,323 A | 3/1995 | Taylor et al. | |
| 5,398,691 A | 3/1995 | Martin | |
| 5,402,801 A | 4/1995 | Taylor | |
| 5,409,019 A | 4/1995 | Wilk | |
| 5,410,638 A | 4/1995 | Colgate et al. | |
| 5,417,210 A | 5/1995 | Funda et al. | |
| 5,429,144 A | 7/1995 | Wilk | |
| 5,431,675 A | 7/1995 | Nicholas et al. | |
| 5,447,149 A | 9/1995 | Kikawada et al. | |
| 5,467,763 A | 11/1995 | McMahon et al. | |
| 5,477,856 A | 12/1995 | Lundquist | |
| 5,478,347 A | 12/1995 | Aranyi | |
| 5,478,351 A | 12/1995 | Meade et al. | |
| 5,480,422 A | 1/1996 | Ben-Haim | |
| 5,497,784 A | 3/1996 | Imran | |
| 5,499,998 A * | 3/1996 | Meade | 606/207 |
| 5,515,478 A | 5/1996 | Wang | |
| 5,520,644 A | 5/1996 | Imran | |
| 5,524,180 A | 6/1996 | Wang et al. | |
| 5,540,649 A | 7/1996 | Bonnell et al. | |
| 5,553,198 A | 9/1996 | Wang et al. | |
| 5,572,999 A | 11/1996 | Funda et al. | |
| 5,606,979 A | 3/1997 | Hodgson | |
| 5,607,450 A | 3/1997 | Zvenyatsky et al. | |
| 5,618,294 A | 4/1997 | Aust et al. | |
| 5,620,415 A | 4/1997 | Lucey et al. | |
| 5,624,398 A | 4/1997 | Smith et al. | |
| 5,626,553 A | 5/1997 | Frassica et al. | |
| 5,626,595 A | 5/1997 | Sklar et al. | |
| 5,631,973 A | 5/1997 | Green | |
| 5,632,758 A | 5/1997 | Sklar | |
| 5,634,897 A | 6/1997 | Dance et al. | |
| 5,636,634 A | 6/1997 | Kordis et al. | |
| 5,643,294 A | 7/1997 | Tovey et al. | |
| 5,649,956 A | 7/1997 | Jensen et al. | |
| 5,657,429 A | 8/1997 | Wang et al. | |
| 5,667,476 A | 9/1997 | Frassica et al. | |
| 5,674,279 A | 10/1997 | Wright et al. | |
| 5,713,946 A | 2/1998 | Ben-Haim | |
| 5,738,096 A | 4/1998 | Ben-Haim | |
| 5,746,759 A | 5/1998 | Meade et al. | |
| 5,752,973 A * | 5/1998 | Kieturakis | 606/207 |
| 5,754,741 A | 5/1998 | Wang et al. | |
| 5,759,153 A | 6/1998 | Webler et al. | |
| 5,762,458 A | 6/1998 | Wang et al. | |
| 5,766,196 A | 6/1998 | Griffiths | |
| 5,784,542 A | 7/1998 | Ohm et al. | |
| 5,792,135 A | 8/1998 | Madhani et al. | |
| 5,800,333 A | 9/1998 | Liprie | |
| 5,800,423 A | 9/1998 | Jensen | |
| 5,807,377 A | 9/1998 | Madhani et al. | |
| 5,808,665 A | 9/1998 | Green | |
| 5,810,880 A | 9/1998 | Jensen et al. | |
| 5,814,038 A | 9/1998 | Jensen et al. | |
| 5,815,640 A | 9/1998 | Wang et al. | |
| 5,817,119 A * | 10/1998 | Klieman et al. | 606/174 |
| 5,821,920 A | 10/1998 | Rosenberg et al. | |
| 5,823,993 A | 10/1998 | Lemelson | |
| 5,825,982 A | 10/1998 | Wright et al. | |
| 5,826,467 A | 10/1998 | Huang | |
| 5,827,313 A | 10/1998 | Ream | |
| 5,828,197 A | 10/1998 | Martin et al. | |
| 5,833,608 A | 11/1998 | Acker | |
| 5,833,656 A | 11/1998 | Smith et al. | |
| 5,833,658 A | 11/1998 | Levy et al. | |
| 5,843,076 A | 12/1998 | Webster | |
| 5,845,646 A | 12/1998 | Lemelson | |
| 5,855,553 A | 1/1999 | Tajima et al. | |
| 5,855,583 A | 1/1999 | Wang et al. | |
| 5,860,992 A | 1/1999 | Daniel et al. | |
| 5,861,024 A | 1/1999 | Rashidi | |
| 5,868,755 A | 2/1999 | Kanner et al. | |
| 5,876,325 A | 3/1999 | Mizuno et al. | |
| 5,878,193 A | 3/1999 | Wang et al. | |
| 5,907,664 A | 5/1999 | Wang et al. | |
| 5,919,206 A | 7/1999 | Gengler et al. | |
| 5,928,248 A | 7/1999 | Acker | |
| 5,931,832 A | 8/1999 | Jensen | |
| 5,950,629 A | 9/1999 | Taylor | |
| 5,954,692 A | 9/1999 | Smith et al. | |
| 5,954,731 A | 9/1999 | Yoon | |
| 5,957,941 A | 9/1999 | Ream | |
| 5,964,717 A | 10/1999 | Gottlieb et al. | |
| 5,964,780 A | 10/1999 | Balazs | |
| 5,971,976 A | 10/1999 | Wang et al. | |
| 5,976,122 A | 11/1999 | Madhani et al. | |
| 5,977,886 A | 11/1999 | Barile et al. | |
| 6,001,108 A | 12/1999 | Wang et al. | |
| 6,004,332 A | 12/1999 | Yoon et al. | |
| 6,007,550 A | 12/1999 | Wang et al. | |
| 6,007,560 A | 12/1999 | Gottlieb et al. | |
| 6,019,780 A | 2/2000 | Lombardo et al. | |

| | | | |
|---|---|---|---|
| 6,024,695 A | 2/2000 | Taylor et al. |
| 6,036,636 A | 3/2000 | Motoki et al. |
| 6,042,166 A | 3/2000 | Conte |
| 6,058,323 A | 5/2000 | Lemelson |
| 6,063,095 A | 5/2000 | Wang et al. |
| 6,066,102 A | 5/2000 | Townsend et al. |
| 6,080,170 A | 6/2000 | Nash et al. |
| 6,080,181 A | 6/2000 | Jensen et al. |
| 6,083,170 A | 7/2000 | Ben-Haim |
| 6,096,004 A | 8/2000 | Meglan et al. |
| 6,102,850 A | 8/2000 | Wang et al. |
| 6,102,920 A | 8/2000 | Sullivan et al. |
| 6,106,511 A | 8/2000 | Jensen |
| 6,120,433 A | 9/2000 | Mizuno et al. |
| 6,126,635 A | 10/2000 | Simpson et al. |
| 6,132,368 A | 10/2000 | Cooper |
| 6,132,441 A | 10/2000 | Grace |
| 6,143,005 A | 11/2000 | Yoon et al. |
| 6,156,005 A | 12/2000 | Theron |
| 6,165,184 A | 12/2000 | Verdura et al. |
| 6,171,234 B1 | 1/2001 | White et al. |
| 6,179,856 B1 | 1/2001 | Barbere |
| 6,197,017 B1 | 3/2001 | Brock et al. |
| 6,206,903 B1 | 3/2001 | Ramans |
| 6,214,028 B1 | 4/2001 | Yoon et al. |
| 6,221,070 B1 | 4/2001 | Tu et al. |
| 6,223,100 B1 | 4/2001 | Green |
| 6,231,565 B1 | 5/2001 | Tovey et al. |
| 6,233,474 B1 | 5/2001 | Lemelson |
| 6,233,476 B1 | 5/2001 | Strommer |
| 6,233,504 B1 | 5/2001 | Das et al. |
| 6,236,432 B1 | 5/2001 | Lee |
| 6,244,644 B1 | 6/2001 | Lovchik et al. |
| 6,246,200 B1 | 6/2001 | Blumenkranz et al. |
| 6,266,551 B1 | 7/2001 | Osadchy |
| 6,267,781 B1 | 7/2001 | Tu |
| 6,269,819 B1 | 8/2001 | Oz et al. |
| 6,270,508 B1 * | 8/2001 | Klieman et al. ............ 606/147 |
| 6,272,371 B1 | 8/2001 | Shlomo |
| 6,283,921 B1 | 9/2001 | Nix et al. |
| 6,290,675 B1 | 9/2001 | Vujanic et al. |
| 6,292,681 B1 | 9/2001 | Moore |
| 6,309,397 B1 | 10/2001 | Julian et al. |
| 6,312,435 B1 | 11/2001 | Wallace et al. |
| 6,319,227 B1 | 11/2001 | Mansouri-Ruiz |
| 6,325,808 B1 | 12/2001 | Bernard et al. |
| 6,331,181 B1 | 12/2001 | Tierney et al. |
| 6,332,889 B1 | 12/2001 | Sancoff et al. |
| 6,346,072 B1 | 2/2002 | Cooper |
| 6,352,503 B1 | 3/2002 | Matsui et al. |
| 6,358,268 B1 | 3/2002 | Hunt et al. |
| 6,364,888 B1 | 4/2002 | Niemeyer et al. |
| 6,369,834 B1 | 4/2002 | Zilles et al. |
| 6,370,411 B1 | 4/2002 | Osadchy |
| 6,371,907 B1 | 4/2002 | Hasegawa et al. |
| 6,371,952 B1 | 4/2002 | Madhani |
| 6,375,471 B1 | 4/2002 | Wendlandt et al. |
| 6,377,011 B1 | 4/2002 | Ben-Ur |
| 6,385,509 B2 | 5/2002 | Das et al. |
| 6,394,998 B1 | 5/2002 | Wallace et al. |
| 6,397,323 B1 | 5/2002 | Yoshida |
| 6,398,726 B1 | 6/2002 | Ramans et al. |
| 6,398,755 B1 | 6/2002 | Belef et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,451,027 B1 | 9/2002 | Cooper et al. |
| 6,459,926 B1 | 10/2002 | Nowlin et al. |
| 6,463,361 B1 | 10/2002 | Wang et al. |
| 6,468,265 B1 | 10/2002 | Evans et al. |
| 6,485,489 B2 | 11/2002 | Teirstein et al. |
| 6,490,490 B1 | 12/2002 | Uchikubo et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,496,099 B2 | 12/2002 | Wang et al. |
| 6,517,565 B1 | 2/2003 | Whitman et al. |
| 6,522,906 B1 | 2/2003 | Salisbury, Jr. et al. |
| 6,554,844 B2 | 4/2003 | Lee et al. |
| 6,565,554 B1 | 5/2003 | Niemeyer |
| 6,569,084 B1 | 5/2003 | Mizuno |
| 6,574,355 B2 | 6/2003 | Green |
| 6,587,750 B2 | 7/2003 | Gerbi et al. |
| 6,594,552 B1 | 7/2003 | Nowlin et al. |
| 6,620,173 B2 | 9/2003 | Gerbi et al. |
| 6,626,899 B2 | 9/2003 | Houser |
| 6,645,196 B1 | 11/2003 | Nixon et al. |
| 6,659,939 B2 | 12/2003 | Moll |
| 6,669,687 B1 | 12/2003 | Saadat |
| 6,676,684 B1 | 1/2004 | Morley et al. |
| 6,685,698 B2 | 2/2004 | Morley et al. |
| 6,692,485 B1 | 2/2004 | Brock et al. |
| 6,699,235 B2 | 3/2004 | Wallace et al. |
| 6,702,826 B2 | 3/2004 | Liddicoat et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,972 B2 | 11/2004 | Snow |
| 6,817,974 B2 | 11/2004 | Cooper et al. |
| 6,837,883 B2 | 1/2005 | Moll et al. |
| 6,840,938 B1 * | 1/2005 | Morley et al. ............ 606/51 |
| 6,852,107 B2 | 2/2005 | Wang et al. |
| 6,858,003 B2 | 2/2005 | Evans |
| 6,860,877 B1 | 3/2005 | Sanchez et al. |
| 6,905,460 B2 | 6/2005 | Wang |
| 6,911,916 B1 | 6/2005 | Wang et al. |
| 6,936,001 B1 | 8/2005 | Snow |
| 6,936,056 B2 | 8/2005 | Nash et al. |
| 6,951,535 B2 | 10/2005 | Ghodoussi et al. |
| 6,963,792 B1 | 11/2005 | Green |
| 6,994,708 B2 | 2/2006 | Manzo |
| 7,025,064 B2 | 4/2006 | Wang et al. |
| 7,090,683 B2 | 8/2006 | Brock et al. |
| 7,214,230 B2 | 5/2007 | Brock et al. |
| 7,297,142 B2 | 11/2007 | Brock |
| 7,343,195 B2 | 3/2008 | Strommer |
| 7,371,210 B2 | 5/2008 | Brock |
| 2002/0087151 A1 | 7/2002 | Mody et al. |
| 2003/0135204 A1 | 7/2003 | Lee |

FOREIGN PATENT DOCUMENTS

| | | |
|---|---|---|
| EP | 0776738 | 6/1997 |
| JP | 8-33628 | 6/1996 |
| WO | WO 93/14704 | 8/1993 |
| WO | WO 98/25666 | 6/1998 |
| WO | WO 00/60521 | 10/2000 |
| WO | WO 00/67640 | 11/2000 |
| WO | WO 02/074178 | 9/2002 |

OTHER PUBLICATIONS

M.W. Thring, "Robots and Telechirs: Manipulators with Memory; Remote Manipulators; Machine Limbs for the Handicapped", First published in 1983 by Ellis Horwood Limited (166 Pages).

* cited by examiner

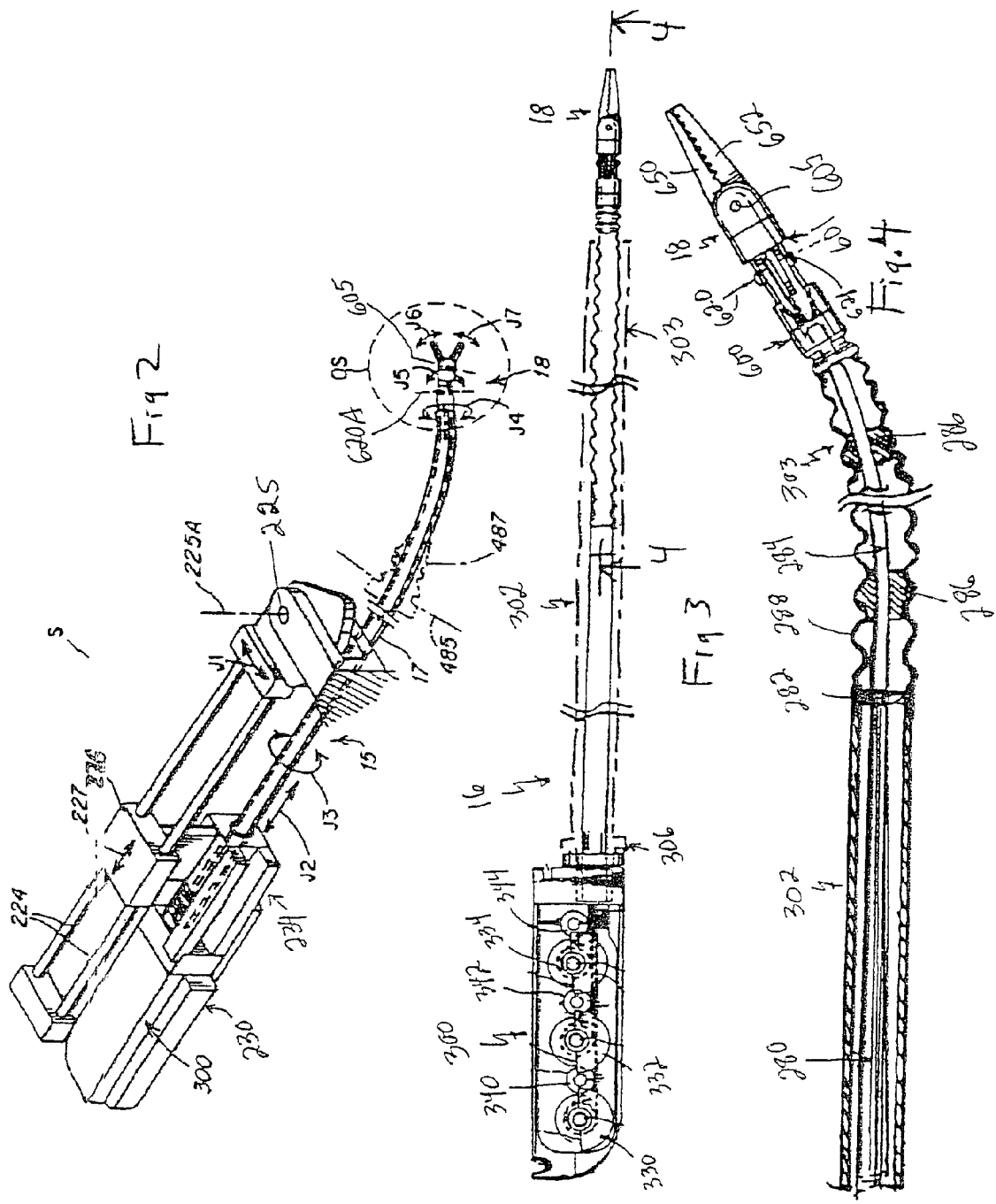

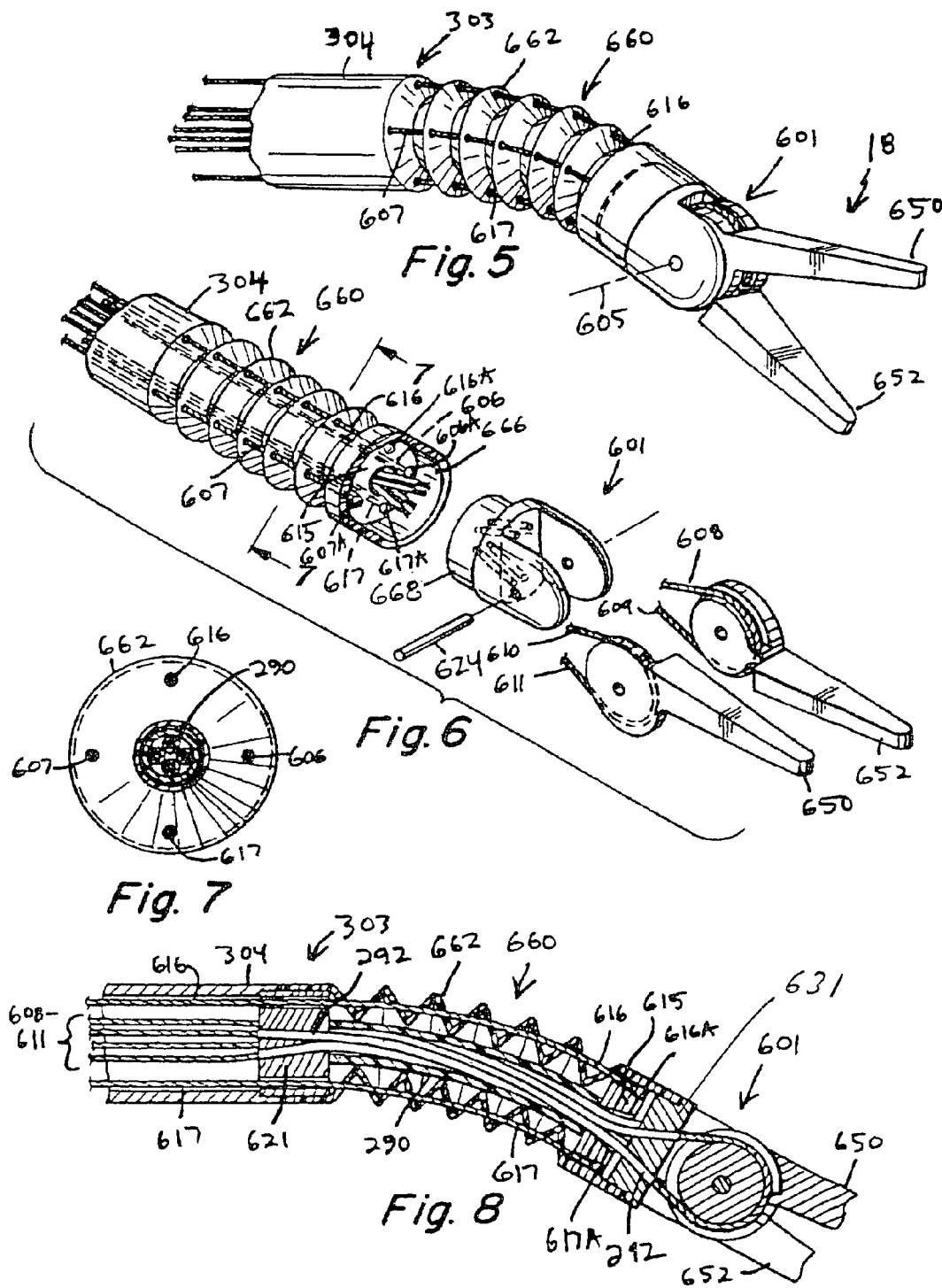

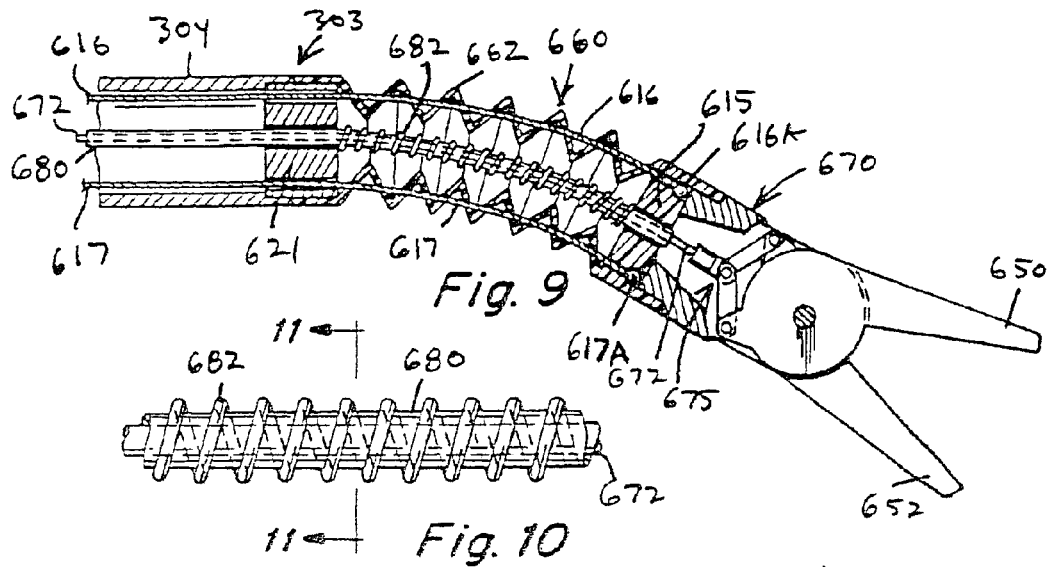
Fig. 9
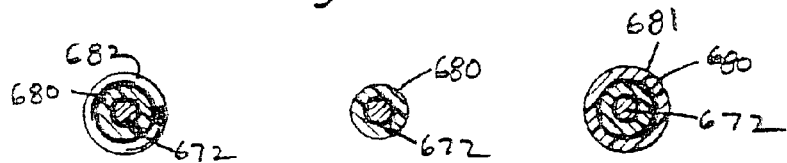
Fig. 10
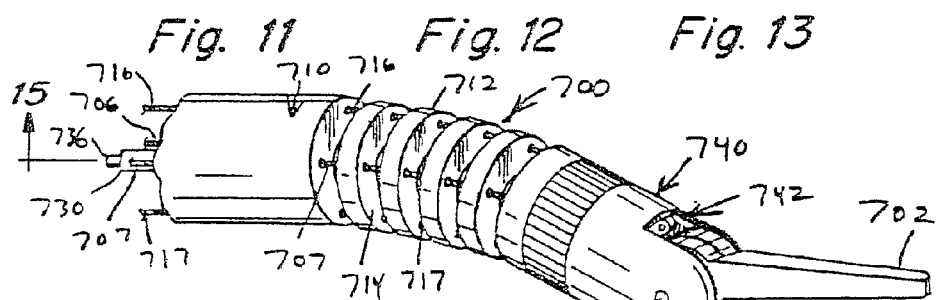
Fig. 11  Fig. 12  Fig. 13
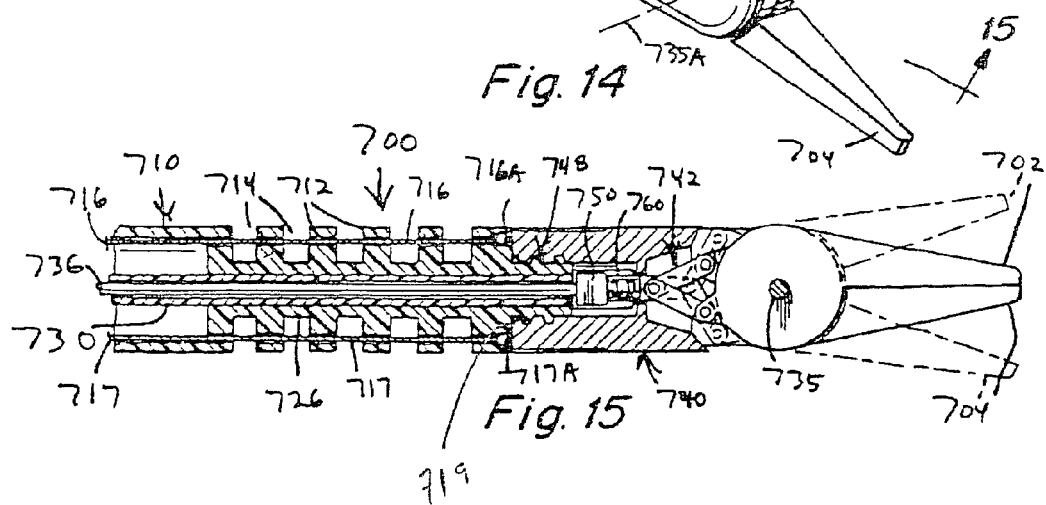
Fig. 14
Fig. 15

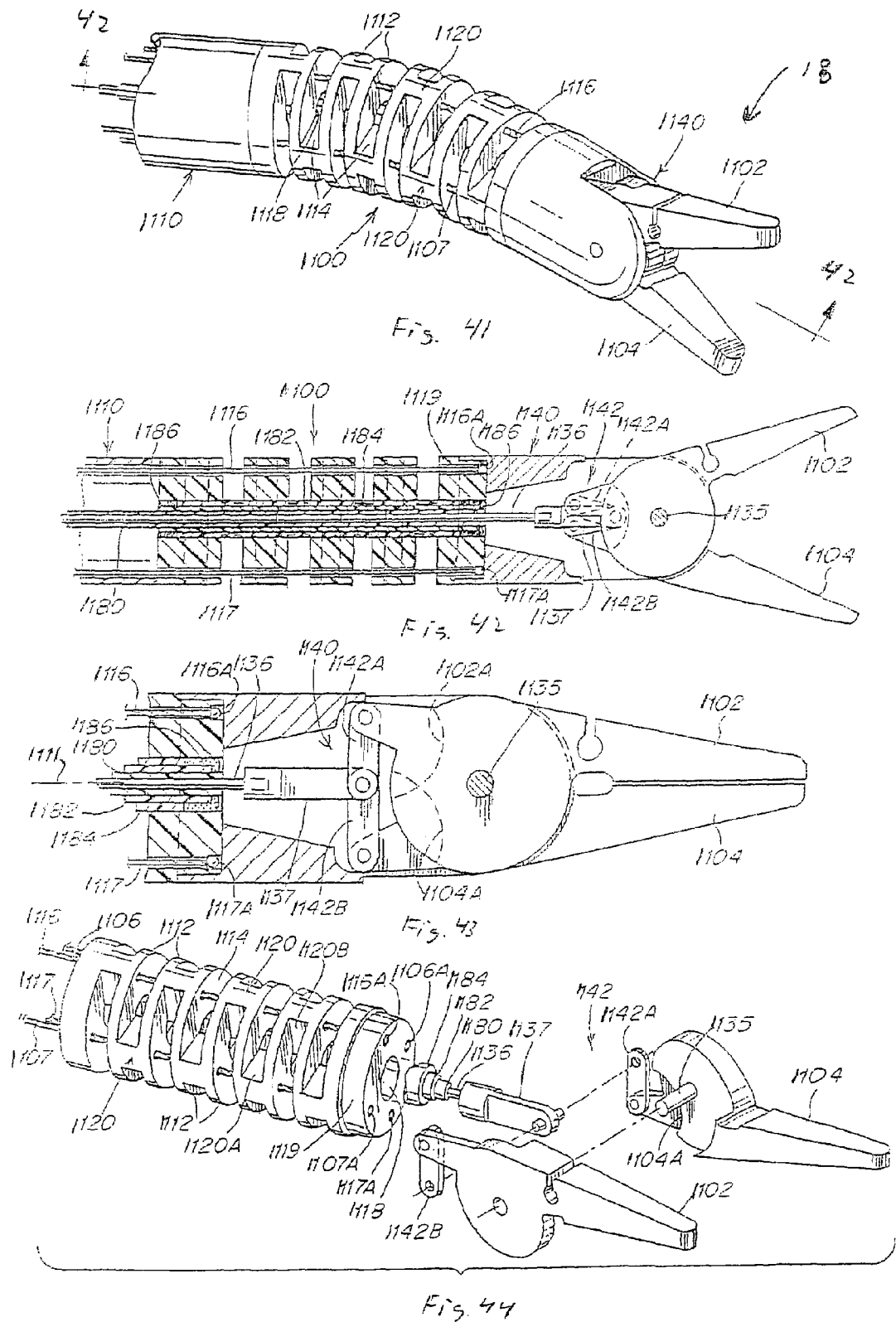

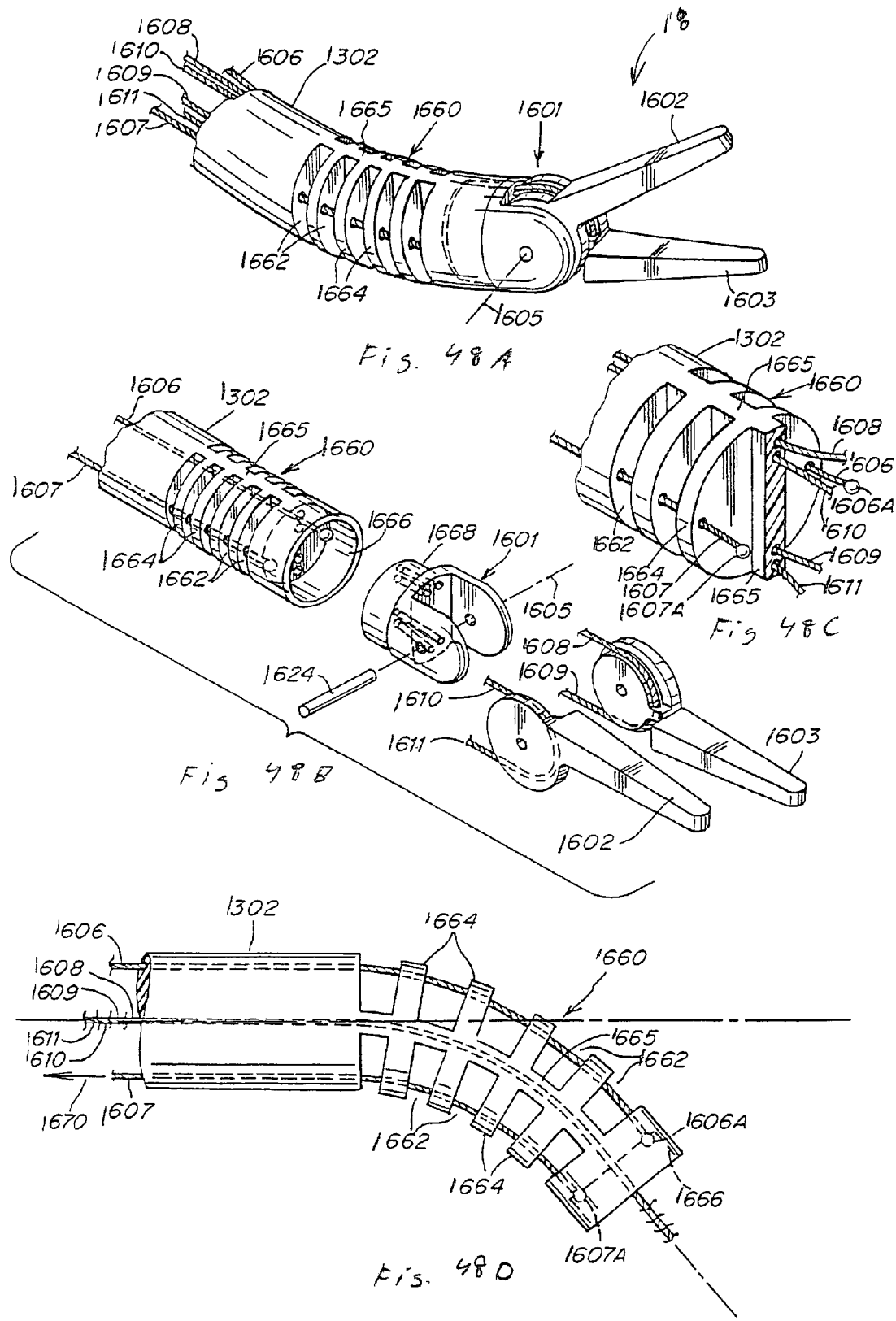

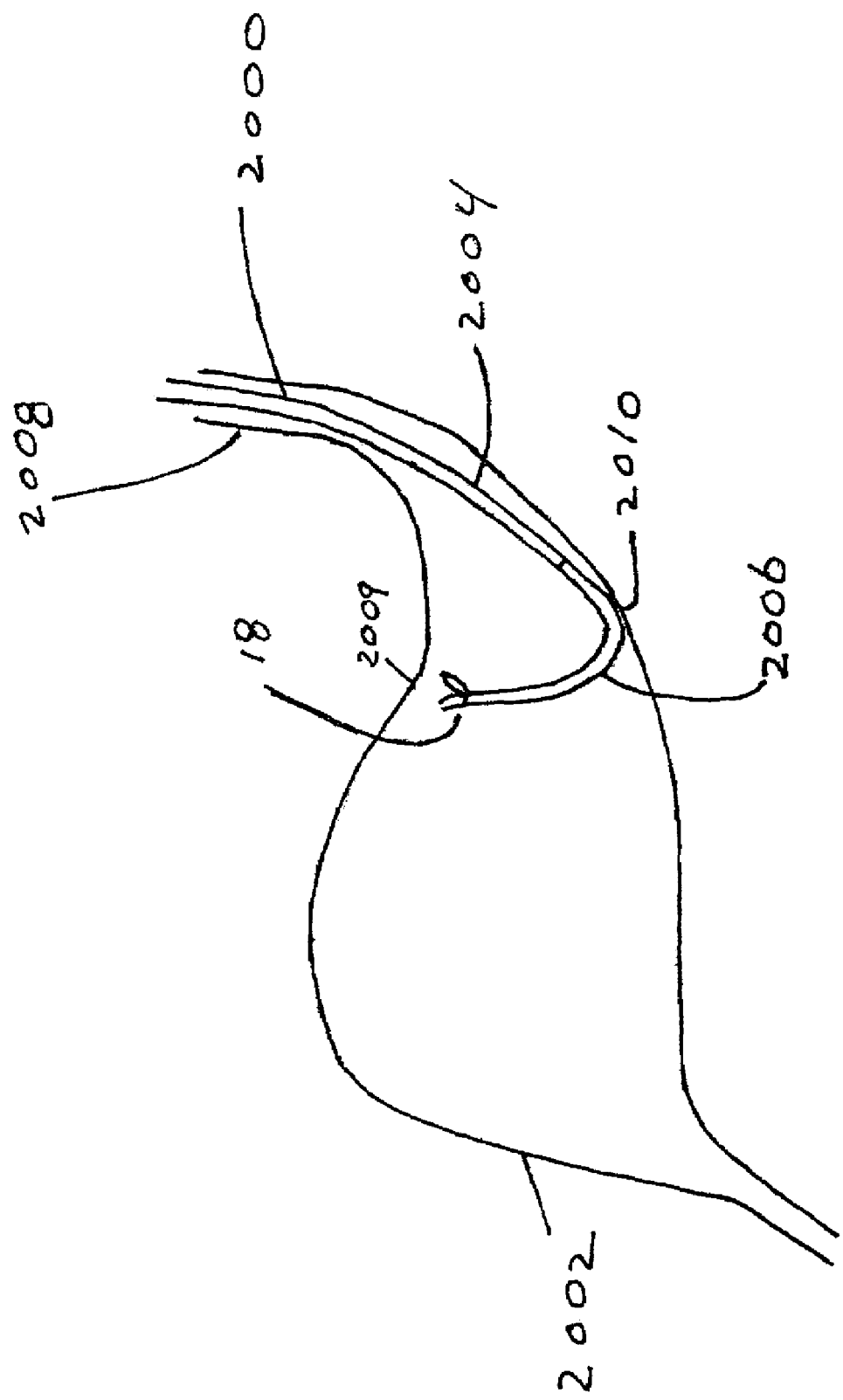

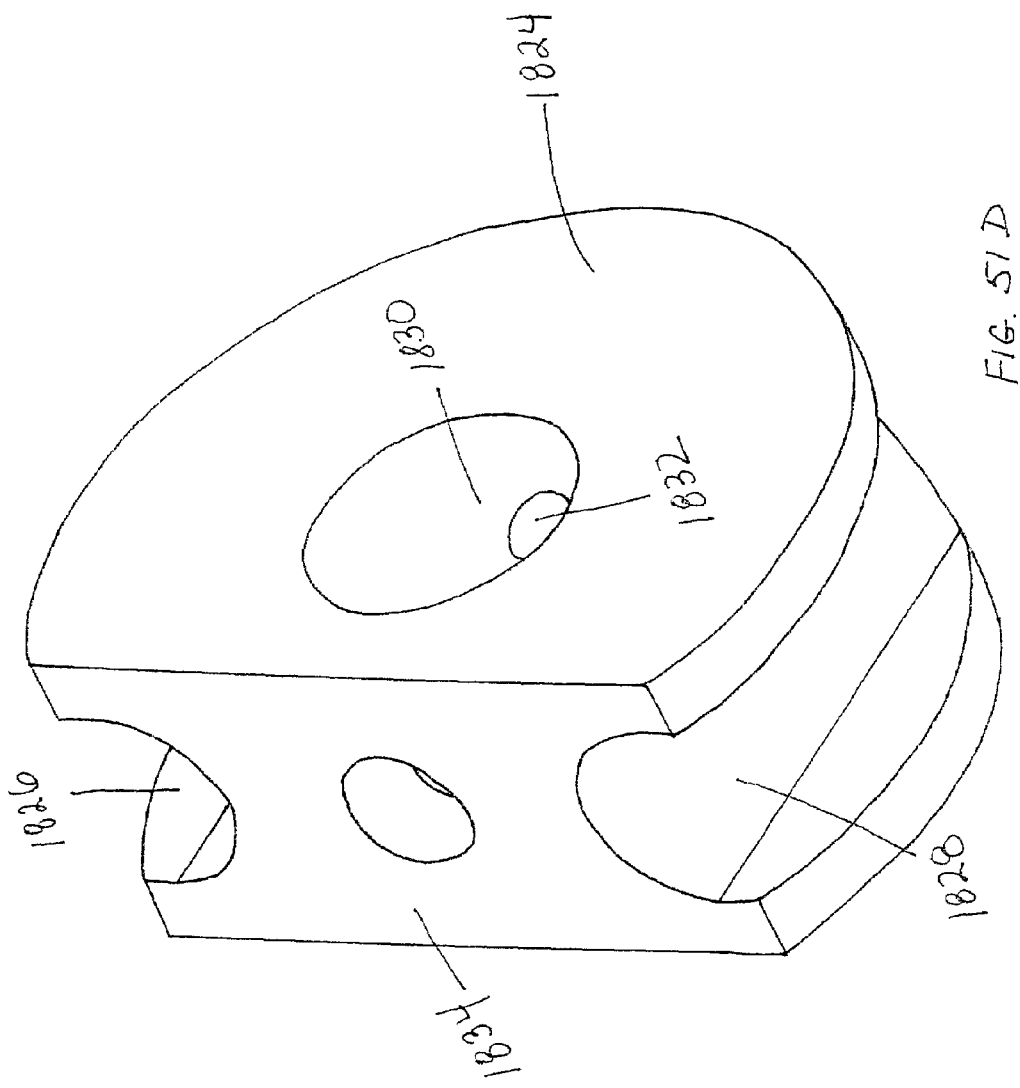

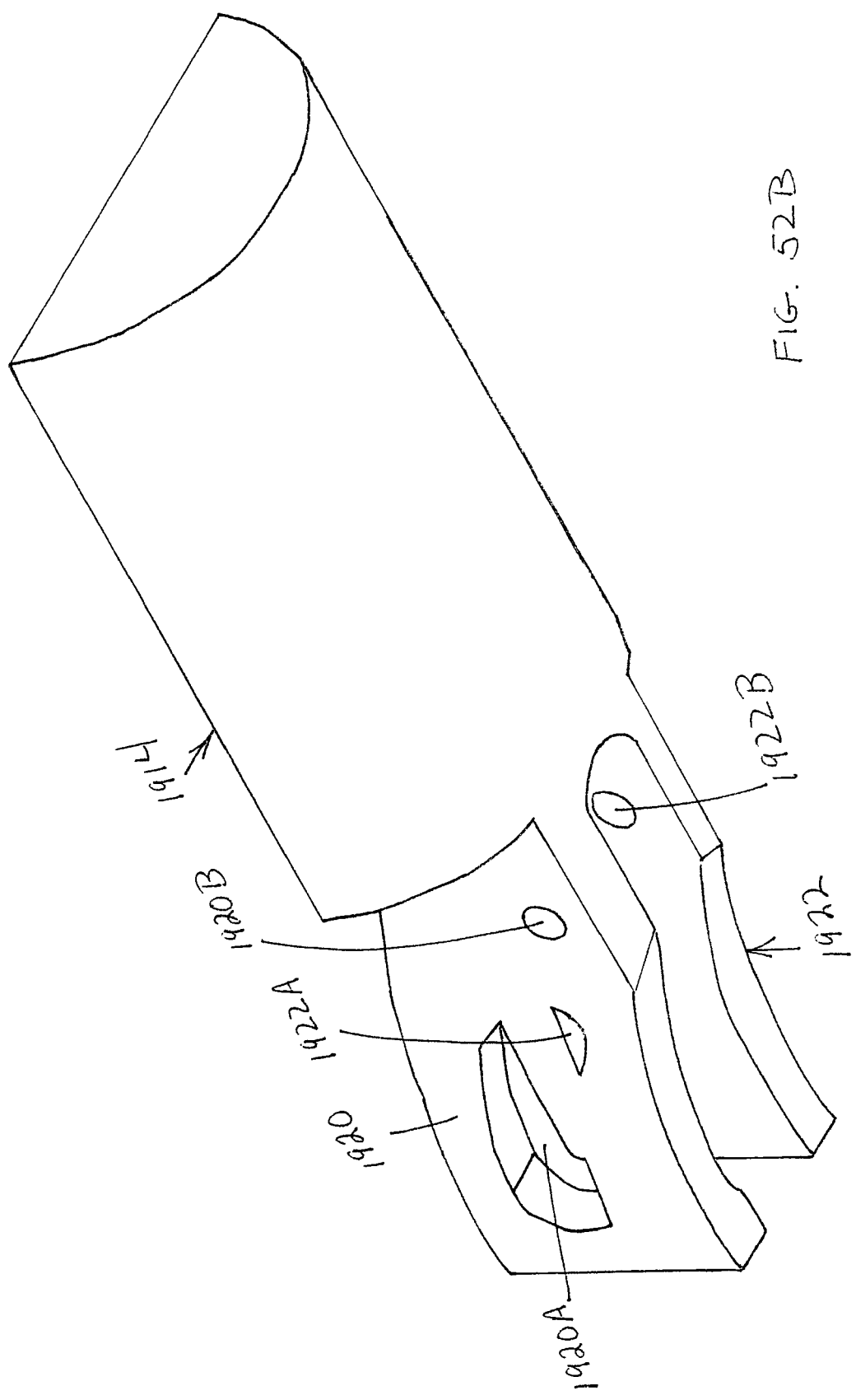

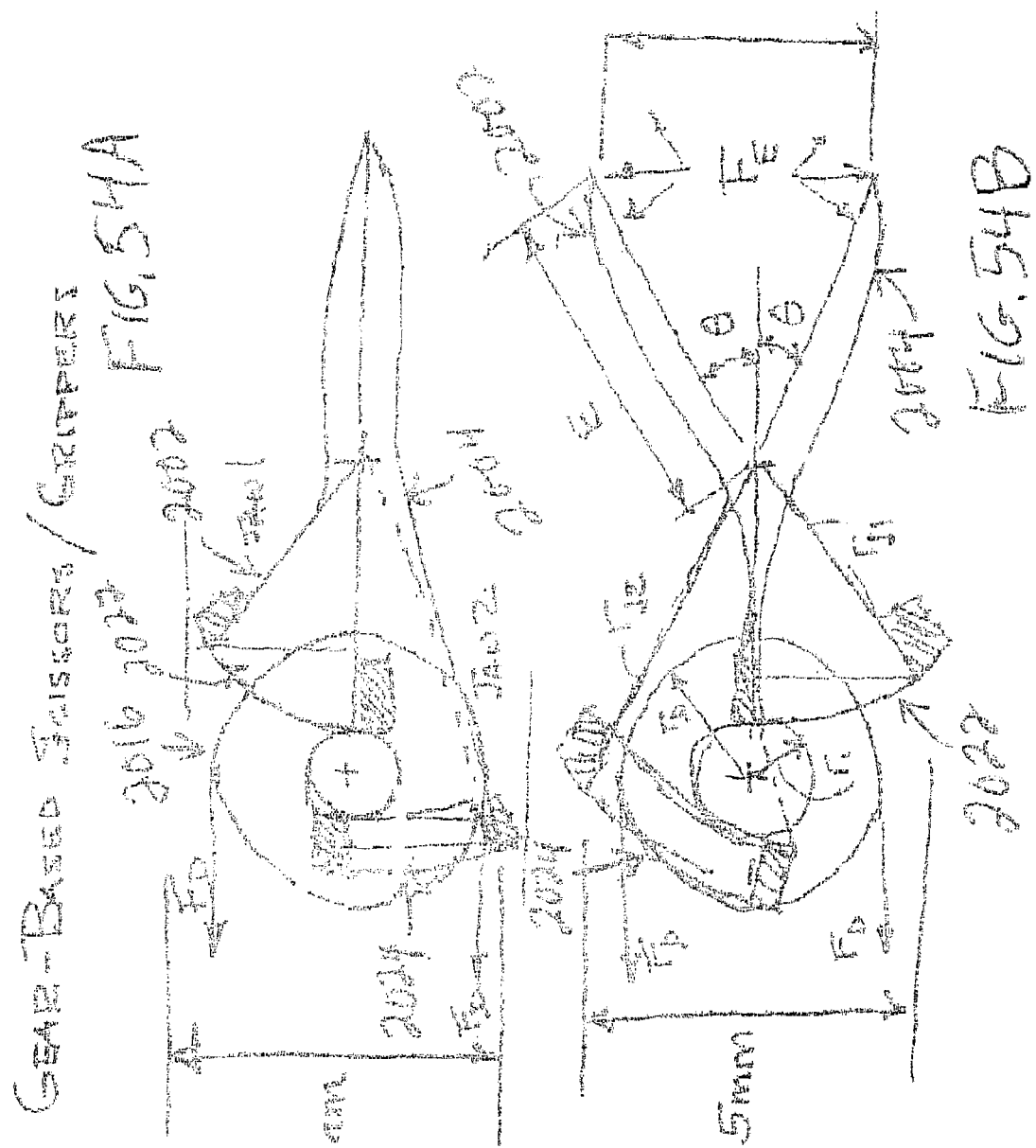

ROBOTICALLY CONTROLLED SURGICAL INSTRUMENTS

RELATED APPLICATIONS

This application claims the benefit of U.S. Provisional Application No. 60/427,525 filed Nov. 18, 2002 and U.S. Provisional Application No. 60/493,425 filed on Aug. 7, 2003 and is a continuation-in-part of U.S. application Ser. No. 10/014,143 now abandoned; Ser. No. 10/008,964 now abandoned; Ser. No. 10/013,046 now abandoned; Ser. No. 10/011,450 now abandoned; Ser. No. 10/008,457 now U.S. Pat. No. 6,949,106; Ser. No. 10/008,871 now U.S. Pat. No. 6,843,793; and Ser. No. 10/012,845, all filed on Nov. 16, 2001, each of which claims the benefit of U.S. provisional Application No. 60/279,087 filed Mar. 27, 2001, and each of which claims the benefit of priority from U.S. application Ser. No. 09/827,643 filed Apr. 6, 2001 which claims priority to, U.S. Provisional Application No. 60/257,869 filed Dec. 21, 2000 and U.S. Provisional Application No. 60/195,264 filed Apr. 7, 2000.

This application is also a continuation-in-part of U.S. application Ser. No. 10/023,024 now abandoned; Ser. No. 10/011,371 now U.S. Pat. No. 7,090,683; Ser. No. 10/011,449 now abandoned; Ser. Nos. 10/010,150; 10/022,038 now abandoned; and Ser. No. 10/012,586, all filed Nov. 16, 2001, and all of which claim the benefit of U.S. Provisional Application Nos. 60/269,200 filed Feb. 15, 2001; 60/276,217 filed Mar. 15, 2001; 60/276,086 filed Mar. 15, 2001; 60/276,152 filed Mar. 15, 2001; and 60/293,346 filed May 24, 2001.

The entire teachings of the above applications are incorporated herein by reference.

BACKGROUND OF THE INVENTION

Various types of instruments are used to perform surgical procedures on living subjects such as human patients. Typically, in the past, the surgeon held the instrument and inserted it into the patient to an internal surgical site. The surgeon then manually manipulated the instrument to perform the operation at the site. These instruments have been used to perform a number of surgical procedures including holding a needle to suture a region of the surgical site, cutting tissue, and grasping tissue and blood vessels.

Recently, some have proposed using telerobotic surgical systems to perform certain surgical procedures. With these systems, the surgeon sits at a master station remotely located from the patient and surgical instrument, and controls the movements of the surgical instrument with an input device. In some systems, the surgeon manipulates the input device with one or both hands, and the instrument replicates the hand and finger movements of the surgeon. Because these replicated movements can be quite complex, the surgical instrument is controlled to move with multiple degrees-of-freedom.

SUMMARY OF THE INVENTION

The present invention implements a robotically controlled medical instrument for grasping an item with a tool used to perform a medical procedure on a subject, as well as methods of using the instrument for such procedures. The instrument includes a first jaw and a second jaw to grasp the item.

The instrument may include a drive mechanism that increases the force applied to an item grasped between the jaws. The drive mechanism and the jaws can be provided with an accommodating mechanism that allows continued movement of the drive mechanism towards a locked position even after the jaws contact a larger item so that the drive mechanism can move to the locked position when grasping items of different sizes.

The accommodating mechanism can be a compliance member. In some embodiments, the compliance member is a resilient member interposed between the linkage and the first jaw. The resilient member is compressed when the jaws grasp the item. The amount the resilient member is compressed depends upon the size of the item being grasped. In other embodiments, the compliance member is a hinge in one of the jaws about which the respective jaw flexes. The amount of flexing is dependent upon the size of the item being grasped. In certain embodiments, the hinge is located below the furthest extent of a gap that extends into the jaw.

In some embodiments, the drive mechanism includes a linkage comprising two links joined by a link pin. One link has a first end connected by a pivot joint to the first jaw and a second end provided with the link pin positioned in a slot of the second jaw, the slot having a curved segment and a relatively straight segment. The two segments together form a slot with a J-shape. The link pin is driven along the straight segment through another link by a driver pin that follows the curved segment. The linkage provides increasing leverage to increase the force applied to the item grasped between the jaws as the link pin moves along the straight segment away from the curved segment. In such embodiments, the accommodating mechanism can be an extended end segment of the slot that extends from the straight segment. The link pin resides in the end segment when the jaws grasp an item. The extent to which the link pin resides in the segment depends upon the size of the item being grasped.

The drive mechanism can include a rotation piece connected to the first and second jaws by a second pivot joint. The driver pin is attached to the rotation such that rotating the rotation piece causes a consequent rotation of the first jaw with respect to the second jaw, while the link and driver pins move along the slot.

The first jaw can be connected through the rotation piece to a drive cable, and the second jaw can be connected to a second drive cable. The jaws can be operated by applying respective tension to the cables. The amount of tension being applied to the respective cables can be controlled with a controller coupled to a user interface operated by a user who provides operating instructions through the user interface.

In some embodiments, a robotically controlled medical instrument coupled to a robotic controller includes an instrument shaft having proximal and distal ends, and a tool supported from the distal end of the instrument shaft and useable in performing a medical procedure on a subject. The tool is constructed and arranged so to be capable of receiving different size items and includes a pair of work members, a drive mechanism which increases the force applied to an item grasped between the work members, and an accommodating mechanism interacting with the drive mechanism and work members and that allows the work members to be closed beyond a maximum grasping position so that the work members can grasp items of various size.

Some embodiments may have one or more of the following advantages. The medical instrument is able to grasp items of different sizes. Thus, a single instrument may be used to grasp items including, but not limited to, needles, sutures, tissue, and blood vessels. The J-slot provides mechanism to lock the jaws onto the grasped item. Hence, the grasped item cannot inadvertently fall out of the instrument. Moreover, the leverage action of the drive mechanism allows the surgeon to apply an increasing grasping force to the item, and therefore minimizes operator fatigue.

A robotically controlled medical instrument end effector construction includes a first jaw, a second jaw and a first pivot for intercoupling said first and second jaws to enable opening and closing thereof. The medical instrument also includes a gear member for engaging respective proximal ends of said first and second jaws. The gear member is supported at a second pivot separate from the first pivot and controlled remotely from a user interface.

A robotically controlled medical instrument end effector construction includes a first jaw, a second jaw and a first pivot for intercoupling said first and second jaws to enable opening and closing thereof. The medical instrument also includes a drive mechanism which increases the force applied to an item grasped between the jaws as it is rotated. The drive mechanism includes a control wheel engaging respective proximal ends of said first and second jaws, supported at a second pivot separate from the first pivot and controlled remotely from a user interface.

A medical instrument end effector for telerobotic control from a remote location, includes a first work member, a second work member and a first pivot for intercoupling said first and second work members to enable opening and closing thereof. The medical instrument also includes a drive mechanism which increases the force applied to an item grasped between the work members as it is rotated. The drive mechanism includes a rotatable member engaging respective proximal ends of said first and second work members, supported at a second pivot separate from the first pivot and controlled remotely from a user interface.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a schematic diagram illustrating the degrees-of-freedom associated with the slave station of FIG. 1;

FIG. 3 is a plan view of the instrument insert of the present invention including the stem section and tool;

FIG. 4 is a cross-sectional view as taken along line 4-4 of FIG. 3 and illustrating further details of the stem section;

FIG. 5 is a perspective view of another embodiment of the tool of the present invention employing a flexible wrist section adjacent the tool;

FIG. 6 is an exploded perspective view of the embodiment of FIG. 5;

FIG. 7 is a cross-sectional view of the embodiment of FIG. 5 and as taken along line 7-7 of FIG. 6;

FIG. 8 is a longitudinal cross-sectional view of the embodiment illustrated in FIGS. 5-7 and showing further details at the wrist flexure;

FIG. 9 is a longitudinal cross-sectional view similar to that shown in FIG. 8 but for still another embodiment of the present invention using a single actuation element;

FIG. 10 is an enlarged fragmentary view of further details of the actuation element at the center of the wrist section;

FIG. 11 is a cross-sectional view through the actuation element of FIG. 10 as taken along line 11-11;

FIG. 12 is a cross-sectional view through still another embodiment of the actuation element;

FIG. 13 is still a further cross-sectional view of a further embodiment of the actuation element;

FIG. 14 is a perspective view of yet another embodiment of the present invention employing a slotted flexible wrist section and a detachable and preferably disposable tool;

FIG. 15 is a cross-sectional view through the embodiment of FIG. 14 as taken along line 15-15 of FIG. 14;

FIG. 41 is a perspective view of an embodiment of a flexible or bendable shaft segment just proximal to the tool;

FIG. 42 is a cross-sectional view of the embodiment of FIG. 41 as taken along line 17-17 of FIG. 16, and with the jaws in a substantially open position;

FIG. 43 is an enlarged partial cross-sectional view similar to that shown in FIG. 42 but with the jaws in a closed position;

FIG. 44 is an exploded perspective view showing the components including the flexible or bendable segment of FIG. 41;

FIG. 48A is a perspective view of an alternate embodiment of the tool and flexible section;

FIG. 48B is an exploded perspective view of the tool and flexible section illustrated in FIG. 48A;

FIG. 48C is a fragmentary perspective view showing a portion of the flexible section shown in FIG. 48B;

FIG. 48D is a plan view of the flexible section illustrated in FIGS. 48A-48C;

FIG. 49 illustrates a flexible instrument being used in a stomach of a subject in accordance with the invention;

FIG. 51 D illustrates the slide member part of the overall end effector illustrated in FIGS. 51A-51C;

FIG. 52B a perspective view of the jaw illustrated in FIG. 52A;

FIG. 54A is a schematic diagram of the tool in a closed position for illustrating transmitted forces;

FIG. 54B is a schematic diagram of the tool in an open position for illustrating transmitted forces;

DETAILED DESCRIPTION OF THE INVENTION

A description of preferred embodiments of the invention follows.

Figure 1:
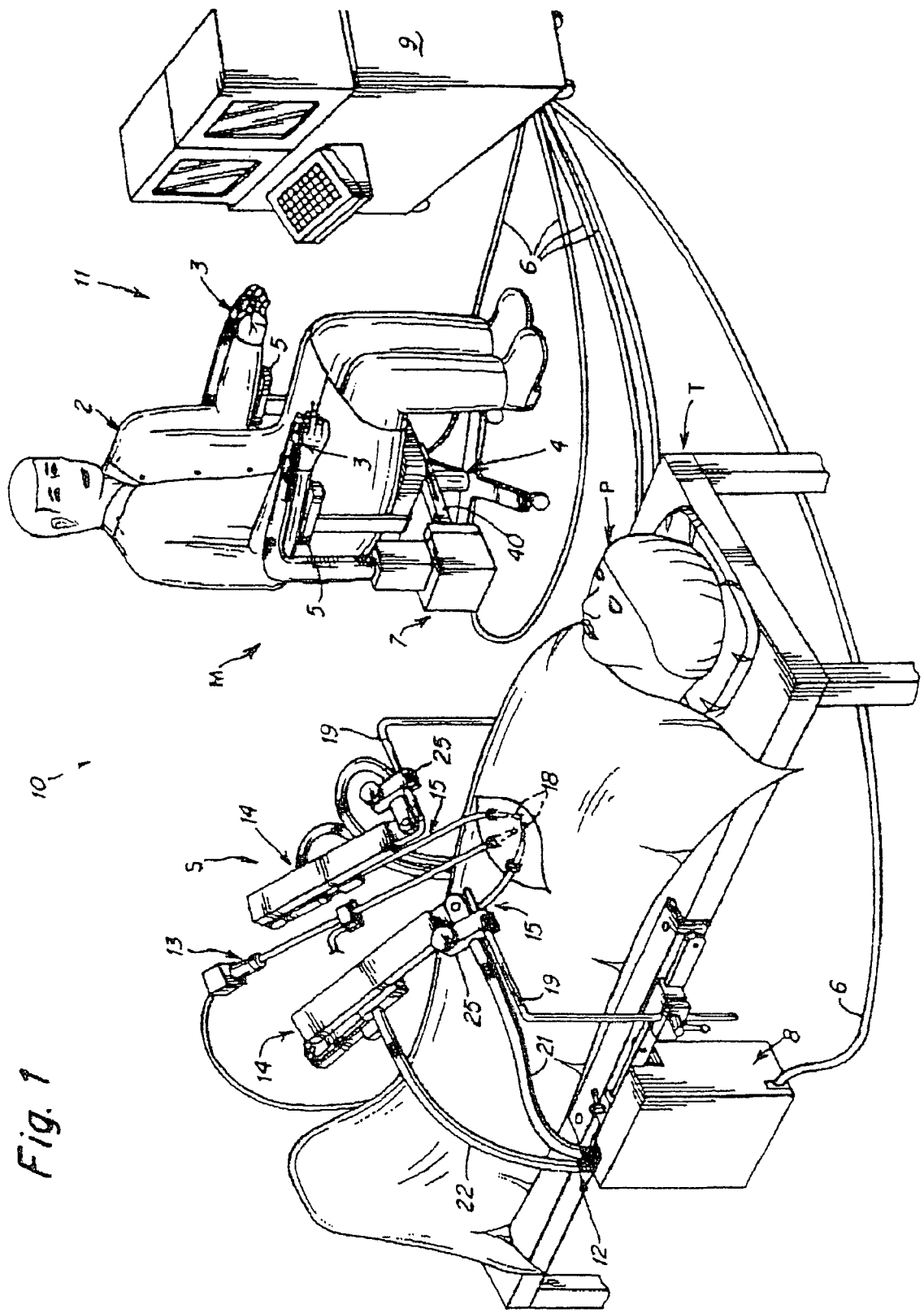
FIG. 1 is a perspective view illustrating a telerobotic system with which the concepts of the present invention may be practiced.

The surgical robotic system of the present invention, as illustrated in the accompanying drawings, although preferably used to perform minimally invasive surgery, can also be used to perform other procedures as well, such as open or endoscopic surgical procedures. FIG. 1 illustrates a surgical instrument system 10 that includes a master station M at which a surgeon 2 manipulates an input device, and a slave station S including a surgical instrument illustrated generally at 14. In FIG. 1 the input device is illustrated at 3 being manipulated by the hand or hands of the surgeon. The surgeon is illustrated as seated in a comfortable chair 4, and the forearms of the surgeon are typically resting upon armrests 5.

FIG. 1 illustrates a master assembly 7 associated with the master station M and a slave assembly 8, also referred to as a drive unit, associated with the slave station S. Assemblies 7 and 8 are interconnected by cabling 6 with a controller 9, which typically has associated with it one or more displays and a keyboard.

As shown in FIG. 1, the drive unit 8 is located remotely from the operative site and is preferably positioned a distance away from the sterile field. The drive unit 8 is controlled by a computer system that is part of the controller 9. The master station M may also be referred to as a user interface vis-à-vis the controller 9. The computer translates the commands issued at the user interface into an electronically driven motion in the drive unit 8, and the surgical instrument, which is tethered to the drive unit through the cabling connections, produces the desired replicated motion. That is, the controller 9 couples the master station M and the slave station S and is operated in accordance with a computer algorithm, to be described in further detail below. The controller 9 receives a command from the input device 3 and controls the movement of the surgical instrument 14 so as to replicate the input manipulation. FIG. 1 also shows a patient P, upon whom the surgical procedure is performed, lying on an operating table T.

In the embodiment illustrated in FIG. 1, the surgical instrument 14 includes two separate instruments one on either side of an endoscope 13. The endoscope 13 includes a camera to remotely view the operation site. The camera may be mounted on the distal end of the instrument insert, or may be positioned away from the site to provide an additional perspective on the surgical operation. In certain situations, it may be desirable to provide the endoscope through an opening other than the one used by the surgical instrument 14. In this regard, in FIG. 1 three separate incisions are shown in the patient P, two side incisions for accommodating the surgical instruments and a central incision that accommodates the viewing endoscope. A drape covering the patient is also shown with a single opening.

The surgical instrument 14 also includes a surgical adaptor or guide 15 and an instrument insert or member 16. The surgical adaptor 15 is basically a passive mechanical device, driven by the attached cable array. Although the surgical adaptor 15 can be easily seen in FIG. 1, the instrument member 16 (FIG. 3) is not clearly illustrated as it extends through the adaptor 15. The instrument insert 16 carries at its distal end a tool 18, described in greater detail below.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

In FIG. 1 there is illustrated cabling 12 coupling the instrument 14 to the drive unit 8. The cabling 12 is preferably detachable from the drive unit 8. Furthermore, the surgical adaptor 15 may be of relatively simple construction. It may thus be designed for particular surgical applications such as abdominal, cardiac, spinal, arthroscopic, sinus, neural, etc. As indicated previously, the instrument insert 16 couples to the adaptor 15, and essentially provides a means for exchanging the instrument tools. The tools may include, for example, forceps, scissors, needle drivers, electrocautery etc.

During use, a surgeon can manipulate the input device 3 at a surgeon's interface 11, to effect a desired motion of the tool 18 within the patient. The movement of the handle or hand assembly at input device 3 is interpreted by the controller 9 to control the movement of the tool 18.

The surgical instrument 14 is preferably mounted on a rigid post 19 that is affixed to but removable from the surgical table T. This mounting arrangement permits the instrument to remain fixed relative to the patient even if the table is repositioned. In accordance with the present invention the concepts can be practiced even with a single surgical instrument, although, in FIG. 1 there are illustrated two such instruments.

The surgical instruments 14 are connected to the respective drive units 8 with cablings that include two mechanical cable-in-conduit bundles 21 and 22. These cable bundles 21 and 22 may terminate at two connection modules, which removably attach to the drive unit 8. For further details of the connection modules 23 and 24 can be found in the earlier co-pending application No. PCT/US00/12553, the entire contents of which are incorporated herein by reference. Although two cable bundles are described here, it is to be understood that more or fewer cable bundles can be used. Furthermore, although the drive unit 8 is preferably located outside the sterile field, it may be draped with a sterile barrier so that it can be operated within the sterile field.

In the preferred technique to set up the system, the tool 18 of the surgical instrument 14 is inserted into the patient through an incision or opening, and the instrument 14 is then mounted to the rigid post 19 using a mounting bracket 25. The cable bundles 21 and 22 are then extended away from the operative area to the drive unit 8, and the connection modules of the cable bundles are engaged into the drive unit 8. Instrument inserts 16 (FIG. 3) may then be passed through the surgical adaptor 15, and coupled laterally with the surgical adaptor 15 through an adaptor coupler, as described below in further detail.

As just mentioned, the instrument 14 is controlled by the input device 3, which is manipulated by the surgeon. Movement of the hand assembly produces proportional movement of the instrument 14 through the coordinating action of the controller 9. It is typical for the movement of a single hand control to control movement of a single instrument. However, FIG. 1 shows a second input device that is used to control an additional instrument. Accordingly, in FIG. 1 two input devices associated with the two instruments are illustrated.

The surgeon's interface 11 is in electrical communication with the controller 9 primarily by way of the cabling 6 through the master assembly 7. Cabling 6 also couples the controller 9 to the actuation or drive unit 8. While the cabling 6 transmits electrical signals, the actuation or drive unit 8 is in mechanical communication with the instrument 14. The mechanical communication with the instrument allows the electromechanical components to be removed from the operative region, and preferably from the sterile field. The surgical instrument 14 provides a number of independent motions, or degrees-of-freedom, to the tool 18. These degrees-of-freedom are provided by both the surgical adaptor 15 and the instrument insert 16.

Shown in FIG. 2 is a schematic representation of the joint movements associated with the slave station S. The first joint movement J1 represents a pivoting motion of the instrument about the pivot pin 225 at axis 225A. Also illustrated is the movement relating to joint J2 which is a transitional movement of the carriage 226 on the rails 224 to move the carriage as well as the instrument 14, supported therefrom, in the direction indicated by the arrow 227 in FIG. 2 towards and away from the operative site OS. The cabling in the bundle 21 controls both the J1 and J21 movements. It is further noted that the distal end of the guide tube 17 extends to the operation site OS. The operation site may be defined as the general area in close proximity to where movement of the tool occurs, usually in the viewing area of the endoscope and away from the incision.

FIG. 2 also depicts the rotary motion of both the adaptor tube 17 and the instrument stem. These are illustrated in FIG. 2 as respective motions or joints J3 (adaptor tube rotation) and J4 (instrument stem rotation). Motion J5 indicates a wrist pivot or, alternatively, a wrist flexure. Finally, motions J6 and J7 represent the end jaw motions of the tool 18.

The combination of joints J4-J7 allows the instrument insert 16 to be actuated with four degrees-of-freedom. When coupled to the surgical adaptor 15, the insert 16 and adaptor 15 provide the surgical instrument 14 with seven degrees-of-freedom. Although four degrees-of-freedom are described here for the instrument insert 16, it is to be understood that greater or fewer numbers of degrees-of-freedom are possible with different instrument inserts. For example an energized insert with only one gripper may be useful for electro-surgery applications, while an insert with an additional linear motion may provide stapling capability.

With regard to the incision point, FIG. 2 shows the incision point along the dashed line 485, and a cannula 487 that in some surgical procedures is used in combination with a trocar to pierce the skin at the incision. The guide tube 17 is inserted through the flexible cannula 487 so that the tool is at the operative site OS. The cannula typically has a port at which a gas such as carbon dioxide enters for insufflating the patient. The cannula also is usually provided with a switch or button that can be actuated to desufflate. The cannula is used primarily for guiding the instrument, but may include a valve mechanism for preventing escape of gas from the body.

FIG. 3 is a plan view showing an instrument insert including the tool 18, and elongated sections including a rigid section 302 and a flexible section 303, with the tool 18 mounted at the end of the flexible stern section 303. The coupler 300 includes one or more wheels that laterally engage wheels of the coupler associated with the surgical adaptor. The coupler 300 also includes an axial wheel 306 that also engages a wheel on the adaptor. The axial engagement wheel 306 is fixed to the rigid stem 302, and is used to rotate the tool axially at the distal end of the flexible stem section 303.

FIG. 3 illustrates the base coupler 300 of the instrument insert 16 with wheels 330, 332, and 334 that have half-moon construction for engagement with mating like wheels of the adaptor. These wheels are meant to mate with the corresponding wheels of the adaptor. Also illustrated in FIG. 3 are capstans or idler pulleys 340, 342, and 344 associated with wheels 330, 332, and 334, respectively.

Each wheel of the coupler has two cables that are affixed to the wheel and wrapped about opposite sides at its base. The lower cable rides over one of the idler pulleys or capstans, which routes the cables toward the center of the instrument stem 302. The cables are kept near the center of the instrument stem, since the closer the cables are to the central axis of the stem, the less disturbance the cables experience as the stem section moves (rotates). The cables may then be routed individually through plastic tubes that may be affixed, respectively, to the proximal end of the rigid stem 302 and the distal end of the flexible stem section 303. Alternatively, the cables may each be enclosed in separate plastic tubes or sheaths only in the flexible section of the instrument stem (see, e.g., bundle 284 in FIG. 4). The tubes assist in maintaining constant length pathways for the cables as they move longitudinally within the instrument stem.

As for the coupler 300, there are six cables that connect to each of the wheels. Two cables connect to each wheel and one of these cables extends about the associated idler pulley or capstan. These are illustrated in FIG. 3 as idler pulleys 340, 342 and 344. Thus, six separate cables extend through the rigid stem 302 and down through the flexible stem section 303 to the area of the tool.

Associated with the wheels 330, 332, and 334 are six cables that extend through the sections 302 and 303, as illustrated in FIG. 4. One set of these cables controls the pivoting, such as the pivoting movement about pin 620. The other cables control the operation at the gripping jaws. For example, one pair of cables may control the movement of the lower jaw 652, while another cable pair may control the operation of the upper jaw 650.

In FIG. 4 there is shown the rigid section 302 and the flexible section 303 of the instrument insert 16. A series of six cables, illustrated at arrow 280 in FIG. 4 extend through these sections and may be considered as separated into three sets for controlling the tool 18, to provide the motions indicated in FIG. 2 as J5-J7. To de-couple wrist control from jaw control, the cabling is supported near to the center axis of the rigid and flexible sections. Note that "de-coupling" simply means that any one controlled action associated with the tool, when performed, does not interfere with other controlled actions that may not be selected at the time that the one controlled action is taking place. This may be controlled to some extent by using a retainer block 282 within these sections between the sections 302 and 303, as depicted in FIG. 4. On the rigid section side of the block 282 the cables may be unsupported as shown or they could be held within a plastic sleeve either individually and/or as a group. Because the cables are maintained in tension and the rigid section is not meant to bend or flex, the cables can be held in position by being supported, as a group, at the center of block 282.

From the other side of block 282 the cables extend through in a bundle 284. Also, each individual cable is preferably held within a cable sleeve, such as illustrated in FIGS. 6 and 8, to be described later in further detail. Also, as shown in FIG. 8 the cables contained in the sleeves 292 are twisted, for example, 180 degrees over say 8 inches. As also shown in FIG. 4, spacers 286 may be spaced along the flexible section 303 to hold the bundle 284 at the center of the section 303. The individual cable sleeves also define a substantially fixed length pathway for each cable so that even though the instrument may move or rotate, the cable lengths should stay the same within the flexible stem section. The sleeves may be held in fixed position at their ends such as at block 282 at one end and at the tool 18 at the other end. The outer flexible tube 288 may be a pliable plastic preferably having a fluted or bellows-like configuration, as illustrated.

The limited twisting of the cable bundle prevents the formation of kinks or loops in individual cables that might occur if the cables were straight and parallel through the flexible section. This twisting is also provides the de-coupling between motions, so that actuation of one of the degrees-of-freedom (J5-J7) does not cause a responding action at another degree-of-freedom (J5-J7). The twisting essentially occurs between the block 282 and the location where the bundle enters the wrist joint (for example, the entry to base 600). The 180 degree twisting of the bundle ensures that the cable sheathes are neither stretched nor compressed, even as the bendable section is bent or rotated.

The construction of one form of tool is illustrated in FIGS. 3 and 4. The tool 18 includes the base 600, link 601, upper grip or jaw 650 and lower grip or jaw 652. The base 600 is affixed to the flexible stem section 303. As illustrated in the drawings, this flexible section may be constructed of a ribbed plastic. This flexible section allows the instrument to readily bend through the curved actuator tube 17.

The link 601 is rotatably connected to the base 600 about an axis 620A represented by pivot pin 620. The upper and lower jaws 650 and 652 are rotatably connected to the link about axis 605, where axis 605 is essentially perpendicular to the wrist axis at pin 620. Another pivot pin defines axis 605.

Six cables actuate the separate members 600-603 of the tool. The cabling may travel through the instrument insert stem (section 303) and through a hole in the base 600, wrapping around a curved surface on link 601, and then attaches on link 601. Tension on one set of cables rotates the link 601, and tension on other cables operates the upper and lower grips 650 and 652, about axis pin 605. The cabling is provided in pairs to provide an opposing action operation, including opposite routing paths, on the opposite sides of the instrument insert.

The set of cables that control the jaws travels through the stem 302, 303 and though holes in the base 600. These cables then pass between two fixed posts 621 that constrain the cables so that they pass substantially through an axis 620A, which defines the rotational motion of the link 601. This construction allows free rotation of the link 601 with essentially no length changes in the cables that actuate the jaws. In other words, these cables, which actuate the grips 650 and 652, are effectively decoupled from the motion of link 601. These cables pass over rounded sections and terminate on grips (or jaws) 650 and 652, respectively. Tension on one pair of cables rotate grips 650 and 652 counter-clockwise about axis 605. Another set of cables provides the clockwise motion to grips or jaws 650 and 652, respectively. The ends of the cables can be secured at the jaws 650 and 652 with the use of an adhesive such as epoxy glue, or the cables could be crimped or pinned to the jaw.

The instrument 16 slides through the guide tube 17 of adaptor 15, and laterally engages the adaptor coupler 230 pivotally mounted to the base piece 234. The base piece 234 is rotationally mounted to the guide tube 17, and is affixed to the linear slider or carriage 226. The carriage 226, in turn, is pivotally mounted at the pivot 225 about the axis 225A.

The embodiment of the invention illustrated in FIGS. 2-4 employs a fixed wrist pivot. An alternate construction is shown in FIGS. 5-8 in which there is provided, in place of a wrist pivot, a controllable flexing or bending section. In FIGS. 5-8, similar reference characters are used for many of the parts as they correspond to elements found in FIGS. 2-4. The construction in FIG. 5 may be employed with a stem section such as illustrated in FIGS. 3 and 4 with a curved guide tube.

In the embodiment illustrated in FIGS. 5-8, the tool 18 includes an upper grip or jaw 650 and a lower grip or jaw 652, supported from a link 601. Each of the jaws 650, 652 as well as the link 601, may be constructed of metal, or alternatively, the link 601 may be constructed of a hard plastic. The link 601 is engaged with the end of the flexible stem section 303. In this regard reference may also be made to FIG. 4 that shows the ribbed or fluted plastic construction of the flexible stem section 303. Alternatively, the section 303 may be smooth, at least at its distal end, as shown at 304 in FIG. 5. In still another embodiment both sections 302 and 303 can be rigid depending upon the particular application.

FIG. 5 shows only the end of the stem section 303 (at 304), terminating in bending or flexing section 660. Section 660 may be integrally formed with the rest of section 303. This section 660 is controllably bendable or flexible usually from a remote location such as in accordance with the telerobotic system 10 of FIG. 1. The stem section 303 is preferably constructed so as to be flexible and may have either fluted or smooth outer surfaces. Also, at the flexible section 660, flexibility and bending is enhanced by a bellows configuration 662 having saw-tooth shape of peaks and valleys as shown in FIG. 8. The distal end of the bending section 660 terminates with an opening 666 for receiving the end 668 of the link 601. The bellows configuration may be made of a single piece of material. Alternatively, the bellows configuration 662 may be made of segments connected together, for example, by welds. In any case, the bellows configuration 662 is a unibody construction.

In the embodiment shown in FIGS. 5-8, the bending or flexing section 660 is constructed to have orthogonal bending movements to provide both pitch and yaw movement of the tool. This is accomplished by using four cables separated at 90° intervals. These four cables include the cables 606, 607, 616, and 617. The operation of cables 606 and 607 provides flexing in one degree-of-freedom while an added degree-of-freedom (orthogonal to the just mentioned one degree-of-freedom) is provided by operation of cables 616 and 617. As illustrated in FIG. 8, these cables extend through the bellows about half way between each peak and valley and thus run in parallel but close to the outer periphery of the flexible section 660. Each of the cables 606, 607, 616, and 617 terminate in a respective ball end 606A, 607A, 616A, and 617A, tensioned against an end wall 615. These same cables also are supported by and extend through retainer block 621. Within section 304 these cables also run near the outer wall as shown to the left in FIG. 8 where cables 616 and 617 are illustrated.

As for the operation of the tool, the cables 608, 609, 610, and 611 extend through the flexible stem section 303 and also through the retainer block 621, flexing section 660, and the wall 615. These cables extend to the respective jaws (650, 652) to control the operation thereof in a manner similar to that described previously in connection with FIGS. 2-4.

As is apparent from FIGS. 6-8, within the bellows 662, the tool actuation cables extend through the center of the bellows and are supported and retained between block 621 and wall 615 by the center sheath 290. The center sheath 290 may be constructed of a soft plastic material, and has an inner diameter sufficient to receive the bundle of cables, and an outer diameter that fits with little clearance against the inner diameter of the bellows 662. The sheath 290 extends between the block 621 and the wall 615 and is dimensioned to hold the cables, as a bundle, at the center axis of the bellows section. Keeping the bundle near the center axis provides proper de-coupling between the various degrees-of-freedom.

Also, within the bellows 662 each of the cables is contained in its own cable sleeve 292. These sleeves are sufficiently stiff to maintain constant cable lengths within the flexible or bendable section. In FIG. 8 these sleeves are shown extending between retainer block 621 and wall 615. As shown in the right most portion of FIG. 8, the cables are shown extending from the sleeve when the cables reach the end tool. FIG. 8 also illustrates the aforementioned twisting of the cables that assists in providing the de-coupling action between the tool operation and the controlled flexing or bending. The cables are twisted about 180 degrees between the block 621 and wall 615. The bellows section itself, may have a length of about one to three inches. Also, more than one bellows section may be used to provide controlled bending at more than one location. In that case separate control cabling is used for each section (see, e.g., FIG. 21 described later).

As with the earlier described embodiment, the limited twisting of the cable bundle prevents the formation of kinks or loops in individual cables that might occur if the cables were left straight and parallel to one another. This twisting also de-couples certain degrees of motions, so that actuation of one of the degrees-of-freedom does not cause a responding action at another degree-of-freedom. The twisting occurs between the block 621 and the location where the bundle enters the wrist joint, i.e. the entry to base 601. By twisting the cables through 180 degrees, the placement of all the cables is displaced from one end of the bundle to the other by 180 degrees. The individual cable sleeves also define a substantially fixed length pathway for each cable so that even though the instrument may move or rotate the cable lengths stay the same within the section 660.

The cross-sectional view of FIG. 8 gives details of the cabling in bending section 660. The sheath 290 extends essentially between block 621 and wall 615 and houses the twisted cables/sleeves. The individual sleeves 292 can be considered as terminating at respective ends in blocks 621 and 631. Each of the sleeves may be glued or secured in any other appropriate manner in its supporting end block. This prevents the sleeves from moving axially as the cables are activated. The sleeves are preferably constructed of a plastic that is flexible and yet has sufficient rigidity so they do not kink when the cables are activated. The sleeves also define fixed length pathways that do not compress or elongate as the cables are operated.

The 180 degrees twist in the cables/sleeves occurs essentially between blocks 621 and 631. This "twisting" of the center cables/sleeves allows the section 660 to be controllably bent, while preventing or minimizing any transfer of motion to the tool operating cables. Similarly, this arrangement also prevents cross-coupling from the tool operation to the bending control, so that the tool operation alone does not cause any undesired bending of the section 660.

Referring now to FIGS. 9-13 there is shown another embodiment that includes bellows which can be bent of flexed in a controllable manner, for example, through a user interface like that shown in FIG. 1. Similar reference characters are used in FIG. 9 as those used in describing the embodiment of FIG. 5. Unlike the embodiment shown in FIG. 5, the embodiment of FIG. 9 provides a single cable (or rod) actuation that simplifies the instrument construction, particularly at the tool end of the instrument. The single actuation is possible because the flexible section has two degrees-of-freedom to provide both pitch and yaw.

In the embodiment illustrated in FIGS. 9-13, the tool 18 includes an upper grip or jaw 650 and a lower grip or jaw 652, supported from a housing 670. Each of the jaws 650, 652, as well as the housing 670, may be constructed of metal, or alternatively, the housing 670 may be constructed of a hard plastic. The housing 670 is engaged to the flexible stem section 303 with the bellows 662. The flexible stem section 303 can be a ribbed or fluted plastic construction like that shown in FIG. 4, or alternatively, the section 303 may be smooth as shown at 304 in FIG. 9.

In FIG. 9 the jaws are operated from a single push/pull cable 672 that extends through the instrument stem and through the bellows 662 of the flexible or bendable section 660. The cable is centered in the various sections as depicted in FIG. 9 so that when the bendable section is activated, no movement is transferred to the tool actuation cable. In essence, the bellows section 662 expands on one side and compresses on the other side, leaving the center portion unchanged in length, and thus not effecting the cable action. The jaws themselves are supported by a link bar arrangement shown at 675 that is appropriately secured at the distal end of the cable 672. In the position shown in FIG. 9 the jaws are open, but by pulling on the cable away from the jaws the proximal end the link bar 675 pivots and closes the jaws 650, 652.

FIG. 9 shows only the end portion of the stem section 303, i.e., the portion at 304, terminating in bending or flexing section 660. This section 660 is bent or flexed in a controllable manner usually from a remote location as depicted FIG. 1. The stem section 303 is preferably constructed to be flexible and may have either fluted or smooth outer surfaces. Also, at the bending or flexing section 660, flexibility and bending is enhanced by means of constructing this section with a bellows configuration 66 having peaks and valleys in a saw-tooth shape arrangement as illustrated in the cross-sectional view of FIG. 9. The distal end of the bending section 660 has an opening for receiving the end of the housing 670. A wall 615 is positioned at the distal end of the bellows 662.

In the embodiment shown in FIG. 9, the bending or flexing section 660 can be bent to provide both pitch and yaw degrees of motion to the tool. This is accomplished by using four cables 606, 607, 616, and 617 that are separated at 90° intervals. The operation of cables 606 and 607 provides flexing in one degree-of-freedom while another degree-of-freedom is provided by the operation of cables 616 and 617. As illustrated in FIG. 9, these cables extend through the bellows about halfway between each peak and valley of the respective bellows, and thus are parallel and near the outer periphery of the flexible section 660. Each of the cables 606, 607, 616, and 617 terminates in a respective ball end 606A, 607A, 616A, and 617A, tensioned against the end wall 615. These cables also are supported by and extend through retainer block 621. Within section 304 these cables also run near the inner surface of the outer wall of the section 304, as shown to the left in FIG. 9 where cables 616 and 617 are illustrated. As mentioned previously, the single actuation cable 672 provides all the action that is required to operate the tool, which simplifies the construction of the instrument and makes it easier to keep the single cable centered in the instrument. To accomplish this, there is provided a supporting sleeve 680 that receives the cable 672 with a snug fit. The sleeve 680 (FIG. 10) is preferably constructed of a polyethylene plastic such as PEEK which has the flexibility to flex with bending at the section 660, but at the same time is sufficiently rigid to properly retain and hold the supported cable 672 to enable the cable to readily slide within the supporting sleeve 680 when performing its function. Sleeve 680 defines a fixed length for the cable and does not allow any expansion or compression of the cable or sleeve. The sleeve 680 may extend from the wall 615 back through the retainer block 621 and into the flexible section of the instrument, as shown in FIG. 9. Alternatively, the sleeve 680 may extend only through the section 660 and terminate at block 621.

In addition to the sleeve 680, there is provided, about the sleeve 680, a helical spring 682 having an outer diameter to allow it to fit snugly within the inner diameter of the bellows 662. Note that there is a relatively close fit between the cable 672, sleeve 680, and helical spring 682 within the bellows 662. Opposite ends of the helical spring 682 are located between the block 621 and wall 615. FIG. 10 shows the spring shape and the relationship of the helical spring to the sleeve 680 and the actuation cable 672. In FIG. 10, the coils of the spring are shown spaced apart, but they can be more closely spaced then shown or completely closed.

The spring 682 may be free-floating about the sleeve 680, and is preferably not engaged in any passage in the end supports, such as the passage in block 621. The sleeve 680, on the other hand receives the cable 672 and is fixed in position relative to block 621 and wall 615. Passages are provided in block 621 and wall 615, and a glue or other securing arrangement is preferably used to hold the sleeve fixed at the block 621 and wall 615. The spring 682 is also used as a filler or spacer between the sleeve 680 and the bellows 662 inner surface. The spring provides a fixed position spacer since it is typically a metal, and thus will maintain the centering of the sleeve/cable, and yet is also flexible enough to bend when the section 660 is bent in a controlled manner. The sleeve itself is preferably made of plastic such as PEEK which has sufficient strength to receive and guide the cable, yet is flexible enough so that it will not kink or distort, and thus keeps the cable in a proper state for activation, and defines a fixed length for the cable.

By maintaining the sleeve 680 fixed in position at the block 621 and wall 615, the cable length at the center axis of section 660 does not change when the section 660 is bent. That is, the bellows shortens on one side and expands on the other side while keeping the center axis length unchanged. In this way when bending occurs at section 660 there is no transfer of motion to the cable 672 which could undesirably move the jaws. Hence, the bending motion is de-coupled from the tool operation motion, and vice versa.

FIG. 11 is a cross-sectional view taken along line 11-11 of FIG. 10 showing the centered cable 672, plastic sleeve 680, and the helical spring 682. FIG. 12 is a similar cross-sectional view but for an alternate embodiment using only the center cable 672 and the sleeve 680. In FIG. 12 the sleeve 680 is larger in outer diameter in comparison to the sleeve shown in FIG. 11 so that there is a proper and close fit between the sleeve and the inside of the bellows.

FIG. 13 is a cross-sectional view through another embodiment of the cable support. This embodiment also has the center cable 672 contained within the sleeve 680, but in place of the spring 682 there is instead used a spacer 681 made of, for example, plastic, to keep the sleeve and cable centered in the bellows. The spacer 681 may be constructed of a softer plastic than the sleeve 680, or may be made of a plastic foam material.

One of the benefits of the embodiment of FIG. 9 is that only a single cable is necessary to activate the tool. Recall that the pitch and yaw of the tool is controlled at the flexible wrist section 660 shown in FIG. 9. This arrangement lends itself to making the tool disposable or at the very least detachable from the instrument body so that it can be replaced with a substitute tool. A detachable embodiment of the present invention is illustrated in FIG. 14 and the companion views are shown in FIGS. 15-20. Besides being detachable this arrangement also makes it possible to provide at least a resposable and preferably a disposable instrument tip or tool.

In FIG. 14 a disposable tip is illustrated in conjunction with a flexible shaft or tube having a remotely controllable bending or flexing section 700. The medical instrument may include an elongated shaft, such as shaft section 710 shown in FIGS. 14 and 15, having proximal and distal ends, and a tool, such as graspers 702 and 704, supported from the distal end of the elongated shaft and useable in performing a medical procedure on a subject. The distal end of the elongated shaft and the tool have respective removably engaging portions that are readily engagable for positioning the tool at the distal end of the elongated shaft, and readily disengagable for removal of the tool from the distal end of the elongated shaft. The tool may be detachable to facilitate substituting another tool, or the tool may be constructed to be readily disposable. The removably engaging portions may be snap-fitted together, or, as illustrated here, may be provided by a screw interlock between the distal end of the instrument shaft and the base or housing of the tool. Also, other forms of detachable engaging portions are considered as falling within the scope of the present invention.

As shown in FIG. 14, the detachable or disposable tool is used with a flexible controllably bendable section. In another version the disposable tool can be used with a wrist pivot or even a pair of successive wrist pivots that are orthogonal to one another for providing pitch and yaw movement at the tool. The disposable tool in this version is also preferably actuated by a single actuation element, cable or the like.

In FIGS. 14 and 15, in a manner similar to that shown in FIG. 9, the tool is actuated by a single tendon or cable 736 that extends through the flexible section 700. To provide the pitch and yaw action at the tool, the bending or flexing section 700 is constructed to have orthogonal bending movements by pulling on four cables 706, 707, 716, and 717 separated at about 90° intervals, and by using a center support 726 with ribs 712 extending from the center support 726 and defining slots 714 between adjacent ribs, as depicted in FIG. 15. The ribs 712 extend from a center support 726 that has extending therethrough a passage for receiving the cable 736 positioned within a sheath 730. The ribs 712 also provide a guide structure to the four cables 706, 707, 716, and 717. The bending section 700 is a unibody construction that extends from the end of tube section 710, which itself may be flexible, and it may be smooth as shown, or may be fluted as illustrated in FIG. 4.

This version enables the bending section to be bent in orthogonal directions by the use of the four cables 706, 707, 716, and 717. The operation of cables 706 and 707 provides flexing in one degree-of-freedom while another orthogonal degree-of-freedom is provided by the operation of cables 716 and 717. Each of the cables 706, 707, 716, and 717 has at their terminating ends respective balls 706A, 707A, 716A, and 717A that may be held in corresponding recesses in a distal end wall 719 of the flexible section 700. Note that in place of the slotted bending section 700, a bellows arrangement such as shown in FIGS. 5 or 9 can be used.

The structure shown in FIGS. 14-17 preferably includes a plastic stiffener sheath or sleeve 730 that surrounds the cable 736, and that fits closely within the passage of the center support wall 726. The sleeve 730 is preferably constructed of a polyethylene plastic such as PEEK which has enough flexibility to flex with the bending section 700, but at the same time is sufficiently rigid to properly retain, center and hold the supported cable to allow the cable 736 to readily slide within the supporting sleeve 730 in performing its function. The sleeve 730 may extend from the distal end of the flex section 700, back through the passage in the wall 726, and into the shaft section 710 of the instrument, as shown in FIG. 15.

Figure 15A:
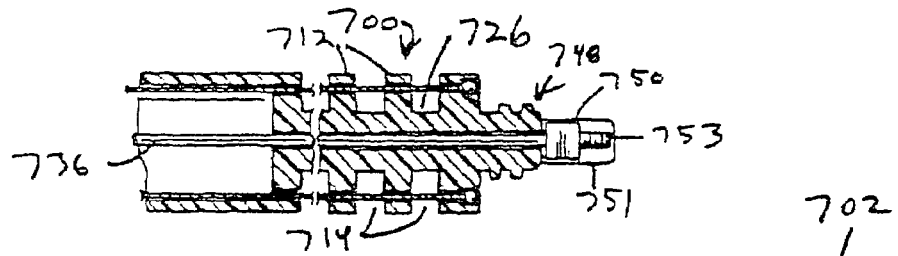
FIG. 15A is a fragmentary cross-sectional view of an alternate embodiment of the flexible section.
Figure 16:
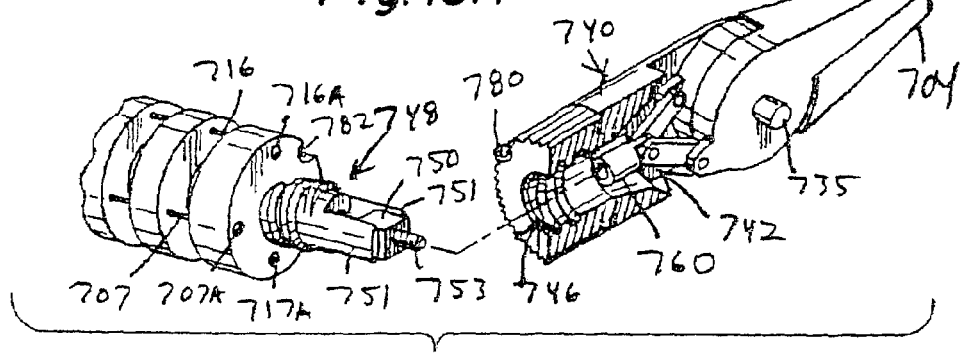
FIG. 16 is an exploded perspective view of the embodiment of FIG. 14 showing the detached tool in cross-section.

Referring to FIG. 15A there is shown an alternate embodiment for the bending section 700 in which the sleeve 730 is eliminated. In this case, the passage in the wall 726 is dimensioned to directly and snugly receive the cable 736 with a close tolerance fit but having sufficient clearance to allow the cable to readily slide in the instrument. The grippers 702 and 704 are supported for opening and closing by the use of a pivot pin 735 that extends along axis 735A in a housing 740. Referring to FIG. 16 there is shown in partial cross-section the housing 740, pin 735, and grippers 702 and 704. The pin 735 may be supported at its ends on opposite sides of housing 740. The tool also includes a pivot linkage 742 that intercouples the grippers with the actuation cable 736 such that as the linkage is moved in the axial direction by the cable 736 to open or close the jaws (or grippers). In FIG. 15 the linkage and tool are shown in solid outline in the closed position, which corresponds to a "pulling" of the cable in a direction away from the tool. FIG. 15 also shows, in dotted outline, the linkage and grippers in an open position, which corresponds to a "pushing" of the cable in a direction toward the tool. The grippers themselves are prevented from any axial movement by the support at pin 735, so when the linkage is operated from the cable 736 the resulting action is either opening or closing of the grippers, depending upon the direction of longitudinal translation of the actuating cable 736.

Figure 17:
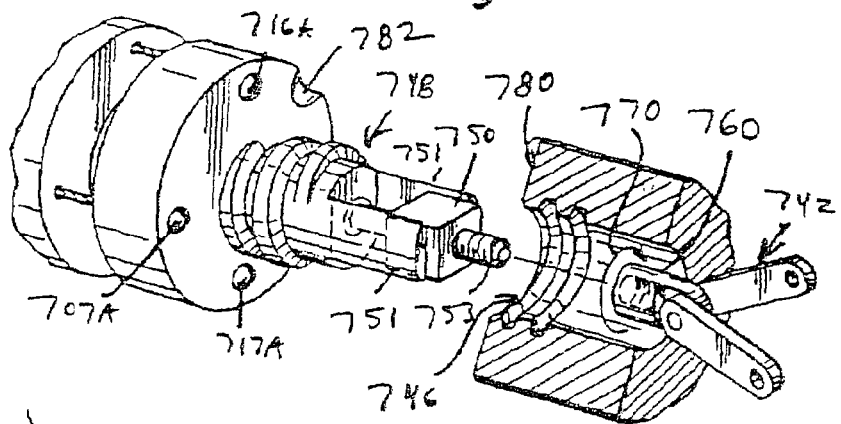
FIG. 17 is a further perspective view of the embodiment of FIG. 14.
Figure 18:
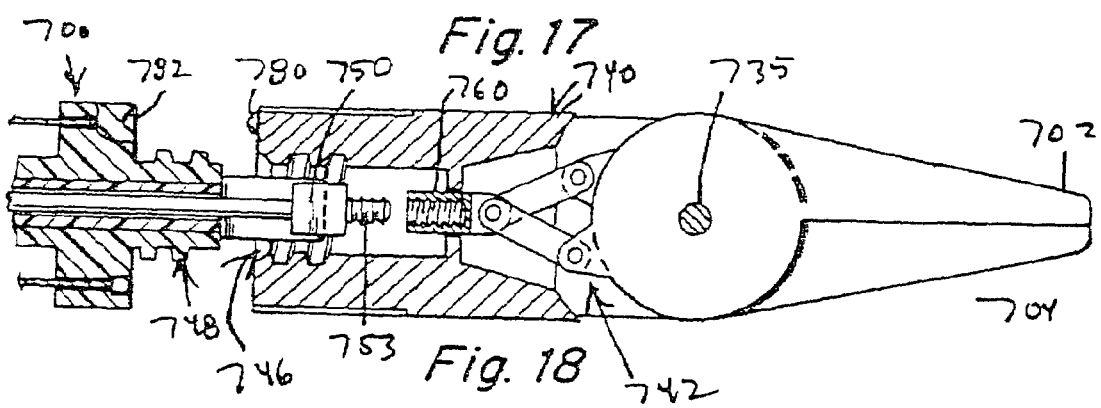
FIGS. 18-20 illustrate sequential cross-sectional views showing the mating of the tool with the distal end of the instrument.
Figure 19:
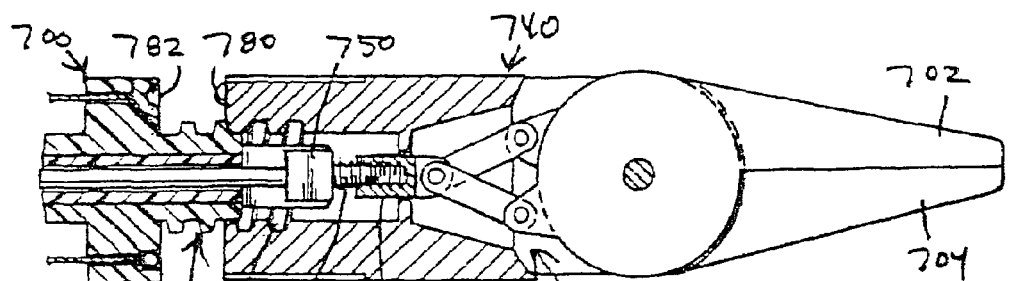
Figure 20:
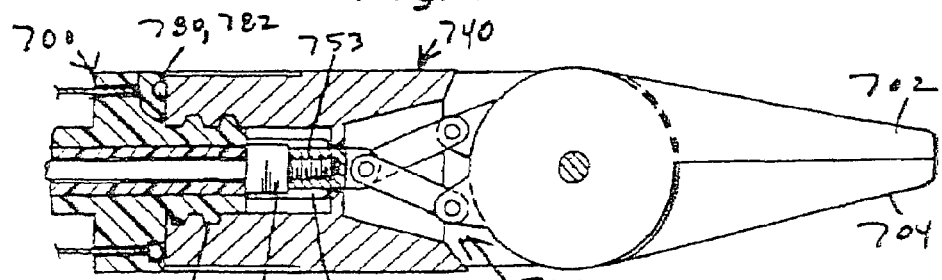

For the tool shown in FIGS. 14-17 to be detachable there is provided removably engaging portions, which in the illustrated embodiment are formed by mating threaded portions. Further, these mating portions are provided both with respect to the actuation element (cable) as well as the stationary components of the tool and tube. Thus, the tool housing has a threaded portion 746 with female threads, and the distal end of the flexible section 700, as shown in FIG. 16, has a threaded portion 748 with male threads. The end of the actuation cable 736, as shown in FIGS. 16 and 17, is terminated at block 750, passing through a center passage in the threaded portion 748. The block 750, interacting with arms 751, allows longitudinal sliding of the cable 736, but prevents rotation thereof so that the tool can be screwed onto the shaft without rotating the actuation cable. The block 750 supports a male threaded shaft 753 that is adapted to mate with the tool. The threaded portion at 753 may have twice the threads per length as the threaded portion 748. Also, the block 750 interacts with the arms as the tool is fully engaged to compensate for differences in thread pitch between the engaging members As previously indicated, the tool grippers are operated with the linkage 742. FIG. 17 shows the end of this linkage supporting a female threaded piece 760. To engage the tool with the instrument shaft, the female piece 760 is threaded onto the male threaded shaft 753 in the direction indicated by the rotational direction arrow 770. Referring to FIGS. 18-20, there is shown the sequence of steps to attach the instrument tip to the shaft of the instrument. These views are somewhat schematic and are for the purpose of merely illustrating the steps taken in attaching the tool to the instrument shaft.

In FIG. 18 the tool is first illustrated with its housing 740 about to engage at threaded female piece 760 with the corresponding threaded male shaft 753. It is noted that the threads of pieces 760 and shaft 753 are finer that the threaded portions 748 and 746. Also, the threaded piece 760 and shaft 753 are designed such that only about four turns are necessary to fully seat these members together. On the other hand the sections 746 and 748 have courser threads so that it takes, say, only about two turns to engage the two sections together. When the tool is fully engaged there is a detent arrangement provided between the interlocking members to lock them in their final position. This is shown in the drawings by interlocking tab 780 of housing 740, and recess 782 associated with the flexible section 700.

FIG. 19 illustrates the positions of the various components after two turns have occurred between threaded shaft 753 and threaded piece 760, and the other outer mating threaded sections are to engage. Next the threaded portions 746 and 748 engage and after two more turns of the tool, the tool is fully engaged with the shaft, as illustrated in FIG. 20. In that position the detents are also engaged so that the tool is, in essence, locked to the instrument shaft and ready for use. It is also noted in FIG. 20 that because of the difference in thread pitch between the fine and course threads, the block 750 is free to move inward away from the tool.

Figure 21:
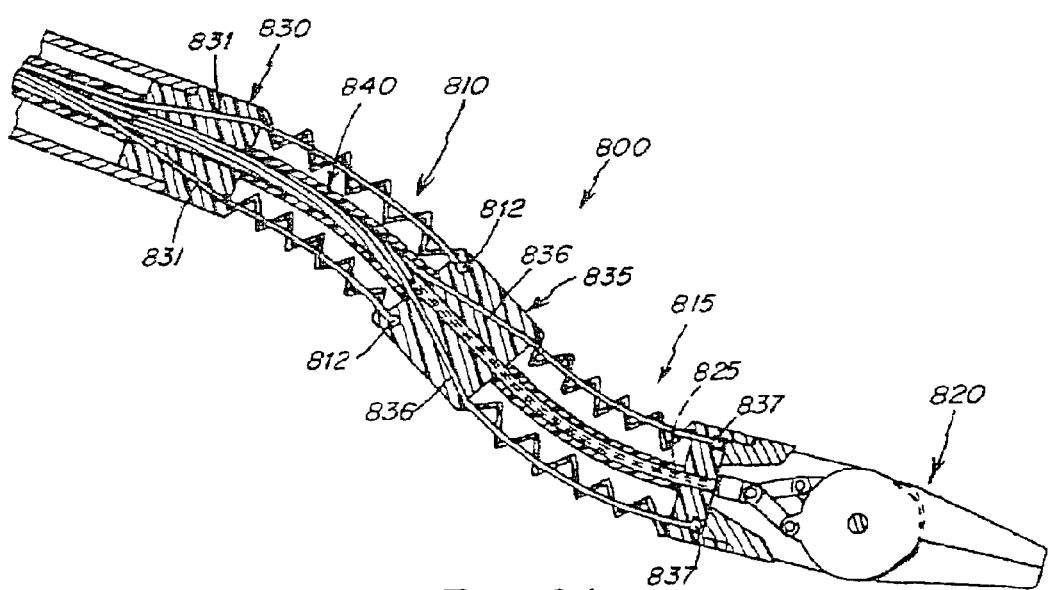
FIG. 21 is a schematic diagram illustrating principles of the present invention in a catheter or flexible instrument using multiple controllable bendable sections along the instrument.

Referring now to FIG. 21, there is shown an embodiment having a detachable and disposable tool, and particularly adapted for application to a flexible instrument including a catheter. Features of the earlier described embodiments may be used with the embodiment of FIG. 21. Again, although not necessary, in a preferred embodiment the tool is operated remotely in a telerobotic manner from a user device such as shown in FIG. 1. The use of multiple controllably bendable segments as shown in FIG. 21 is particularly advantageous in a flexible instrument to assist in guidance thereof such as, for example, in vessels or arteries.

FIG. 21 shows primarily the distal end of a flexible instrument with the more proximal portions of the instrument being supported and driven in a manner similar to that illustrated in FIGS. 1 and 2. Rather than having only one bending or flexing section as described above, the flexible instrument 800 has two bending sections 810 and 815 spaced along the instrument shaft that are remotely actuable. In other configurations, these sections 810 and 815 can be formed directly in series, and more than two controllable segments can be used.

A tool 820 is positioned at the distal end of the instrument, and is preferably constructed to be disposable and may be substantially the same as the tool illustrated in FIGS. 14-17 including the interengaging portions for detachability of both the tool body and the tool actuation element. As shown in FIG. 21, a cable 825 is used as the actuation element. Also illustrated in FIG. 21 are instrument transition segments 830 and 835, which may be similarly constructed as the flexible section 303 shown in FIG. 4. Alternatively, one or both of these sections 830, 835 may be rigid.

In each of the instrument sections shown in FIG. 21 the actuation elements (cables) that are not used to operate a particular section run preferably through the center of the respective section to provide the proper de-coupling between the various degrees of movement. Thus, the center cable bundle 840 through the section 810 includes the cables to operate section 815 and the tool 820.

If the two controllable sections 810 and 815 are controlled with both pitch and yaw movements, then four cables are used to actuate each section. Thus, the actuation of each section is similar to the actuation of the embodiments shown earlier in FIGS. 5 and 9. The aforementioned "twisting" concept is also preferably used in each of these sections 810, 815 where multiple cables are running through them, particularly in section 810 where five cables extend along the center of the section (four for actuation of the section 815 and one for tool actuation) similar to that shown in FIG. 8.

Thus, nine cables extend through section 830, five in the center bundle 840 and four extending through and about the periphery of section 810 to provide the controlled bending of section 810. FIG. 21 shows two of these cables terminating at 812 and used to operate and move the section 810 with one degree of freedom. Two other cables (displaced about 90 degrees) also terminate at the same general area and are used to operate the bending section 810 with the other degree-of-freedom.

Next, in section 835 four cables at 836 branch outwardly and terminate at the end of section 815 at 837 to control the flexing of section 815. In section 815 there is thus only the single tool actuation cable 825 contained in a sheath extending through the center of the section. Although FIG. 21 shows only two of the cables 836 for controlling one of the degrees-of-freedom of movement of the section 815, there are two other cables (displaced about 90 degrees) that also terminate at the same location for the other degree-of-freedom of control of section 815. Again, reference to FIG. 8 can be made for the operation of the bending movement of the sections with the use of the cables.

The instrument shown in FIG. 21 may be used for any number of different surgical procedures. Flexible instruments of this general type are shown in co-pending applications that have been incorporated herein by reference in their entirety. Although FIG. 21 shows four cables that are used to actuate a respective bending section, more or fewer cables can be used in each section. For example, if only one degree-of-freedom is desired in section 810 then only two actuating cables are employed to control bending in only one plane. The instrument may also be controlled for rotation to provide another degree-of-freedom.

In the embodiment of the invention shown in FIGS. 14-17, the tool is readily disposable. By providing a bendable section that can control both pitch and yaw movement of the tool, the tool itself becomes actuable with a single cable or rod. Now, FIGS. 22 and 23 disclose in a schematic manner this same disposability feature as applies to an instrument, whether flexible or rigid, that employs a wrist pivot or wrist and elbow pivot.

Figure 22:
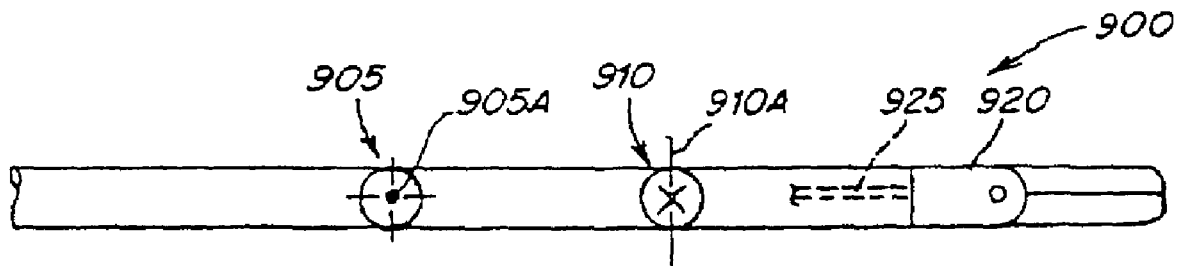
FIG. 22 is a schematic diagram of an embodiment of an instrument with both elbow and wrist pivot joints, as well as a disposable tool.
Figure 23:
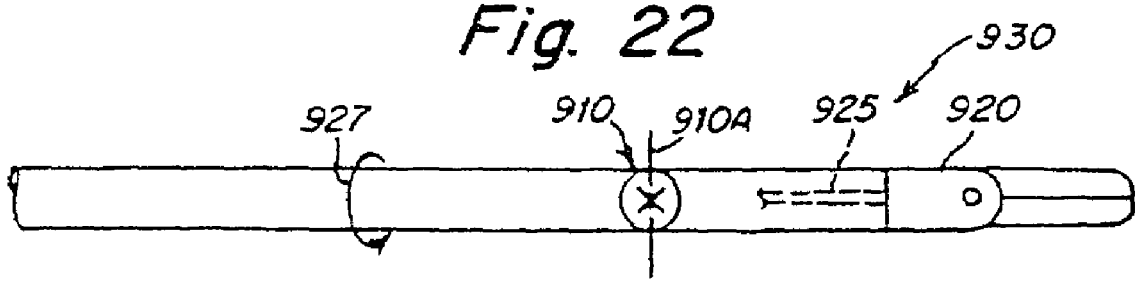
FIG. 23 is a schematic diagram of an embodiment of an instrument with just a wrist pivot joint, as well as a disposable tool.

FIG. 22 is a schematic diagram of the instrument illustrating both elbow and wrist pivot joints, as well as the disposable tool. FIG. 23 shows just a wrist pivot joint with a disposable tool. More specific details of portions of the diagrams can be found in earlier embodiments described herein.

In FIGS. 22 and 23 like reference characters are used to identify like parts. In FIG. 22 there is provided an instrument 900 that includes both an elbow joint 905 and a wrist joint 910. These joints allow for orthogonal motions of the various segments about respective axes 905A and 910A. Both of these joints are driven by cabling in a manner as described earlier, such as in the pivot arrangement shown in FIGS. 3 and 4. This cabling preferably runs through the center of the instrument as previously described. The instrument 900 also includes an end tool 920 driven from a cable or rod 925. This tool construction and its actuation element may be the same as described in FIGS. 14-17, and would include separate interengagable/disengagable portions as previously described.

In FIG. 23 there is shown an instrument 930 that includes only a single wrist joint 910, along with the tool 920 actuated by means of the actuation element 925. Again tool 920 is preferably readily detachable in the manner shown in FIGS. 14-17 and is thus readily disposable. To provide another degree-of-freedom the instrument may be controllably rotated as indicated by the arrow 927 in FIG. 23.

Figure 24:
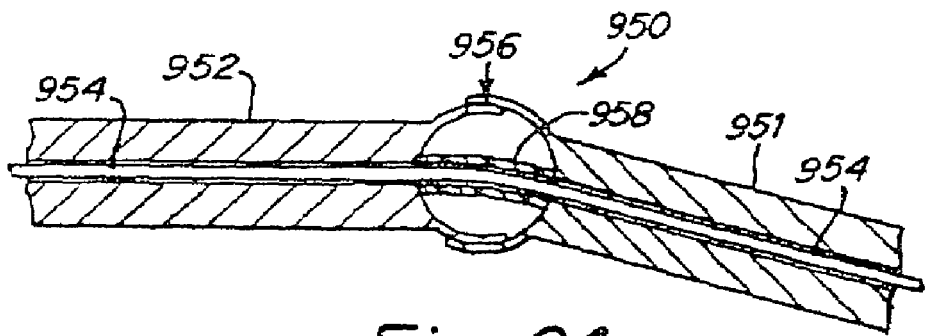
FIG. 24 is a diagram showing further details of a wrist joint useable with a disposable tool.

FIG. 24 illustrates a wrist or other joint that may be used for the joints shown FIGS. 22 and 23. FIG. 24 shows a ball joint 950 with intercoupling sections 951 and 952. An actuation cable 954 is also illustrated extending through sections 951 and 952 as well as through the middle of the joint 950. The joint 950 may be of a conventional type using mating outer pieces at 956 that enable the sections 951 and 952 to have relative rotation therebetween. At least within the joint itself, there is provided a sheath 958 that encloses the cable 954, and that is preferably fixed in position at the top and bottom of the joint. The sheath is flexible and yet sufficiently durable so as to define a fixed length for the cable to extend through, even as the joint is actuated to rotate or pivot.

Appropriate cabling may be provided for control of the joint 950. This type of joint is particularly advantageous in that the center of the joint is open and does not interfere at all with the passing of the actuation cable 954 and sheath 958 through the joint 950. Again, by maintaining the cable at the center of the joint, as illustrated, even as the joint is actuated there is no adverse effect on the actuation cable. In other words as the joint rotates it does not change the length of the cable 954, and thus these separate actions are de-coupled from each other.

Figure 25:
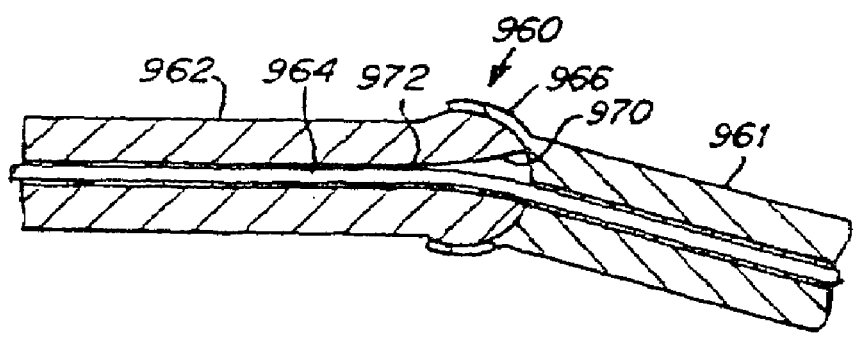
FIG. 25 is a partially cut-away schematic view of another joint construction.

Referring now to FIG. 25, a further description of a wrist or other joint is illustrated that may be used for the joints shown in FIGS. 22 and 23. FIG. 25 shows a ball joint 960 intercoupling sections 961 and 962. An actuation cable 964 is also illustrated extending through sections 961 and 962 as well as through the middle of the joint 960. Here again, the joint 960 may be a conventional joint using mating outer pieces at 966 that enable the sections 961 and 962 to have relative rotation therebetween. Within the joint itself, there may be provided a sheath that encloses the cable 964 and that may be preferably fixed in position at the top and bottom of the joint. Appropriate cabling may be provided for control of the joint 960. In this particular joint rather than being completely open as in FIG. 24 there is provided a funnel like surface illustrated at 970 that directs the cable to an output orifice 972 where the cable is coupled into the section 962. This funnel surface 970 holds the cable such that as the sections experience relative rotation while the length of the cable within the joint is maintained at a fairly fixed length.

Other embodiments of the tool 18 are within the scope of the invention, such as that illustrated in FIGS. 26-33. A set of jaws is illustrated in the figures, but it is understood that other types of tool constructions may also be used with the concepts of the present invention. Also, the instrument shaft may be a rigid shaft, a flexible shaft, or combinations thereof.

The tool 18 includes four basic members including the base 1020, link 1021, upper grip or jaw 1022 and lower grip or jaw 1023. The base 1020 is affixed to the instrument shaft 1010. The instrument shaft 1010 may be rigid or flexible depending upon the particular use. If the shaft 1010 is flexible it may be constructed, for example, of a ribbed plastic material. A flexible shaft or section thereof would, in particular, be used in conjunction with a curved guide tube so that the instrument readily bends through the curved adaptor guide tube.

In the embodiment of FIGS. 26-33, link 1021 is rotatably connected to the base 1020 about wrist pivot axis 1025 with a wrist pivot pin at 1026. The upper and lower jaws 1022 and 1023 are rotatably connected to the link 1021 about axis 1028 with a pivot pin 1030, where axis 1028 is essentially perpendicular to axis 1025. The jaws may also be referred to as grippers or graspers.

Six cables 1036-1041 actuate the wrist, namely the link 1021, as well as the end effector or tool 18. Cable 1036 extends through the instrument shaft and through a hole in the base 1020, wraps around curved surface 1032 on link 1021, and then attaches on link 1021 at 1034. Tension on cable 1036 rotates the link 1021, as well as the upper and lower jaws 1022 and 1023, about axis 1025. Cable 1037 provides the opposing action to cable 1036, and goes through the same routing pathway, but on the opposite side of the instrument shaft. Cable 1037 is also attached to link 1021 generally at 1034.

Cables 1038 and 1040 also travel through the instrument shaft 1030 and though holes in the base 1020. The cables 1038 and 1040 then pass between two fixed posts 1035. These posts constrain the cables to pass substantially through the axis 1025 about which the link 1021 rotates. This construction allows the link 1021 to rotate freely with minimal length changes in cables 1038-1041. In other words, the cables 1038-1041, which actuate the jaws 1022 and 1023, are essentially decoupled from the motion of link 1021. Cables 1038 and 1040 pass over rounded sections and terminate on jaws 1022 and 1023, respectively. The application of tension on cables 1038 and 1040 rotate jaws 1022 and 1023 counterclockwise about axis 1028.

Figures 26, 27A:
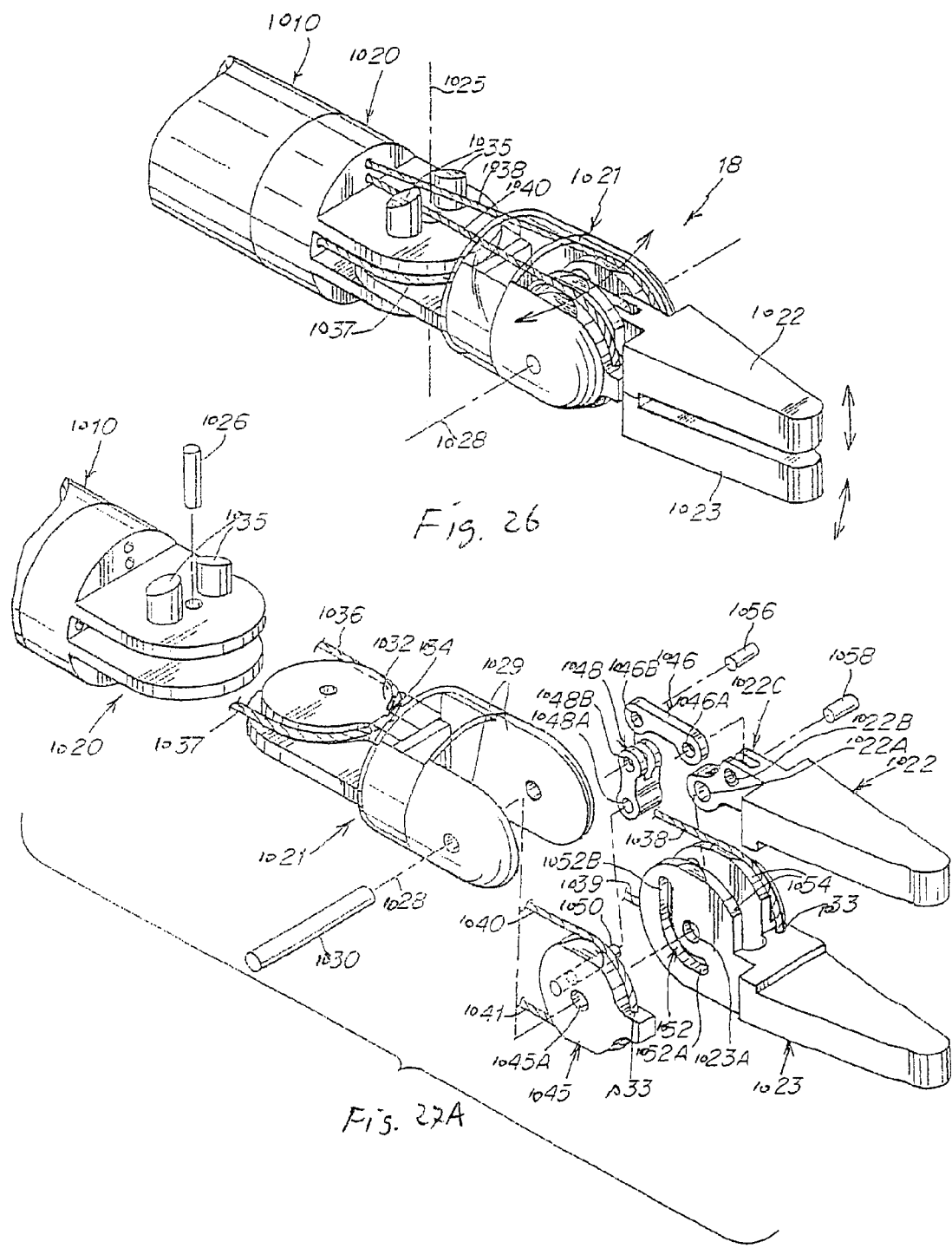
FIG. 26 is a perspective view of a another embodiment of a tool.
FIG. 27A is an exploded perspective view of the tool of FIG. 26 illustrating separate components thereof.

Finally, as shown in FIG. 27A, the cables 1039 and 1041 pass through the same routing pathway as cables 1038 and 1040, but on the opposite side of the instrument. These cables 1039 and 1041 provide the clockwise motion to grips or jaws 1022 and 1023, respectively. The ends of cables 1038-1041 may be secured at 1033 of the jaws 1022 and 1023.

In addition to the jaws 1022 and 1023, the tool 18 includes a rotation piece 1045, a linkage 1046 and slotted linkage 1048. The rotation piece 1045 has a centrally disposed hole 1045A that is adapted to receive the pivot pin 1030. The pivot pin 1030 also passes through holes 1023A in one jaw member and holes 1022A in the other jaw member. The pin 1030 is secured in respective holes in the arms 1029 of the link 1021 in a well-known manner to rotatably support the jaw members from the link 1021. The rotation piece 1045 also carries an actuation pin 1050 extending in the same direction as the pivot pin 1030, and parallel thereto. The actuation pin 1050 extends into curved J-shaped slots 1052 in respective jaw flanges 1054 of jaw 1023.

Figure 30:
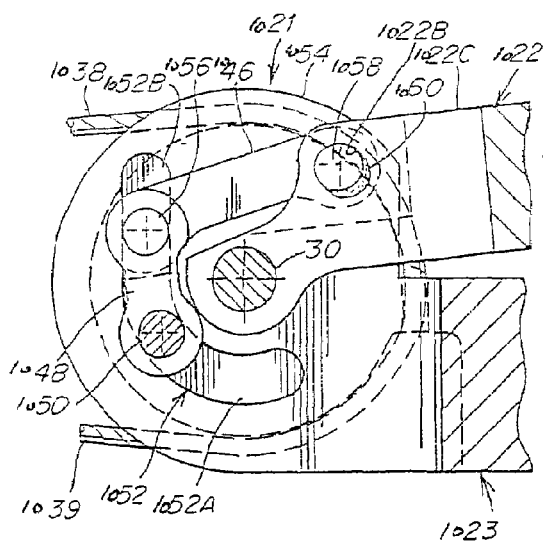
FIG. 30 is a cross-sectional view as taken along line 30-30 of FIG. 29 showing the tool of the present invention with the jaws in a partially open position.
Figure 31:
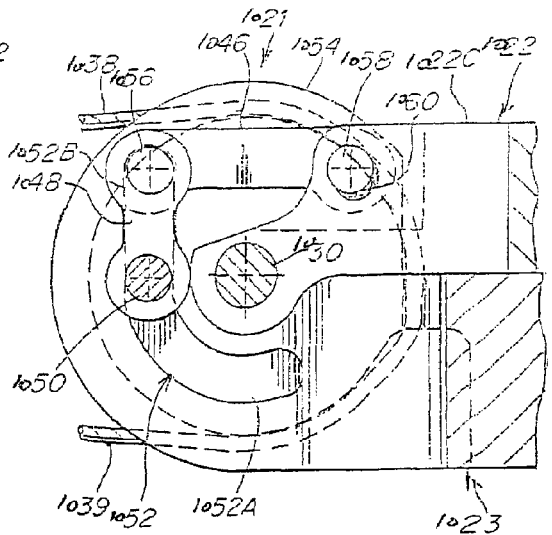
FIG. 31 is a cross-sectional view like that illustrated in FIG. 30 but with the jaws in a fully closed position.

The actuation pin 1050 is also received by the linkage 1048 through the end hole 1048A, and the linkage is supported between the spaced flanges 1054 of the jaw 1023. At the slotted end of the linkage 1048 there is a set of holes 1048B that receive the pin 1056. The linkage 1048 also pivotally attaches with the linkage 1046 by virtue of the pin 1056 passing through the holes 1046B and 1048B. The pin 1056 is also positioned in the slots 1052 of the flanges 1054, and thus moves along the slots to different positions, two of which are illustrated in FIGS. 30 and 31. When the jaws are fully closed, the pin 1056 is at the very top of the slot 1052 as illustrated in FIG. 31. FIG. 30 shows the pin 1056 in a lower position which occurs when the jaws are partially opened. The pin 1050 likewise is in different positions in the slot 52 depending upon the position of the jaws.

Figure 32:
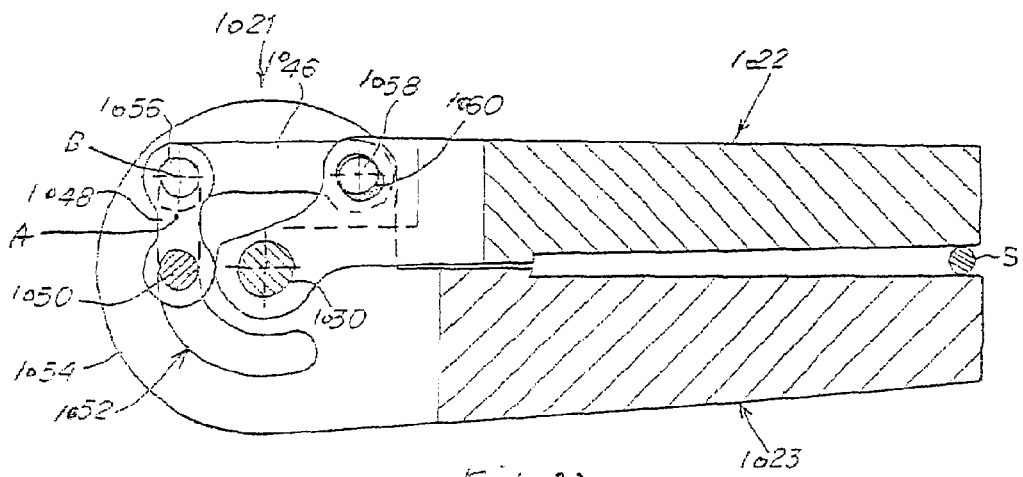
FIG. 32 is a somewhat schematic cross-sectional view of the first embodiment of the tool with the resilient pad partially compressed in grasping a small diameter item such as a thread or suture.
Figure 33:
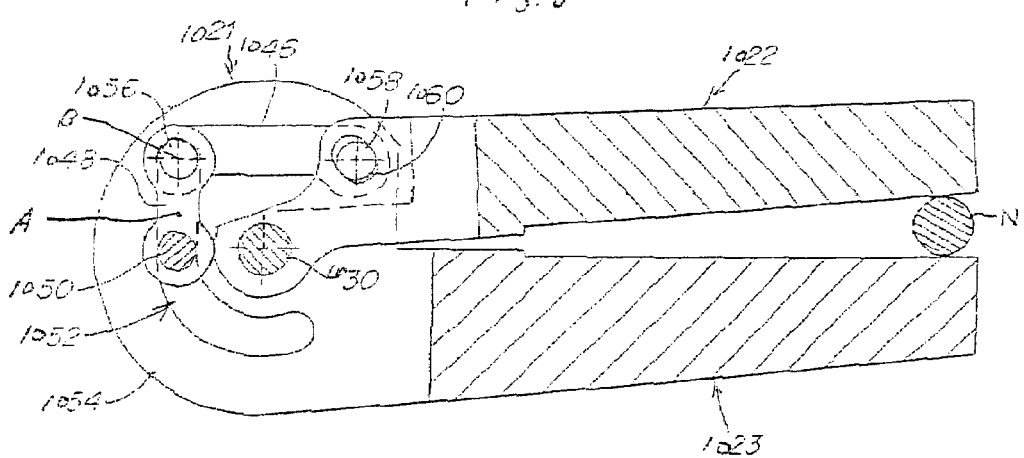
FIG. 33 is a somewhat schematic cross-sectional view of the first embodiment of the tool with the resilient pad essentially fully compressed in grasping a larger diameter item such as a needle.

The linkage 1046 is also supported at its other end at hole 1046A by the pin 1058. The pin 1058 also passes through a set of holes 1022B in the base of the jaw 1022. The linkage 1046 fits in a slot at the base of the jaw 1022, and the pin 1058 passes through both the base of the jaw 1022 as well as the linkage 1046. The pin 1058 also preferably has a compliant member such as a set of resilient members disposed about at least a portion thereof, as illustrated in FIGS. 30 and 31, at 1060, in an uncompressed position. FIG. 31 shows the resilient cups 1060 uncompressed, while FIG. 32 shows the resilient cups partially compressed when the jaws are grasping a small diameter member such as a suture S. FIG. 33 shows the cups 1060 essentially fully compressed, when the jaws are grasping a larger diameter member such as a needle N. The cups 1060 may fit about the pin 1058, and be disposed in the base of the jaw 1022. The holes 1022B that receive the cups 1060 are of somewhat elongated shape, such as illustrated in FIGS. 27B, 27C, 30, and 31.

With further reference to FIGS. 32 and 33, the jaws 1022 and 1023 apply a smaller but sufficient force to hold a smaller diameter item, such as the suture S than when holding a larger item such as a needle N. This force is primarily a function of the resiliency of the cups 1060. Thus, the larger the diameter of the item being held, the larger the corresponding holding force. The tool is constructed so that when the jaws are holding an item the size of a needle N the cups 1060 are essentially fully compressed, and a maximum grasping force is applied to the needle N. This is particularly desirable for important surgery techniques for the securing and controlling of the needle. When the jaws 1022 and 1023 first make contact with an item positioned between them, the pin 1056 is in a contact position A' (FIG. 33) for a larger item such as the needle N, or further up the slot 1052 at a position A (FIG. 32) for a smaller item such as the suture S. When a sufficient force is applied to the item with the jaws, the pin 1056 moves to a locked position B (FIGS. 32 and 33), regardless of the size of the item being grasped.

Figure 27B:
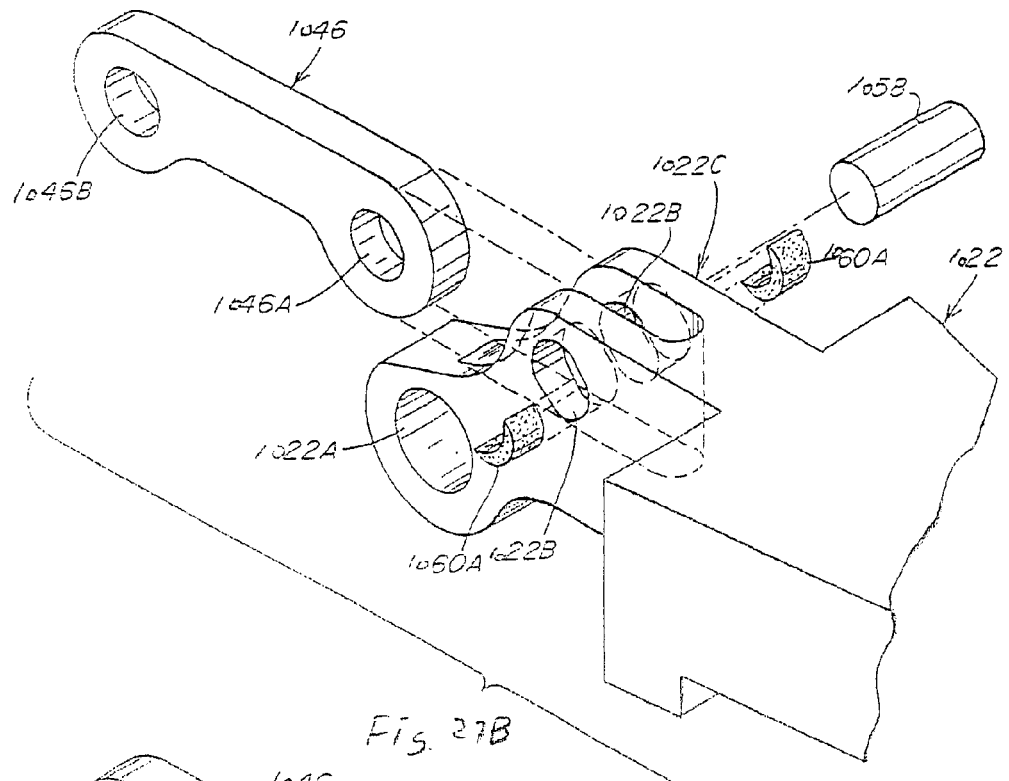
FIG. 27B is an exploded fragmentary view of one form of resilient member used in the embodiment of FIG. 27A.
Figure 27C:
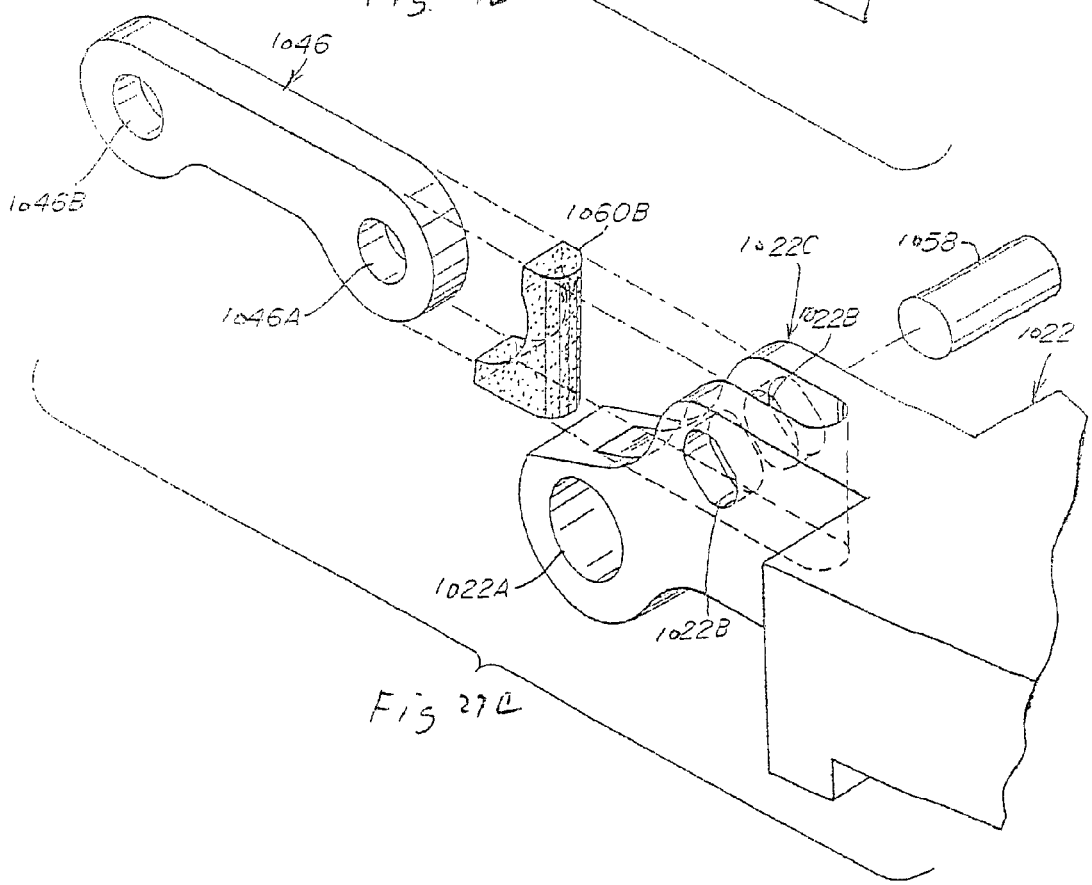
FIG. 27C is an exploded fragmentary view of another form of resilient member used in the embodiment of FIG. 27A.
Figure 28:
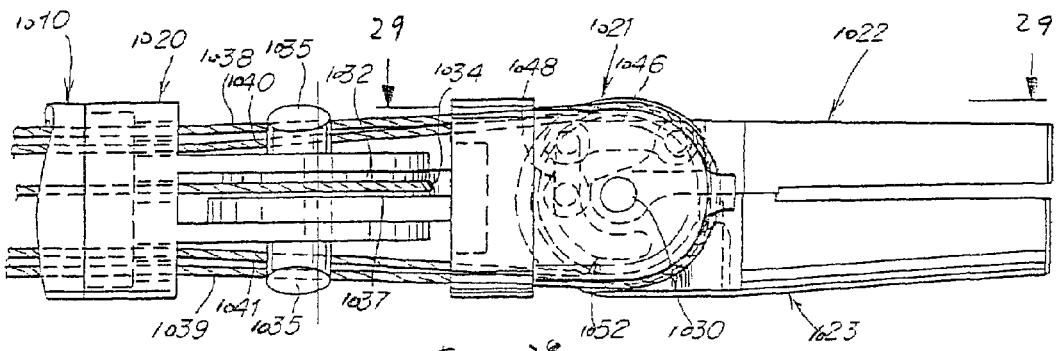
FIG. 28 is a side elevation view of the tool depicted in FIGS. 26 and 27A.
Figure 29:
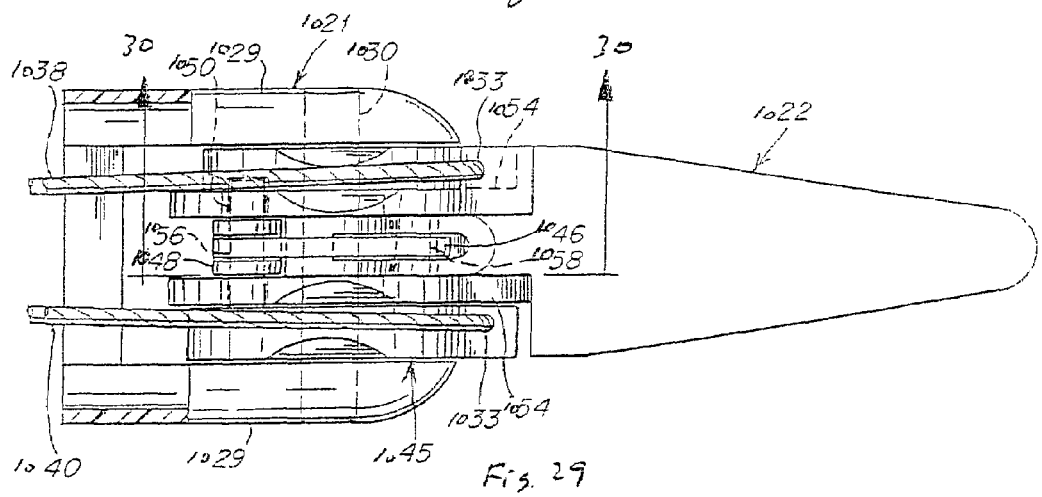
FIG. 29 is an enlarged partial top plan view as seen along line 29-29 of FIG. 28 and illustrating further details of the tool.

Other embodiments of the resilient members are shown in the fragmentary exploded views of FIGS. 27B and 27C. The embodiment of FIG. 27B uses a pair of cups 1060A, while the embodiment of FIG. 27C uses only a single cup. In FIGS. 27B and 27C the same reference characters are used as in FIG. 27A to identify like components. In the embodiment of FIG. 27B the cups 1060A are positioned within respective holes 1022B. They may be positioned with the use of an adhesive. The cups 1060A are thus be located at opposite ends of the pin 1058. When the jaws are in the closed position, these cups 1060A are compressed as the pin 1058 rides downwardly in the somewhat elongated hole or slot 1022B. In the embodiment of FIG. 27C the single cup 1060B is of somewhat larger shape than the cups 1060A and is located between the spaced walls of the base 1022C. The link 1046 is positioned between these walls, as is the cup 1060B. The cup 1060B may also be secured in position by an adhesive. The cup 1060B is engaged by the end of the link 1046. In this embodiment the pin 1058 also rides within the elongated slots 1022B and when the jaws are moved to a closed position the end of link 1046 bears against the cup 1060B. In still another embodiment one may use all three cups to provide additional resiliency.

The actuation cables for the end effector include the cables 1038-1041. One set of cables actuates the rotation piece 1045, while the other set of cables actuates the jaw 1023. The other jaw 1022 is actuated through the coupling provided from the rotation piece 1045 to the jaw 1022, including pin 1050 and the associated linkages 1046 and 1048 controlled via pins riding in slots 1052. These linkages provide direct drive from the rotation piece 1045 to the base of the jaw 1022, to control the pivoting motion of that jaw, controlled usually from a remote location.

Figure 34:
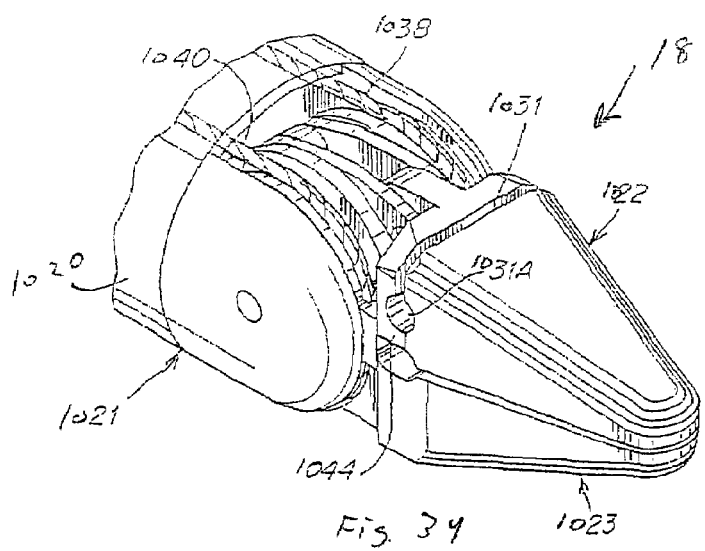
FIG. 34 is a perspective view of a second embodiment of the invention employing a flexure gap in one of the jaws.
Figure 35:
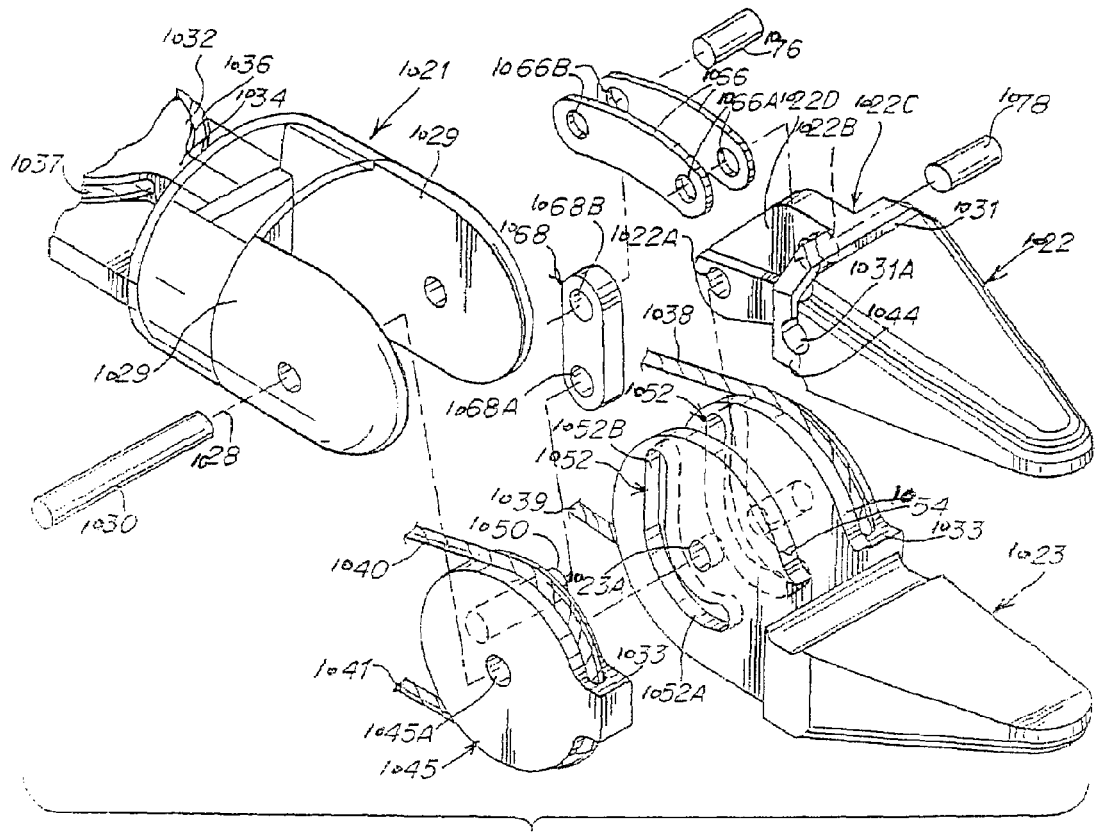
FIG. 35 is an exploded perspective view of the tool of this second embodiment of the invention.
Figure 36:
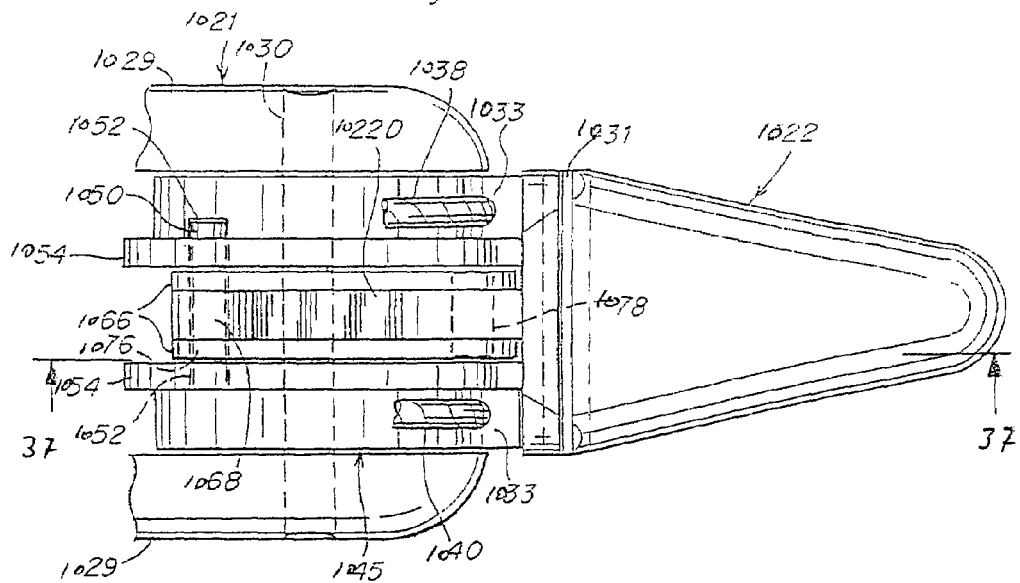
FIG. 36 is a plan view of the tool of FIGS. 34 and 35.

Another embodiment of the tool 18 is illustrated in FIGS. 34-38, where FIG. 34 is a perspective view of the tool while FIG. 35 is an exploded perspective view showing the separate components of the tool. In this embodiment the same reference characters are used to designate similar components.

The tool 18 shown in FIGS. 34-38 includes four basic members including a base 1020, a link 1021 attached to the base, an upper grip or jaw 1022, and a lower grip or jaw 1023. The base is affixed to an instrument shaft in a manner similar to that depicted in FIG. 26. As before, the instrument shaft may be rigid or flexible depending upon the particular use.

In the embodiment shown in FIGS. 34-38, the link 1021 may be rotatably connected to the base about a wrist axis such as the axis 1025 of the just previously described embodiment. The upper and lower jaws 1022 and 1023 are rotatably connected to the link 1021 about axis 1028 with a pin 1030 that is substantially perpendicular to axis 1025.

Six cables 1036-1041 actuate the wrist, namely the link 1021, as well as the end effector or tool 18. Cable 1036 extends through the instrument shaft and through a hole in the base, wraps around curved surface 1032 on link 1021, and then attaches on link 1021 at 1034 (FIG. 35). Tension on cable 1036 rotates the link 1021, and the upper and lower jaws 1022 and 1023, about the wrist axis. Cable 1037 provides the opposing action to cable 1036, and goes through the same routing pathway, but on the opposite side of the instrument shaft. Cable 1037 is also attached to link 1021 generally at 1034. Cables 1038 and 1040 also travel through the instrument shaft and though holes in the base. The cables 1038 and 1040 then pass between two fixed posts that are similar to the posts 1035 in FIG. 26. These posts constrain the cables so that they pass substantially through the wrist axis about which the link 1021 rotates. This construction allows the link 1021 to freely rotate with minimal length changes in cables 1038-1041. Hence, the cables 1038-1041, which actuate the jaws 1022 and 1023, are decoupled from the motion of link 1021. Cables 1038 and 1040 pass over rounded sections and terminate on jaws 1022 and 1023, respectively. The application of tension on cables 1038 and 1040 rotate jaws 1022 and 1023 counter-clockwise about axis 1028.

Finally, as shown in FIG. 35, the cables 1039 and 1041 pass through the same routing pathway as cables 1038 and 1040, but on the opposite side of the instrument. These cables 1039 and 1041 provide the clockwise motion to jaws 1022 and 1023, respectively. The ends of cables 1038-1041 are secured at 1033 of the jaws 1022 and 1023.

Figure 37:
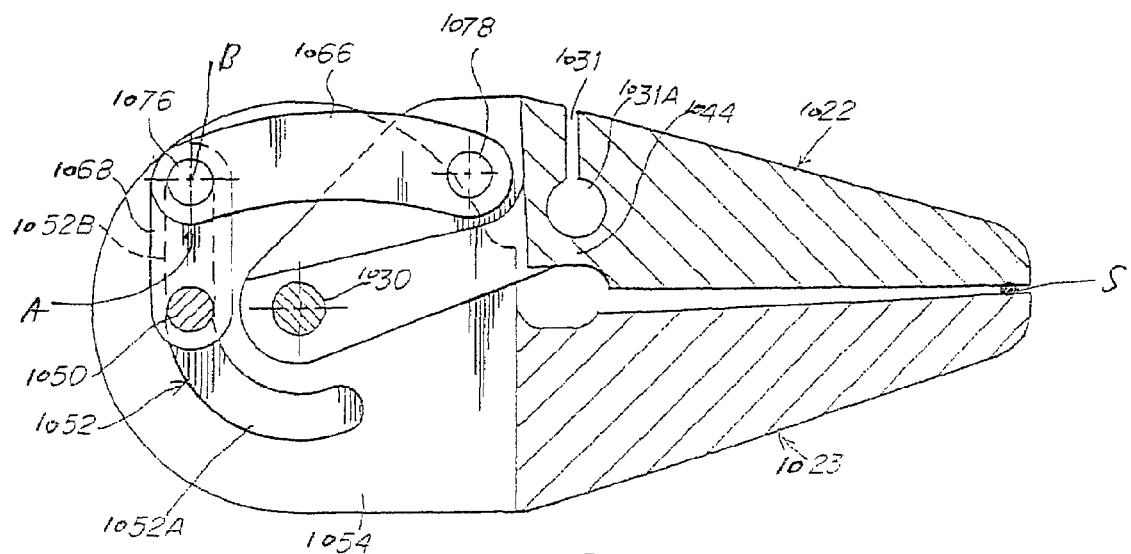
FIG. 37 is a cross-sectional view taken along line 37-37 of FIG. 36 with the jaws having a slight gap at their closed position.
Figure 38:
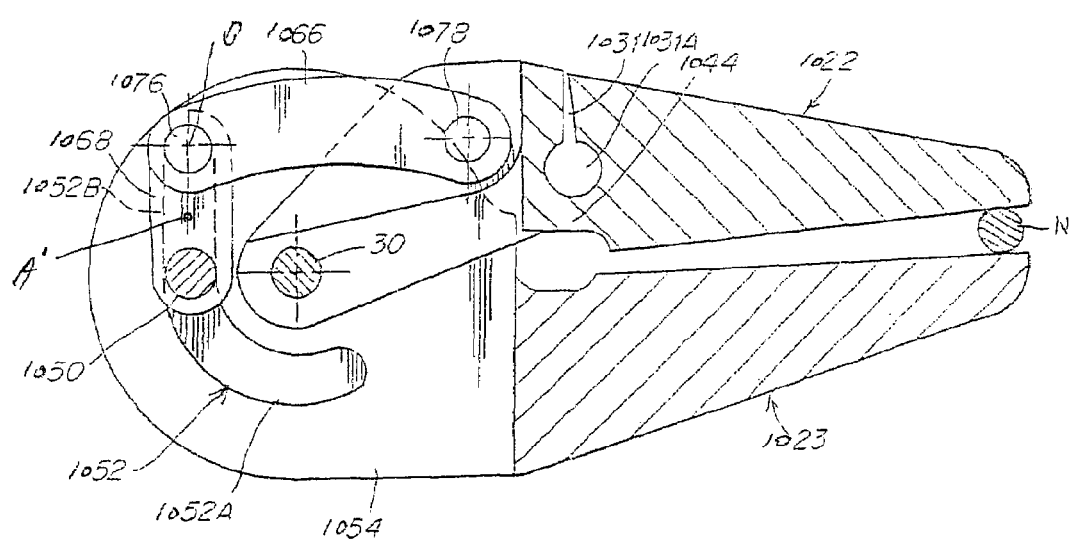
FIG. 38 is a cross-sectional view like that illustrated in FIG. 37 but with the jaws grasping a needle or the like, and with the flexure gap in a substantially closed position.

In addition to the jaws 1022 and 1023, the tool 18 includes the rotation piece 1045, along with linkage pair 1066 and straight linkage 1068. The rotation piece 1045 has a central hole 1045A that receives the pivot pin 1030. The pivot pin 1030 also passes through holes 1023A in one jaw member and hole 1022A in the other jaw member. The pin 1030 is secured to respective holes in the arms 1029 of the link 1021 to rotatably support the jaw members from the link 1021. The rotation piece 1045 also carries an actuation pin 1050 extending in the same direction as the pivot pin 1030, and parallel thereto. The actuation pin 1050 extends into curved slots 1052 in respective jaw flanges 1054 of jaw 1023, as shown in FIGS. 35, 37, and 38.

The actuation pin 1050 is also received through an end hole 1068A of the linkage 1068, and the linkage is supported between the spaced flanges 1054 of the jaw 1023. At the other end of the linkage 1068 there is a hole 1068B that receives the pin 1076. The linkage 1068 also pivotally attaches with the linkage pair 1066 by virtue of the pin 1076 passing through the holes 1066B and 1068B. The pin 1076 is also positioned in the slots 1052 of the flanges 1054, and thus moves along the slots to different positions, two of which are illustrated in FIGS. 37 and 38. When the jaws are in a substantially closed position, the pin 1076 is at the top of the slot 1052 as illustrated in FIG. 37. When the jaws are in other positions, the pin 1050 will reside in different positions in the slot 1052.

The linkages 1066 are also supported at its other ends at holes 1066A the pin 1078. The pin 1078 also passes through a hole 1022B in the base of the jaw 1022. At that point the base has a support wall 1022D in which the hole 1022B is located. The linkage pair 1066 fits on opposite sides of the wall 1022D, and the pin 1078 passes through both the base of the jaw 1022 as well as the linkage pair 1066.

The actuation cables for the end effector or tool include the cables 1038-1041. One set of cables actuates the rotation piece 1045, while the other set of cables actuates the jaw 1023. The other jaw 1022 is actuated through the coupling provided from the rotation piece 1045 to the jaw 1022, including pin 1050 and the associated linkages 1046 and 1048 riding in slots 1052. These linkages provide direct drive from the rotation piece 1045 to the base of the jaw 1022, to control the pivoting motion of that jaw, typically from a remote location.

In the embodiment shown in FIGS. 35-38, control of the grasping force on an item is provided primarily by means of a slot or gap in one of the jaws. This is illustrated in FIGS. 34-38 by the gap 1031 located near the base 1022C in the jaw 1022. FIGS. 35, 37, and 38 show in particular the shape and depth of the gap 1031. The gap 1031 is located above a hinge 1044 where the jaw can deflect when grasping and holding an item, regardless of its size, and with a firm grasping force. The gap 1031 may be terminated in a tubular passage 1031 A to enhance the hinging effect of the hinge 1044. Hence the hinge 1044 acts as a compliance member similar to the resilient members 1060 described with reference to FIGS. 27-33.

Referring now in particular to FIGS. 37 and 38, the jaws 1022, 1023 are shown in a substantially closed position in FIG. 37 grasping a suture S. In that position it is noted that both of the pins 1050 and 1076 are substantially at their top transition locations. FIG. 38 illustrates the jaws 1022, 1023 grasping an item such as a needle N that causes the jaw 1022 to flex and consequently the gap 31 to close up. This flexure enables the application of a varied grasping force at the tip of the jaws. When the links are at the end of their travel, the jaw 1022 flexes when the jaws 1022, 1023 grasp an item. The amount of flexure depends on the diameter of the item being grasped. Thus, the jaws 1022 flexes to a lesser extent when a smaller diameter item such as a suture S is being grasped then when a larger item such as a needle N is being held. That is, to grasp a smaller item, the gap 1031 closes to a lesser extent, while the jaws still apply a sufficient holding force to the item. This force is primarily a function of the resiliency at the gap, as defined primarily by the flexure capability at the hinge 1044. The larger the diameter of the item being held, the larger the corresponding holding force. The tool is constructed so that, for an item the size of a needle, as shown in FIG. 38, the gap 1031 is fully closed with the sides of the top of the gap touching, with a maximum grasping force being applied to the needle N. This is particularly desirable for the securing and controlling of the needle in important surgery techniques. Here again, the pin 1076 is at a contact position A' (FIG. 38) when the jaws first make contact with a larger item such as the needle N, or further up the slot 1052 at a contact position A (FIG. 37) when the jaws contact a smaller item such as the suture S. Regardless of the size of the item, the pin moves to a locked position B (FIGS. 37 and 38) when the sufficient force is applied to lock the jaws onto the item.

In connection with both of the embodiments described in respective FIG. 26-33, and FIGS. 34-38, there has been described a "locked" position B of the pins or jaws. This locked position corresponds to a position wherein the linkages are disposed at right angles to each other. In other words, for example, in FIG. 31 in that locked position the linkages 1046 and 1048 are disposed at right angles (90 degrees) to each other. This provides virtually infinite grasping force with essentially no back drive at the jaws. Regarding the embodiment in FIGS. 34-38 it would be the linkages 1066 and 1068 that are disposed at right angles when locked.

Figure 39:
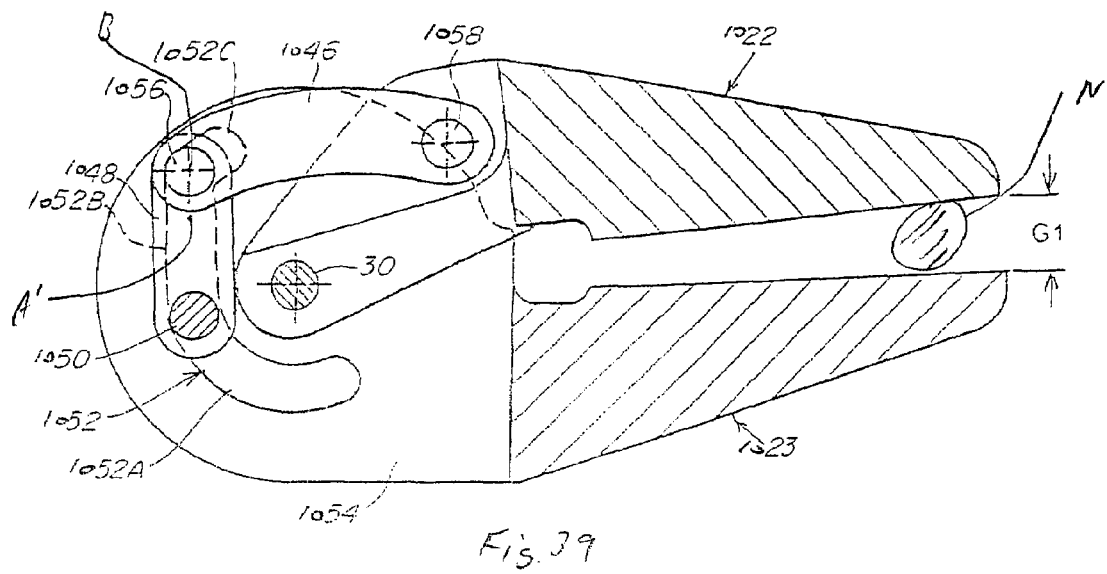
FIG. 39 is a cross-sectional view similar to that depicted in FIGS. 37 and 38, and of yet another embodiment of the invention illustrating the tool in a partially open position.
Figure 40:
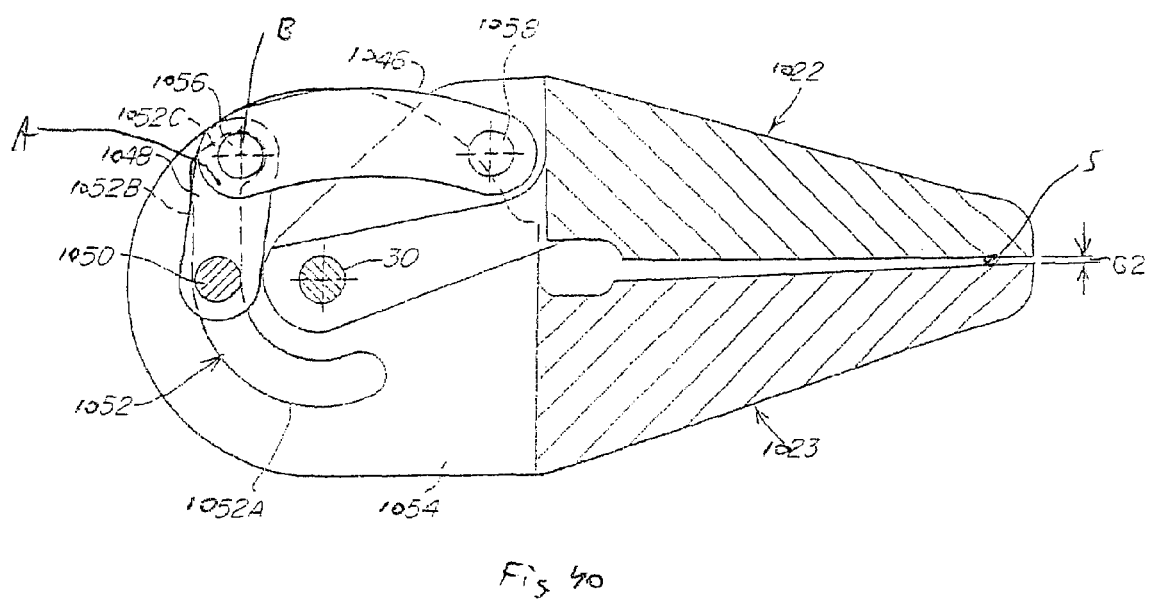
FIG. 40 is a cross-sectional view the same as that depicted in the embodiment of FIG. 39 but with the jaws in a more closed position.

Reference is now made to another embodiment of the invention illustrated in FIGS. 39 and 40. This embodiment has a structure very similar to that described in detail in FIGS. 26-33. However, in place of the resilient cup 1060 there is provided a modified jaw slot configuration. As indicated previously the slots 1052 in jaw 1023 have a curved segment 1052A, and a straight segment 1052B. In this embodiment the J-slots 1052 also have a contiguous end slot 1052C that extends back toward the tip of the jaw tip. Hence, the overall slot configuration is C-shaped. In FIG. 39 the jaws are in a substantially open position with a gap GI as noted when the jaw members 1022, 1023 are locked onto and the needle N, with the pin 1056 located at a locked position B. Before the jaws make contact with the needle N, the pin 1056 may be out of the end slot 1052C, and the pins 1050 and 1056 are located at different positions along the slots 1052 depending upon the degree of openness of the jaws. When the jaws contact the needle N, the pin 1056 is at a contact position A'. In FIG. 40 the jaws are in a substantially closed position with a small gap G2 as the jaws grasp a smaller item such as a suture S. In this position the pin 1056 now moves further into the end slots 1052C to the locked position B, as the jaws apply a grasping force to an item to lock the suture between the jaws. When contact is first made between the jaws and the suture, the pin 1056 is located at the contact position A further up the slot 1052 than the contact position A' of FIG. 39. Thus, depending upon the size thereof, the pin 1056 moves to a greater or lesser extent into the slots 1052C.

To hold a large diameter item such as a needle, the pins 1050 and 1056 are in the position illustrated in FIG. 39 with there being a maximum grasping force applied to the item by virtue of the links 1046 and 1048 being positioned at 90 degrees relative to each other. For smaller diameter items such as a suture, the pins rotate slightly further clockwise with the pin 1056 moving into the slot 1052C as illustrated in FIG. 40. When the pin 1056 moves into the slot 1052C, the jaw and linkages move together as a rigid body while closing against the suture.

In sum the slots 1052C, like the resilient member 1060 (FIGS. 27-33) and the hinge 1044 (FIGS. 37 and 38), are accommodating mechanisms that allow a closing force to be applied to grasped items of different sizes as the force is applied to the grasped item as the jaws close to a position at which the jaws remain open.

The accommodating mechanisms described above like the slots 1052C (FIGS. 39 and 40), the resilient member 1060 (FIGS. 27-33), and the hinge 1044 (FIGS. 37 and 38, can be implemented in other types of grasping mechanisms as well, such as those described in U.S. application Ser. No. 09/827,643, filed Apr. 6, 2001, and U.S. application Ser. No. 10/014,143, filed Nov. 16, 2001, the entire contents of which are incorporated herein by reference.

In each of the aforementioned embodiments described herein the medical instrument includes a jaw or work members controlled by a drive mechanism that is used to open and close the jaws or work members for applying an increased force to an item grasped between the jaws or work members. The accommodating mechanisms described above such as the slots 1052C (FIGS. 39 and 40), the resilient member 1060 (FIGS. 27-33), and the hinge 1044 (FIGS. 37 and 38, each have the characteristic of providing a maximum grasping force at what may be considered a maximum grasping position. This corresponds to the positions illustrated, and discussed previously, in FIGS. 33, 38, and 39. In each of the embodiments the instrument is constructed so that this maximum position corresponds to a predetermined size or diameter item that is to be grasped, usually a needle in this case. For item smaller or larger than this size the grasping force is progressively less. In the instance of the embodiment of FIGS. 26-33, for smaller items such as the suture S, the force is less because the compliant member is compressed less. For the case of an item larger than the needle N, the linkage does not go to the top of the J-slot and thus the applied force is also less in that case, as the linkages are not yet to a maximum force 90 degree position.

In all three of the described embodiments the accommodating mechanism allows the jaws or work members to be closed beyond this maximum grasping position in order to grasp items of various sizes, particularly smaller size items.

Again, this is illustrated by way of example in FIG. 32 where the jaws go past their maximum grasping position, closing to a closer position therebetween, in grasping the suture S. In FIG. 37 this is illustrated by the jaws closing to grasp the suture S with less force being imposed by the flexure at the jaw 1022. This is also illustrated in FIGS. 39 and 40. In FIG. 39 the jaws are at their maximum grasping position. In FIG. 40 the jaws are closed beyond this maximum grasping position to grasp the smaller size suture S. The accommodating mechanism in this case may be considered as including the slot segment 1052C that enables further rotation of the linkages to the position illustrated in FIG. 40.

Other embodiments of the flexible or bending segment are within the scope of the invention. For example, there is shown in FIGS. 41-47 another embodiment of a flexible or bending segment with a unibody construction which can be used with any suitable end effector like the tools 18 described above, whether used with a rigid shaft body or a flexible shaft body or combinations thereof. As with some of the embodiments described earlier, one of the benefits of the embodiment shown in FIGS. 41-47 is that only a single cable 1136 needs to be coupled to the tool 18 to actuate it. The pitch and yaw of the tool 18 is controlled at the flexible section 1100 shown in FIG. 41. This arrangement also lends itself to making the tool disposable or at the very least detachable from the instrument body to facilitate substituting another tool. Here again, because of the simplified construction at the tip of the instrument, a tool can be constructed that is readily detachable from the instrument.

Although the bendable section 1100 is depicted near the tool, the bendable section can be located at other locations further away from the tool. Since the tool 18 of the embodiment shown in FIGS. 41-47 requires only a single actuation cable, it is simpler to operate than the wrist/tool combination shown in FIGS. 26 and 27. Recall, in the wrist arrangement, a pivot axis does not accommodate single cable actuation. Thus, with the wrist unit one has to use a far more complex cabling scheme, such as, by way of example, the cabling arrangement illustrated in U.S. Pat. Nos. 6,312,435 and 6,206,903. Furthermore, the single cable actuation provides a more simplified design that readily lends itself to a variety of tool constructions.

In order for the various degrees of motions to be decoupled from each other, and for the proper overall functioning of the distal end of the instrument, the instrument has certain preferred characteristics, particularly at the flexible or bendable section of the instrument shaft. These characteristics are listed below but are not in any particular order of significance. Embodiments can employ at least one of these characteristics. Furthermore, although these characteristics are listed with reference to the embodiment described in FIGS. 41-44, one or more of the characteristics can apply as well to any of the other embodiments described earlier.

A first characteristic is that the actuation element for the tool be centered in the flexible or bendable section. In this way, during any bending operation the center of the flexible or bendable section tends to maintain the same length, even though opposed outer surfaces of the section may, respectively, expand and contract. This, in essence, means that the bending action is not erroneously transferred to the actuation element for the tool, hence, de-coupling the bending operation from the tool actuation, and vice versa.

Figure 45:
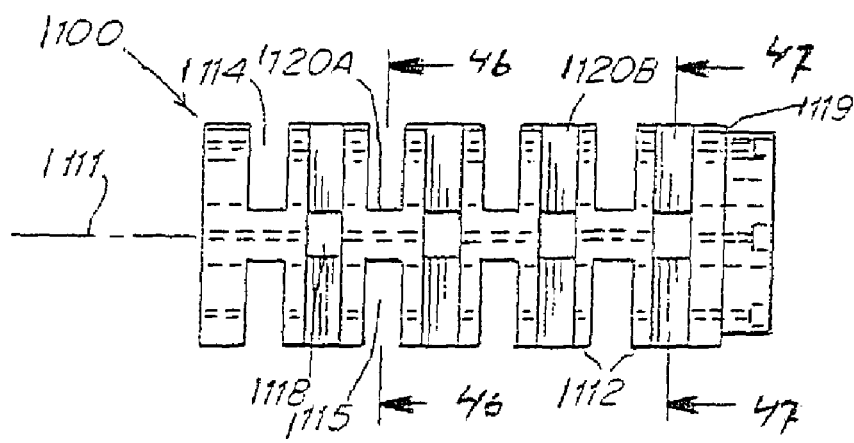
FIG. 45 is a side elevation view of the flexible or bendable section itself.

A second characteristic is that the flexible or bendable section of the instrument shaft be readily flexible without the application of undue force. This bendable section, in a preferred embodiment, is to have orthogonal bending characteristics, hence providing two degrees of freedom (DOF) to the distal tool, for example, yaw and pitch. To accomplish this, at a particular bend location, a substantial portion of the flexible or bendable section is located as near to the center neutral axis 1111 of the section as physically possible. This is achieved by the spaced rib construction including the ribs 1112 shown in the drawings. The slots 1114 defined by these ribs 1112 provide void areas, leaving more material near the center neutral axis, as depicted in FIG. 45. Reference has been made to a neutral axis 1111 of the bendable section 1100. In actuality there is for a particular bend direction a neutral plane that during a bend is maintained at a fixed length.

A third characteristic relates to the torsional nature of the flexible or bendable section. The more stiff the section is torsionally (twisting moment) the less likely there will be an undesired twisting of the bendable section that accompanies controlled rotation thereof. In other words, if the bendable section is torsionally stiff, then upon controlled rotation of the instrument shaft, there is no an undesired twisting action imparted on the shaft particularly at the flexible or bendable section 1100. To accomplish this, at a particular bend location, a substantial portion of the material forming the flexible or bendable section is located at the periphery of the flexible or bendable section. This may be achieved by having portions of the section extend to an outer surface. In the embodiment described here this is accomplished by providing radial ridges, such as the ridges 1120 shown in the drawings. Furthermore, these ridges are alternated between horizontal and vertical positions to, at the same time, to provide the orthogonal bending or flexing.

A fourth characteristic is that the flexible or bendable section of the instrument shaft is constructed so that there is little or no end-to-end compression. In other words, the flexible or bendable section maintains a relatively constant length regardless of the motion actuations that occur in the multiple degrees of freedom movement of the instrument. To accomplish this, a stiff member is provided to maintain the ends of the flexible or bendable section at a fixed spacing. This may be achieved by providing the stiff member as a centrally located stiff sleeve that receives and supports the sliding motion of the actuation element for operation of the distal tool. This stiff member is preferably fixed at its opposite ends to the bendable section to maintain the fixed length of the section, thereby preventing end-to-end compression. At least part of this member may include the sleeve 1182 depicted in FIG. 43.

Referring again to FIG. 41 there is disclosed one embodiment of the tool 18, used in conjunction with a flexible shaft or tube having a remotely controllable bending or flexing section 1100. The medical instrument may include an elongated shaft, such as shaft section 1110 shown in FIGS. 41 and 42, having proximal and distal ends; and the tool 18 with jaws 102 and 104, supported from the distal end of the elongated shaft and useable in performing a medical procedure on a subject. In FIGS. 42 and 43 the tool 18 is actuated preferably by a single tendon or cable 1136 that extends through the flexible section 1100. In order to provide the pitch and yaw action at the tool, the bending or flexing section 1100 is constructed to bend in orthogonal directions with the use of four cables separated at about 90° intervals and by using a center support with ribs and slots about the entire periphery of the bending section 1100, as depicted in FIGS. 42-44. This orthogonal bending may also be referred to as bi-axial bending, meaning bending in separate axes. The ribs 1112 define corresponding slots 1114, and also define at each of their centers a center support passage 1118 that has the cable 1136 extending through it, as well as other cable support members described in further detail later. The bending section 1100 extends from the end of tube section 1110, which itself may be flexible, may be smooth as shown, or may be fluted, and may have other controllable bending sections disposed along its length.

To bend the bending section 1100 in orthogonal directions, use is made of the four cables 1106, 1107, 1116 and 1117. The operation of cables 1106 and 1107 provides flexing in one degree-of-freedom while an added orthogonal degree-of-freedom is provided by operation of cables 1116 and 1117. Each of the cables 1106, 1107, 1116, and 1117 have at their terminating ends respective balls 1106A, 1107A, 1116A, and 1117A that may be held in corresponding recesses in a distal end wall 1119 (FIG. 45) of the flexible section 1100.

The bending section 1100, as indicated previously, includes a series of spaced ribs 1112 positioned, in parallel, with the plane of each rib extending orthogonal to the neutral axis 1111 of the section 1100. At the proximal end of the bendable section, an end rib connects to the shaft section 1110, while at the distal end there is provided the distal end wall 1119 that supports the ends of the cables. Each of the ribs 1112 are held in spaced relationship by means of the alternating ridges 1120. As depicted in FIG. 43 these ridges are identified as horizontal ridges 1120A, alternating with vertical ridges 1120B. This structure provides support at the center passage for the actuating cable 1136, while also providing torsional strength to prevent undesired twisting at the shaft section 1100.

The jaws 1102 and 1104 are supported for opening and closing by means of a pivot pin 1135 that extends along a pivot axis. These grippers may be supported in link 1140, and the pin 1135 may be supported at its ends in opposite sides of link 1140. The tool also includes a pivot linkage 1142 that intercouples between the grippers and the actuation cable 1136. The pivot linkage 1142 includes linkages 1142A and 1142B. At one end, each of the linkages 1142A and 1142B connects to respective jaws 1104 and 1102. At the other end, the linkages 1142A and 1142B are pivotally supported at end 1137 of cable 1136. Opposed pins extend from end 1137 for engagement with the linkages 1142A and 1142B. The jaws 1102 and 1104 are shown having recesses 1102A and 1104A for accommodating the respective linkages 1142B and 1142A.

In FIG. 42 the jaws 1102 and 1104 are shown in their open position with the linkages 1142A and 1142B shown in a forward pivoted configuration. FIG. 43 illustrates the jaws 1102 and 1104 in a closed position with the linkages 1142A and 1142B shown in an in-line configuration. As the linkage 1142 is moved in an axial direction by the cable 1136, this action opens and closes the jaws or grippers. This corresponds to a "pushing" of the cable in a direction toward the tool. FIG. 43, on the other hand, shows the linkage and grippers in a closed position. This corresponds to a "pulling" of the cable in a direction away from the tool with the specific linkages 1142A and 1142B shown in an in-line configuration in their final closed position. The grippers themselves are prevented from any axial movement by the support at pin 1135, so when the linkage is operated from the cable 1136 the resulting action is either opening or closing of the grippers, depending upon the direction of forward-to-back translation of the actuating cable 1136.

The structure shown in FIGS. 41-47 preferably also includes a plastic cable sheath 1180, a plastic stiffener sheath or sleeve 1182 that surrounds the cable 1136 and the sheath 1180, and that fits closely in the center passage 1118, and an outer silicon spacer 1184. The sleeve 1182 is preferably constructed of a polyethylene plastic such as PEEK which has flexibility to allow the sleeve 1182 to bend with the section 1100, but at the same time is sufficiently stiff (particularly end-to-end) to properly retain, center and hold the supported cable to enable the cable to readily slide within the sheath 1180 and the supporting sleeve 1182, in performing its function. In FIG. 42 the sleeve 1182 is illustrated extending from the distal end of the bendable section 1100, back through the passage, to the more proximal end of the bendable section 1100.

Reference has been made previously to the single actuation cable 1136 that provides all the action that is required to operate the tool. This greatly simplifies the construction and makes it easier to keep the single cable centered in the instrument. As indicated previously this centering feature maintains the same length of the actuation element, even though opposed outer surfaces of the section itself may, respectively, expand and contract during bending. This, in essence, means that the bending action is not erroneously transferred to the actuation element, hence, the bending operation is de-coupled from tool actuation, and vice versa.

FIGS. 42 and 43 also show the use of an adhesive, at 1186, such an epoxy adhesive for anchoring opposite ends of the sheath 1180 and the sleeve 1182 to opposite ends of the bendable section 1100. By maintaining the sheath 1180 and sleeve 1182 fixed in position at their ends, when the section 1100 is controlled to bend, the cable length at the center or neutral axis of section 1100 does not change. Furthermore, at the ribbed bendable section, on one side the section shortens and on the other side it expands while keeping the center or neutral axis length unchanged. In this way when bending occurs at section 1100 there is no transfer of motion to the cable 1136 which could undesirably move the jaws. The bending motion is thus de-coupled from the tool operation motion, and vice versa.

Figure 46:
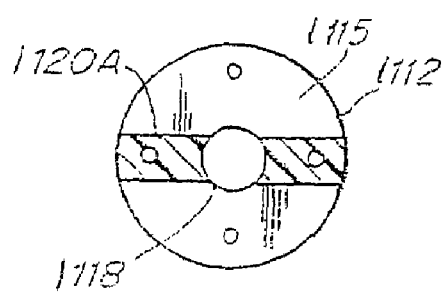
FIG. 46 is a cross-sectional view through the flexible or bendable section as taken along line 46-46 of FIG. 45.
Figure 47:
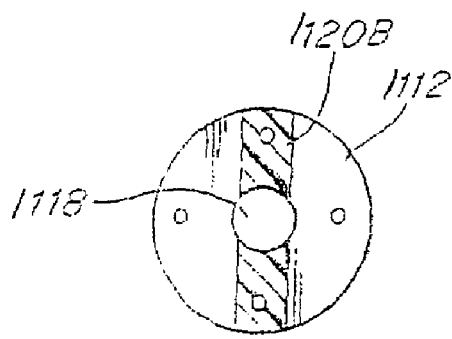
FIG. 47 is a cross-sectional view through the flexible or bendable section as taken along line 47-47 of FIG. 45.

Other features of the bending section are shown in FIG. 45 in a side elevation view, while FIGS. 46 and 47 illustrate cross-sectional views, with one through one of the ridges 1120A and the other through one of the ridges 1120B. The respective ridges 1120A and 1120B are arranged at about 90 degrees to each other.

As described earlier, the section 1100 is easily bendable while being torsionally stiff, and has other improved characteristics as well. Details of these characteristics are best described with reference to FIGS. 45-47 by considering a particular cross-section such as the cross-section in FIG. 45 taken along line 46-46. In viewing FIG. 45 it is clear that, at that location and with the orientation of the section 1100 as shown, there is a substantial void created by the slot 1114, so that the majority of the section material is located at the center of the section. This is consistent with the desired bendability at that location, since, in general, a structure becomes more bendable as its diameter deceases. The void area mentioned is also illustrated in the cross-sectional view of FIG. 46 at 1115.

To understand how the bending section 1100 can be torsionally stiff while also being bendable, reference is also made to the same location at the line 46-46, but with the section rotated through 90 degrees. This is the same as looking at the cross-sectional view depicted in FIG. 47. In other words, one is thus considering the location through the ridge 1120A. The section 1100 is constructed so that there is preferably a relatively large center passage 1118, leaving more material toward the outer periphery, which is desired for providing enhanced torsional stiffness. Note that this material is the material of the ridge itself. Thus, for torsional stiffness it is desired to have a void near the middle and more material located away from the middle.

The rib and ridge arrangement shown in the drawings thus provides in a single structure a bendable section that provides two degrees of freedom (biaxial motion) that is also torsionally stiff. The bending characteristics enable the transfer of two degrees of freedom to the tool, rather than just one degree of freedom as with a conventional wrist joint. The torsional stiffness enables direct rotational transfer to the tool through the bendable section and without any twisting at the bendable section.

Mention has been made previously of the four characteristics of the bendable section described herein. The first characteristic relates to the centering of the actuation element. This is carried out primarily with the use of the center passage and the associated sheath 1180, sleeve 1182, and the spacer 1184. The second characteristic relates to the ease of bending. This is accomplished primarily with the ribbed construction with void peripheral areas. The third characteristic relates to the torsion stiffness that is accomplished primarily by the alternating ridges. Lastly, the fourth characteristic relates to the end-to-end compression. To prevent the bendable section from compressing from end-to-end during an operation, particularly during tool actuation, to facilitate proper tool operation, the center passage is provided with the stiff sleeve 1182, and the opposite ends of the sheath 1180 and sleeve 1182 fixed in place, and the section 1100 has a ridged construction.

It is noted that FIGS. 41-47 disclose one version of an end effector employing jaws 1102 and 1104, in combination with, linkage 1142. However, other tool constructions are also contemplated as falling within the scope of the present invention including ones that provide a mechanical advantage at the tip of the jaws or other work elements.

Also, in various embodiments described herein only a single cable is used for tool actuation. (See, for example, FIGS. 9, 15, and 42.) In these embodiments it is preferable to provide at least the opposite ends of the actuation cables with enhanced stiffness, particularly where the cable is unsupported. For example, in FIG. 42 this might be in the distal section of cable 1136 exiting from wall 1119 to the jaws of the tool. This stiffness can be provided by treating the ends of the cable with a harder metal coating, or by other means that will provide a stiffer end section.

Turning now to FIGS. 48A-48D, there is illustrated yet another embodiment of a flexible section 1660 with a unibody construction. The tool 18 attached to the distal end of the flexible section 1660 includes an upper grip or jaw 1602 and a lower grip or jaw 603, supported from a link 1601. Each of the jaws 1602, 1603, as well as the link 1601, may be constructed of metal, or alternatively, the link 1601 may be constructed of a hard plastic. The link 1601 is engaged with the distal end of the flexible stem section 1302. FIG. 48C shows the distal end of the stem section 1302, terminating in a bending or flexing section 1660. Also, at the flexible section 1660, flexing and bending is enhanced by the arrangement of diametrically-disposed slots 1662 that define ribs 1664 between the slots. The flexible section 1660 also has a longitudinally extending wall 1665, through which cabling extends, particularly for the operation of the tool jaws. The wall 1665 can also be thought of as opposed ridges that extend outward from the center of the flexible section 1660. The very distal end of the bending section 1660 terminates with an opening 1666 for receiving the end 1668 of the link 1601. The cabling 1608-1611 is preferably at the center of the flex section at wall 1665 to effectively decouple flex or bending motions from tool motions.

To operate the tool, reference is made to the cables 1608, 1609, 1610, and 1611. All of these cablings extend through the flexible stem section and also through the wall 1665 as illustrated in FIG. 48C. The cables extend to the respective jaws 1602, 1603 for controlling operation thereof in a manner similar to that described previously in connection with FIGS. 5-8. FIGS. 48A-48D also show cables 1606 and 1607 which couple through the bending section 1660 and terminate at ball ends 1606A and 1607A, respectively, and urge against the end of the bendable section in opening 1666. When these cables are pulled individually, they can cause a bending of the wrist at the bending or flexing section 1660. FIG. 48D illustrates the cable 1607 having been pulled in the direction of arrow 1670 so as to flex the section 1660 as depicted in the figure. Pulling on the other cable 1606 causes a bending in the opposite direction.

By virtue of the slots 1662 forming the ribs 1664, there is provided a structure that bends quite easily, while the wall or opposed ridges 1665 provide some torsional rigidity to the flexing section 1660. The wall 1665 bends by compressing at the slots in the manner illustrated in FIG. 48D. This construction eliminates the need for a wrist pin or hinge.

The embodiment illustrated in FIG. 48B has a separate link 1601. However, in an alternate embodiment, this link 1601 may be fabricated integrally with, and as part of, the bending section 1660. For this purpose the link 1601 would then be constructed of a relatively hard plastic rather than the metal link as illustrated in FIG. 48B and would be integral with section 1660.

Mention has also been made of various forms of tools that can be used. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice. Moreover, the bending section itself may be non-actuated. As such, even when the bending movements of the bending section are not controlled by a surgeon, the one or more degrees-of-freedom of movement of the bending section allows it to conform to orifices or lumens within the patient's body as the section is advanced through the body.

There have been described herein a number of different embodiments of bendable sections such as in FIGS. 5, 14, 21, or 41. These may be used, as illustrated herein, in conjunction with instrument systems as described in, for example, FIG. 1 where the instrument is inserted laparoscopically. Alternatively, these concepts may also be used in flexible instrument systems more like that described in FIG. 21 wherein the bendable sections can be located at various positions along the instrument shaft or body. In this case the bendable section or sections may be used both for guidance toward an operative site, such as for guidance through an anatomic lumen or vessel, or for operation or manipulation at an operative site. In the more rigid system where the instrument is meant to enter the body, for example, through an incision, such as laparoscopically, then it is preferred to have the bendable section located close to but just proximal of the distal end effector or tool. This bendable section positioning provides for proper manipulation of the tool at the operative site. In this case the bendable section preferably has a length in a range on the order of ¾ inch to 4 inches. Also, the distance between the tool pivot point and the distal end of the bendable section is preferably equal to or less than the length of the bendable section.

Referring to FIG. 49, an example of a flexible instrument 2000 is shown in use in a stomach 2002 of a patient. The instrument 2000 includes an elongated portion 2004, which itself is flexible, and an articulated bendable section 2006. Any embodiments of the tool 18 described can be mounted at the terminal end of the bendable section 2006. The bendable section 2006 can be any one of the different embodiments described earlier such as those shown in FIGS. 5, 14, 21, or 41. In operation, the flexible instrument 2000 is inserted through a body lumen such as the esophagus 2008, and the tool 18 is directed to the operative site 2009. As shown, the instrument 2000 can lean against some element of the anatomy such as a wall 2010 of the stomach to brace the instrument during the medical procedure, while the bendable section 2006 and the tool 18 are articulated as described above.

Figure 50A:
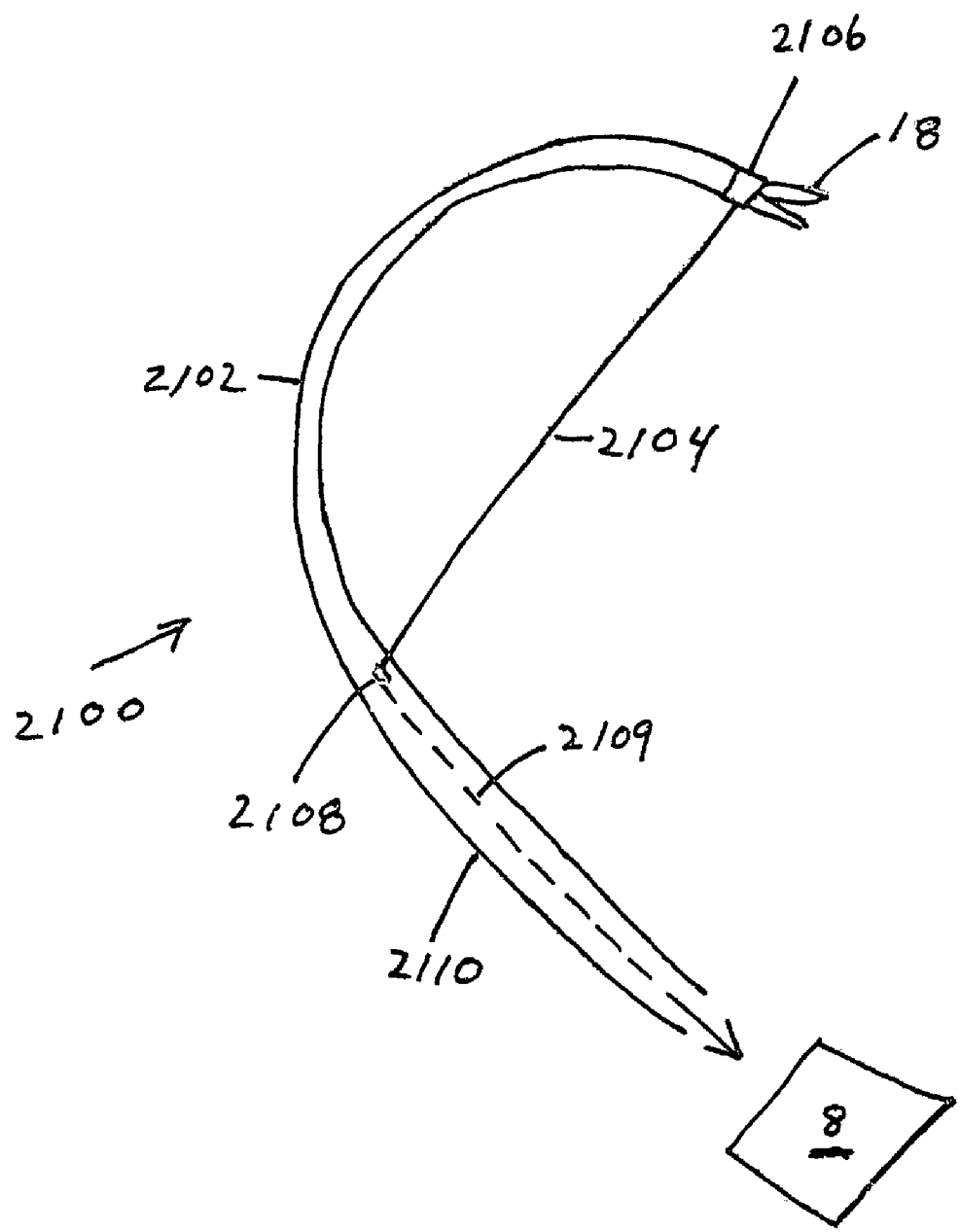
FIG. 50A is a schematic of a flexible instrument with a pull-type cable to operate the end of the instrument in accordance with the invention.

In certain implementations, as shown in FIG. 50A, a flexible instrument 2100 may include a bendable section 2102 that can be operated with one or more pull cables 2104 to manipulate the tip 2106 of the bendable section. The tip 2106 may be provided with an embodiment of the tool 18 described above that is positioned at the operative site to perform a medical procedure. At least one cable 2104 is attached at or near the tip 2106 of the bendable section 2102, and extends from its point of attachment through an aperture 2108 at a position spaced a selected distance along the length of the bendable section 2102 away from the distal end. The remainder of the cable 2109 extends from the aperture 2108 through a shaft 2110 of the instrument 2100 and is coupled, for example, to a drive unit 8, like that described earlier, that applies a tension to the cable 2104 to controllably bend the bendable section 2102.

Figure 50B:
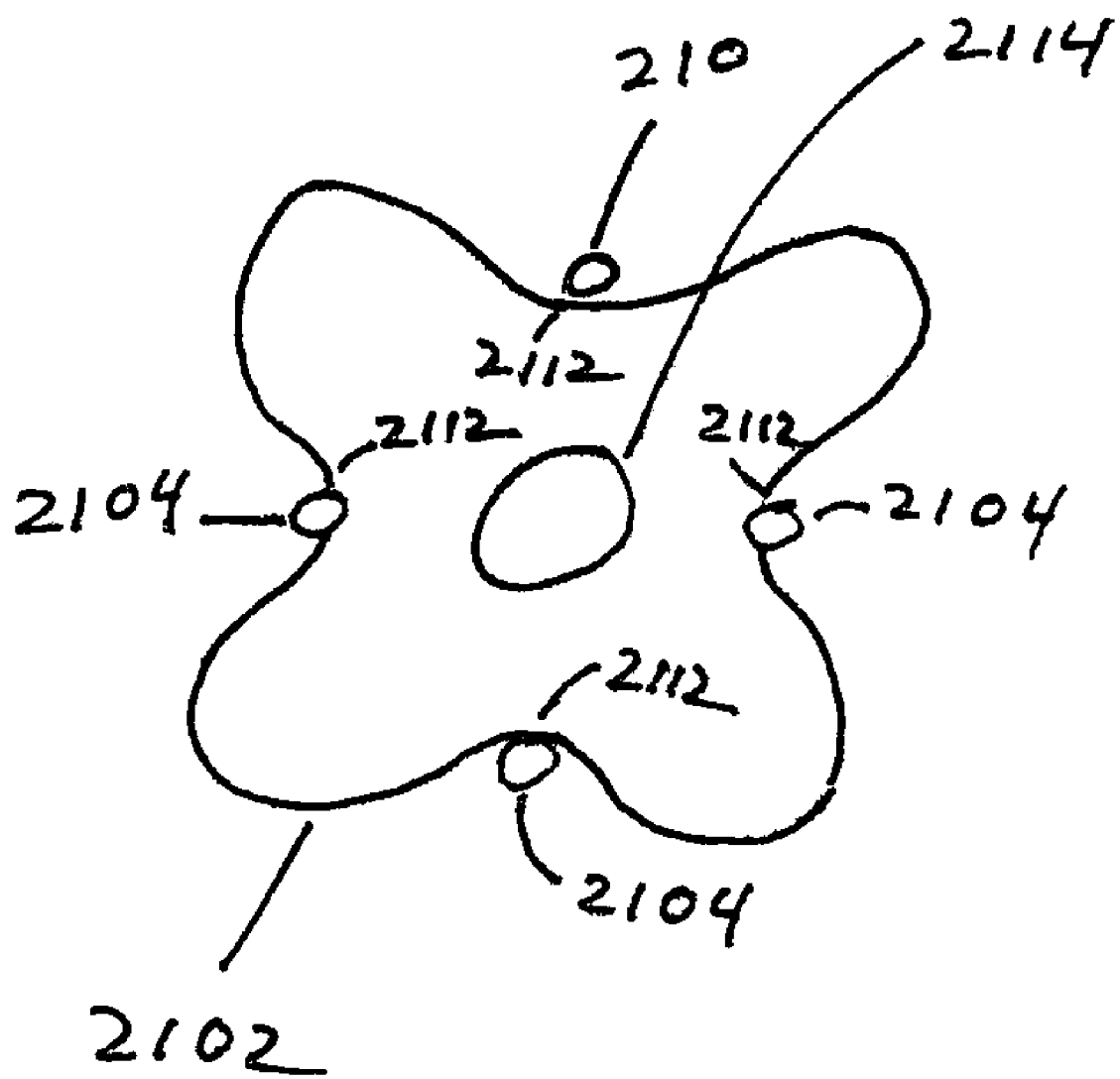
FIG. 50B is cross-sectional view of a bendable section of the flexible instrument of FIG. 50A in accordance with the invention.

The bendable section 2102 may have a circular cross section, or in some embodiments, the bendable section is provided with one or more grooves or valleys 2112 (FIG. 50B) along its length. As such, while the instrument 2100 is inserted into the patient, the cables 2104 lie along the grooves 2112, which prevents the cables 2104 from inadvertently catching any body element. As appropriate tension is applied to a particular cable, it effectively "pops" out of the groove 2112 as the tip of the bendable section 2102 is pulled towards the aperture 2108. For certain embodiments of the tool 18, the bendable section 2102 is provided with a center tube 2114 through which the actuation element for the tool 18 extends.

Figure 51A:
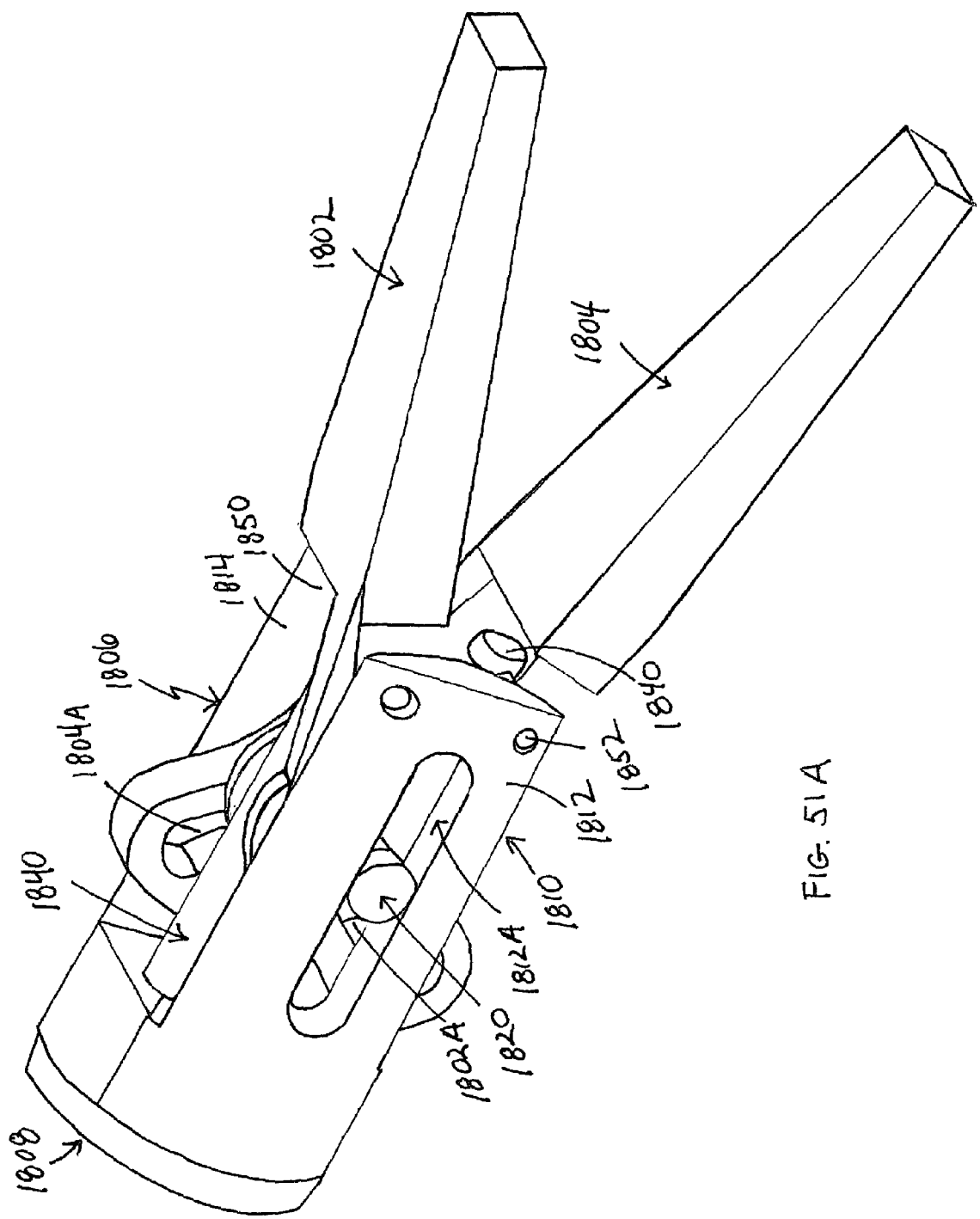
FIG. 51A is a top perspective view of another embodiment of the invention with the end effector in a partially open position.
Figure 51B:
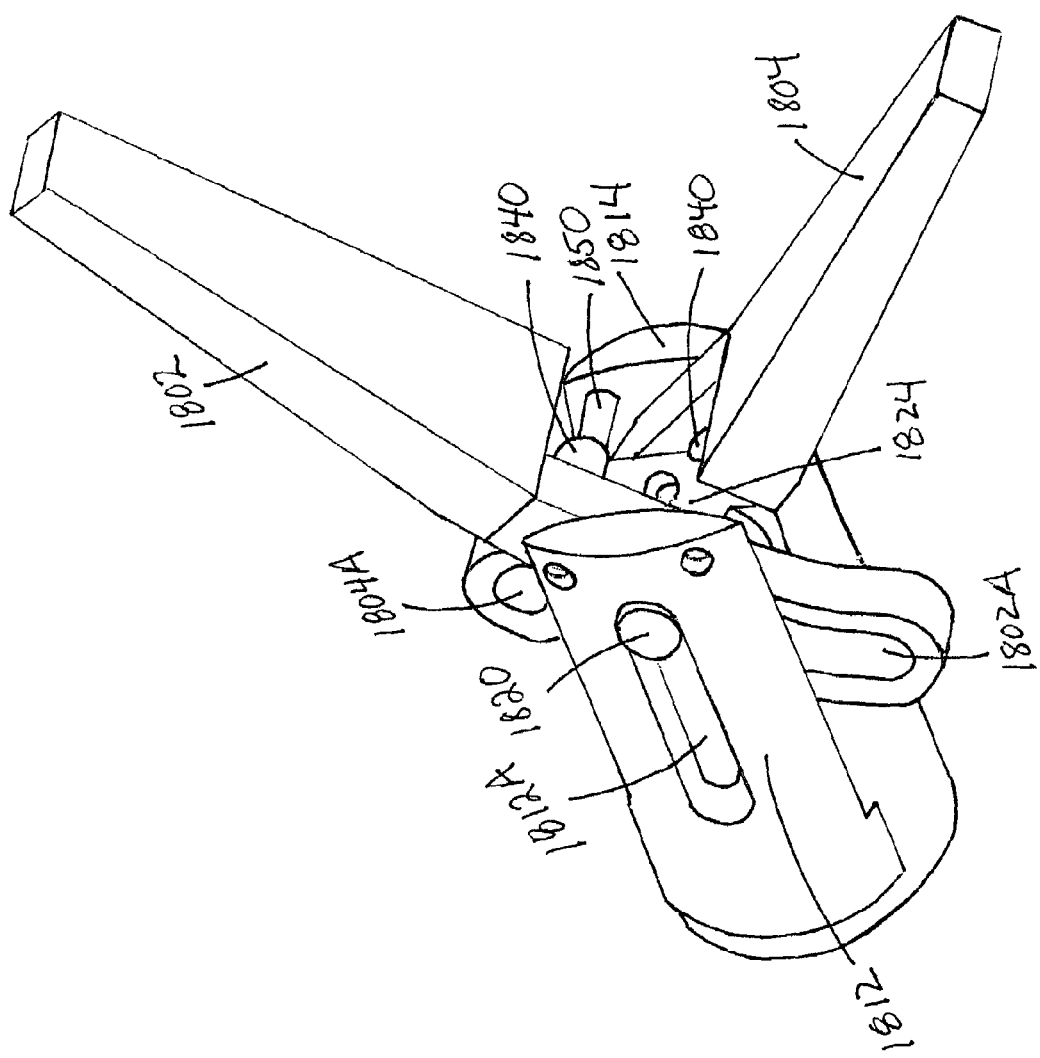
FIG. 51B is a bottom perspective view of the embodiment of FIG. 51A with the tool in a more open position.
Figure 51C:
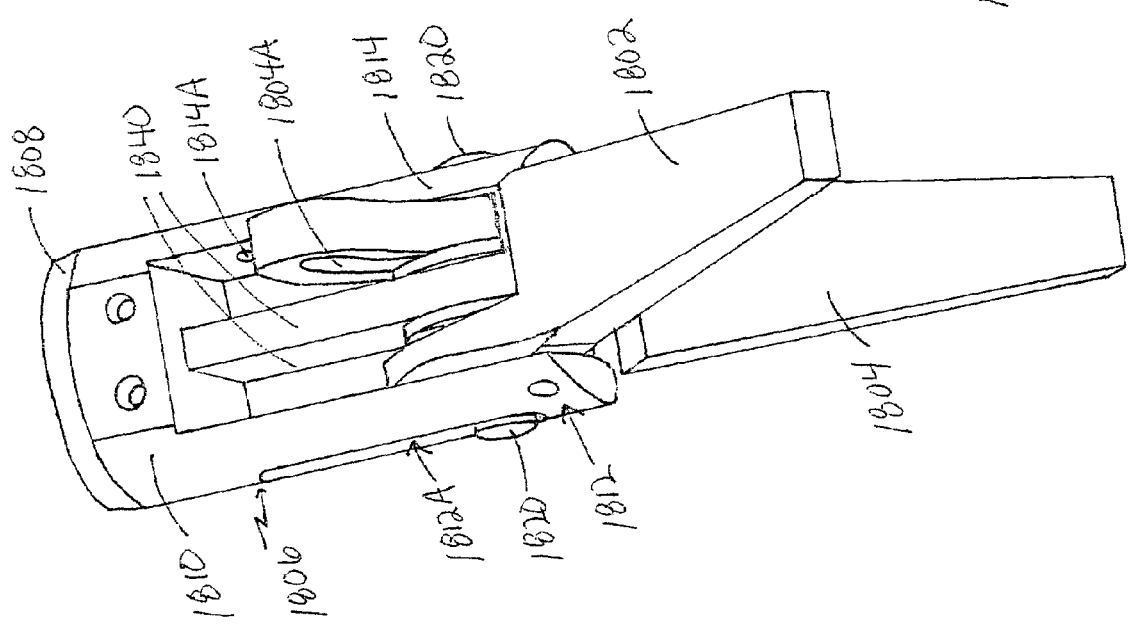
FIG. 51C is a top perspective view of the embodiment of FIG. 51A showing further details.
Figure 51E:
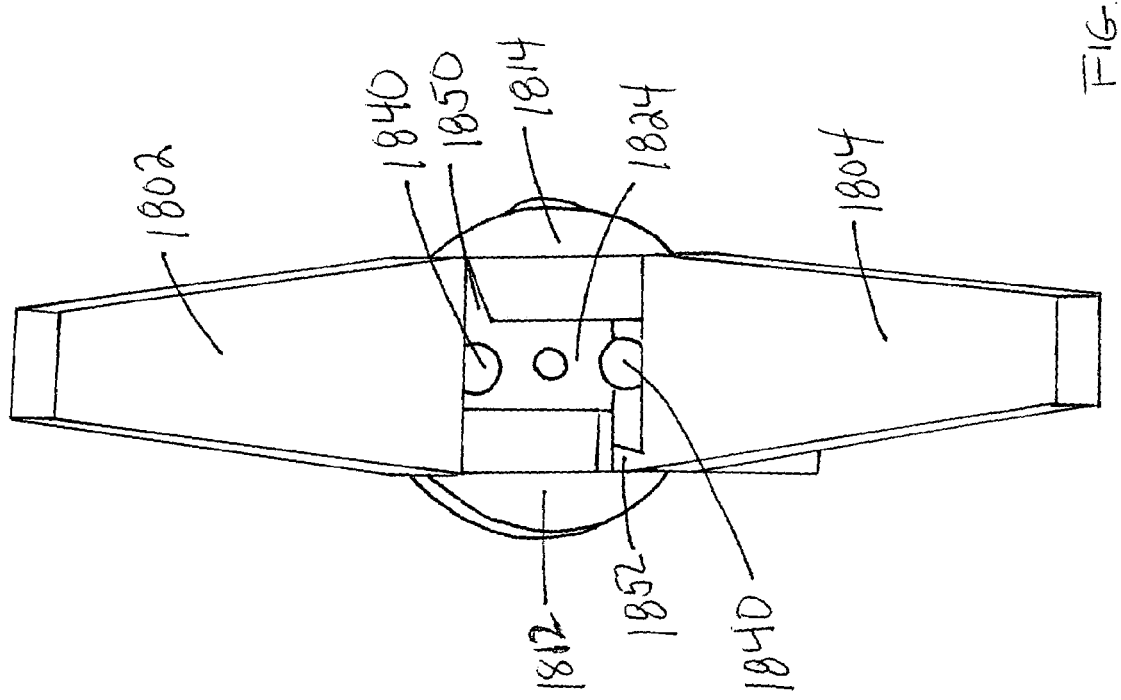
FIG. 51E is a front view of the embodiment of FIG. 51A with the jaws open.

Reference is now made to a further embodiment of the present invention shown in FIGS. 51A through 51E and illustrating a set of jaws that are adapted for operation from a single cable similar to the operation in the arrangement of FIGS. 41-47. The end effector construction in this further embodiment may be considered a blunt dissector. One form or shape of jaw is depicted, however, it is understood that other forms and shapes may also be used. This embodiment employs a slot arrangement in both a base, as well as in the jaws themselves, and provides enhanced gripping action with the use of these slots, in combination with, a transitioning slide member carried between flanges of the base of the instrument tool. Refer to FIGS. 51A through 51E. FIG. 51A is a top perspective view with the end effector in a partially open position, FIG. 51B is a bottom perspective view with the tool in a more open position, FIG. 51C is a top perspective showing further details, FIG. 51D illustrates the slide member part of the overall end effector, and lastly, FIG. 51E is a front view with the jaws open.

The end effector construction shown in FIGS. 51A through 51E includes a pair of jaws 1802 and 1804 supported from a two-piece base 1806. One part of the base is the end piece 1808, and the other part is the base piece 1810. The pieces 1808 and 1810 may also be formed as a single piece. The base piece 1810 has spaced legs 1812 and 1814 that each have the same respective elongated slots 1812A and 1814A. Each of the jaws 1802 and 1804 also has at their base ends slots 1802A and 1804A. A pin 1820 is shown, for example in FIG. 51A, extending through all of the slots 1802A, 1804A, 1812A, and 1814A. The pin 1820 is carried by the slide member 1824 shown in an enlarged perspective view in FIG. 51D. Alternatively, two aligned pins may be used one on either side of the base piece 1810 secured from the slide member 1824.

Referring now to FIG. 51D, the slide member 1824 is a single piece structure having opposite guide channels 1826 and 1828, and also has a transverse passage 1830 for receiving the pin 1820. The slide member 1824 also had a flat front face 1834 that faces the jaws and has a rear passage 1832 to which a cable is secured for moving the slide member and, in turn, actuating the jaws. This cable may be secured to the slide member by being welded thereto or by other appropriate means of attachment. The slide member 1824 is primarily supported by the longitudinally extending rods or rails 1840 that are adapted to engage with the guide channels 1826 and 1828 of the slide member 1824 for translational movement of the slide member 1824. FIG. 51C shows the proximal ends of the rods 1840 supported at the base piece 1810. The distal ends of the rods 1840 are supported from transverse support pins 1850 and 1852, as illustrated in FIGS. 51A, 51B and 51E. Each of the support pins extends between the legs 1812 and 1814 of the base piece 1810. Thus, the rods 1840, as well as the support pins 1850 and 1852 are fixed in position while the slide member 1824 is guided along the rods or rails 1840. The pin 1820 that pass through the slide member 1824 is guided by the slots 1812A and 1812B.

Because the blunt dissector is meant to be used in handling tissue, it is desired that the jaws be arranged so that there is sufficient grasping force even when the jaws are not fully closed (partially open). This is brought about to a great extent by supporting the jaws separately. In this regard the pins 1850 and 1852 form the pivot for the respective jaws 1802 and 1804. From FIGS. 51B and 51E it can be readily seen that these pivot points are separated and are symmetric about the pin 1820 or slot 1812A (1814A). This placement of the pivots, along with the provision of curved slots 1802A and 1802B provide a mechanical advantage, particularly when the jaws are grasping an item but are not fully closed in doing that. Also, by supporting the jaws in this manner, with the offset pivots, the jaws are maintained in a more parallel arrangement over a wider grasping range. Furthermore, increased grasping occurs by virtue of the separated pivots, particularly at or near the fully closed position. It is at that position that the jaws are somewhat inwardly directed to enhance the gripping action.

FIG. 51A shows the jaws partially closed. In that position it is noted that the pin 1820 is about midway in the slot 1802A. When the jaws are fully closed this corresponds to a position of the pin 1820 at its most proximal position relative to the jaws. FIG. 51B shows the jaws in a fully open position with the pin 1820 at the distal end of the slot 1812A. It is noted that the slots 1802A and 1804A are curved in shape and may have a short straight section close to the jaws themselves. This curvature of the slots in the respective jaws enhances the gripping action provided, particularly upon closure of the jaws.

Reference is also now made to another alternate version to that described in FIGS. 51A through 51E. See FIGS. 52A, 52B, and 52C. In this version this may be considered as a needle driver. The jaws depicted may be of other shapes and sizes than those illustrated and usually have tapered ends for grasping a needle. This embodiment uses many of the same or similar components to that already described in FIGS. 51A through 51E. The main difference is that in this embodiment the base piece, identified in FIG. 52A at 1910 extends to form one of the jaws 1912. This jaw is not pivotal, however, the other jaw 1914 is. See FIG. 52A for a perspective view of the end effector, see FIG. 52B for a perspective view of the jaw 1914, and see FIG. 52C for a perspective view of the base with its extending jaw. The jaw 1914 also includes pivot legs 1920 and 1922. These legs are separated, as illustrated, and each have a corresponding curved slot 1920A and 1922A. These legs also include pivot holes 1920B and 1922B for receiving a pivot pin 1930. As illustrated in FIG. 52C, the pin 1930 also extends through holes in the sides 1932 and 1934 of the base piece 1910. The base piece 1910 also has, in the sides 1932 and 1934, elongated slots 1932A and 1934A arranged in a manner similar to the base slots in the earlier version of FIGS. 51A through 51E.

Figure 52A:
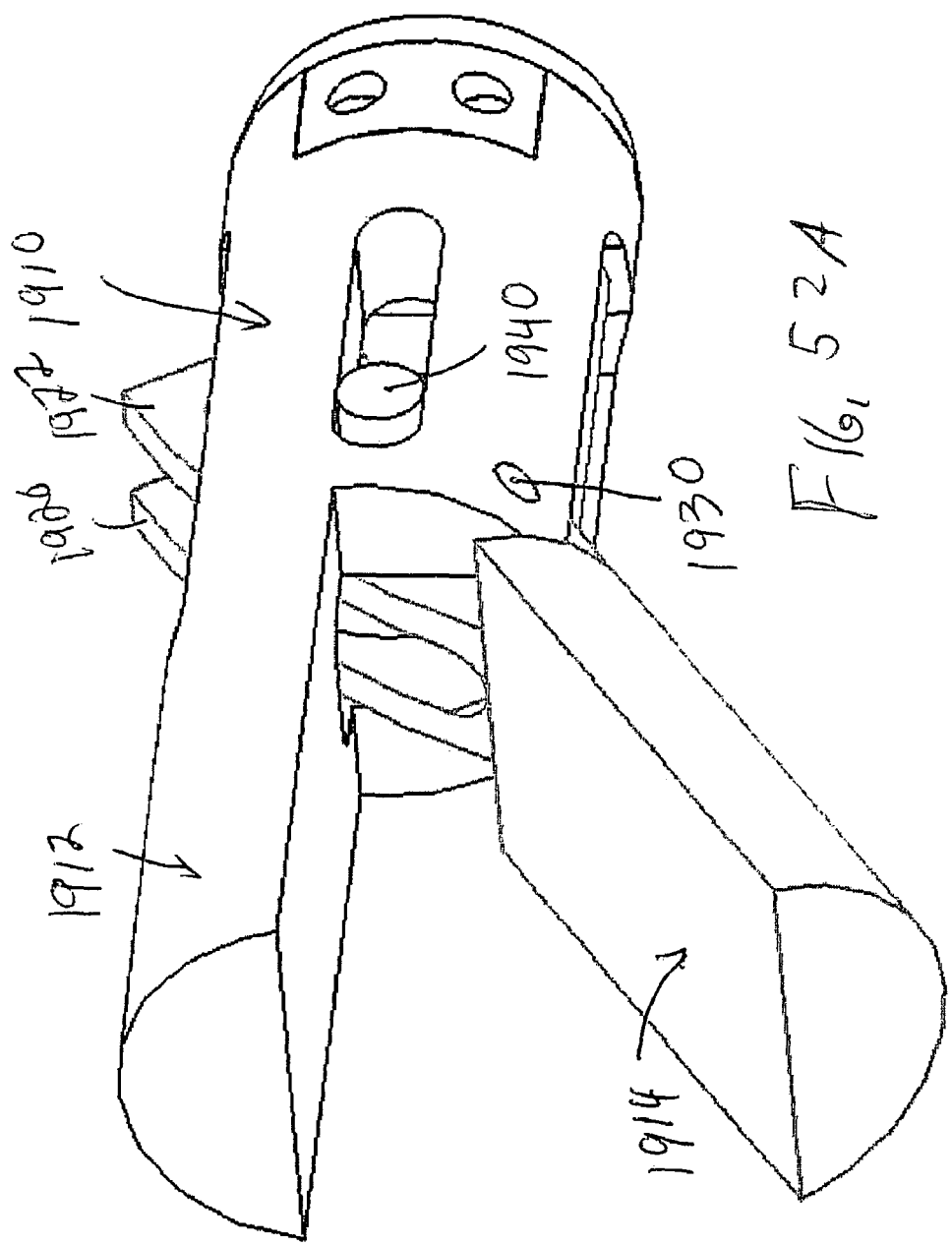
FIG. 52A is a perspective view of still another embodiment of an end effector construction.
Figure 52C:
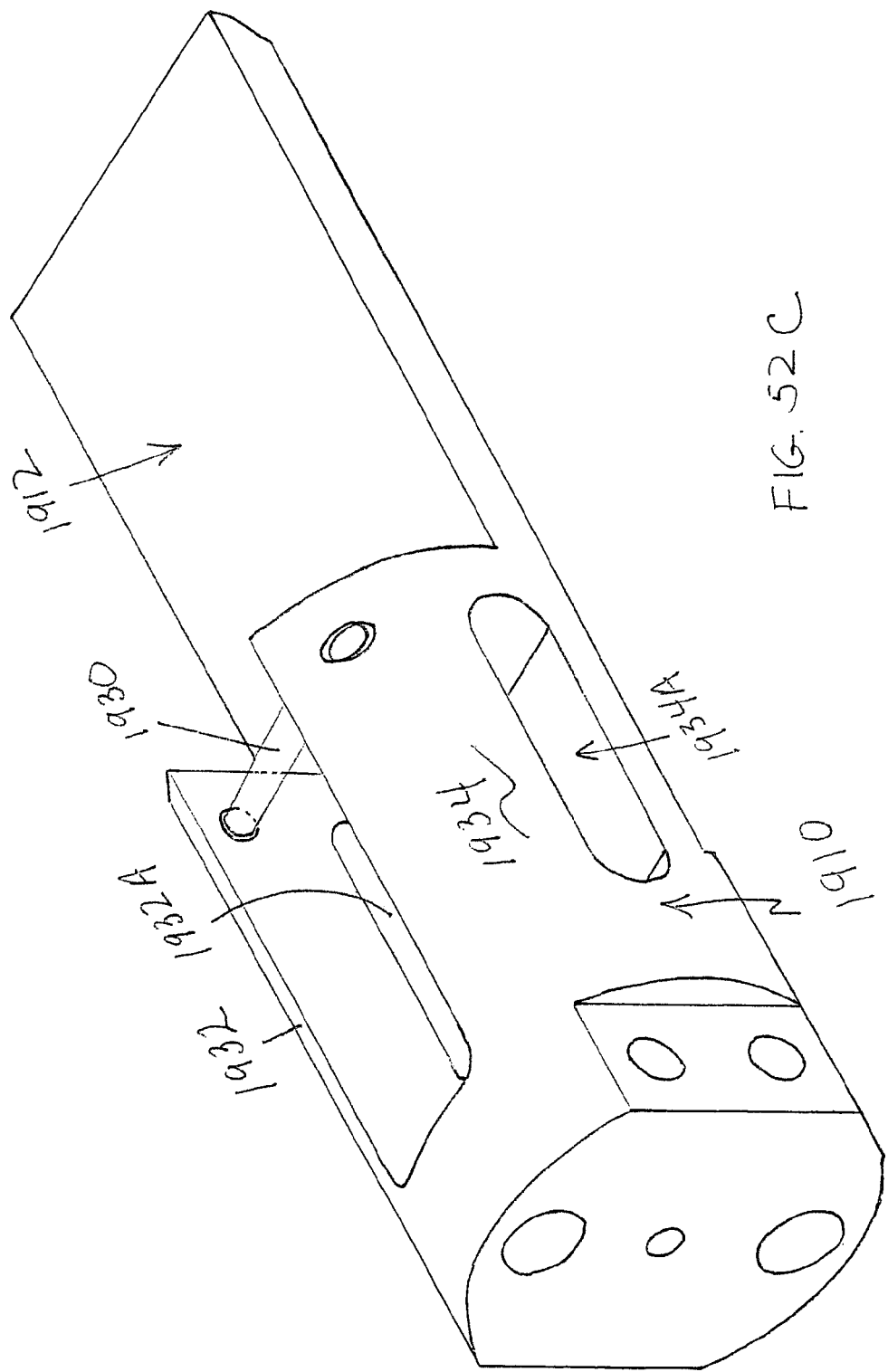
FIG. 52C is a perspective view of the embodiment of FIG. 52A showing the base with its extending jaw.

FIG. 52A also shows the sliding pin 1940 that functions similarly to the pin 1820 of FIG. 51A. Also included in the mechanism of FIGS. 52A through 52C is a slide member that may be substantially identical to the slide member 1824 depicted in FIG. 51D. A pair of rods or rails may be used to support this slide member in the same manner as depicted previously in FIGS. 51A through 51E. Accordingly, a cable is used in this embodiment also to control the movement of the slide member that, in turn, controls the transitioning of the pin 1940 in the base slots. Because the pin also passes through the slots in the jaws, this movement of the pin in the slots also causes a pivoting of the jaw 1914 between open and closed positions thereof.

FIG. 52A shows the jaws fully open with the pin 1940 at its most distal position. As the slide member is actuated the pin 1940 moves to the right causing the jaw 1914 to close against the jaw 1912. Enhanced gripping occurs by virtue of the pivot pin 1930 being displaced away from the centerline of the base piece. This provides improved gripping, particularly of larger diameter items such as a needle.

While this invention has been particularly shown and described with references to preferred embodiments thereof, it will be understood by those skilled in the art that various changes in form and details may be made therein without departing from the scope of the invention encompassed by the appended claims. For example, mention has been made of the bi-axial bending of the bendable section of the instrument. However, the principles of the present invention may also apply to a bendable section that has only one degree-of-freedom, in which case the bendable section would only be controlled by one set of control cables rather than the two sets described earlier.

Figure 53A:
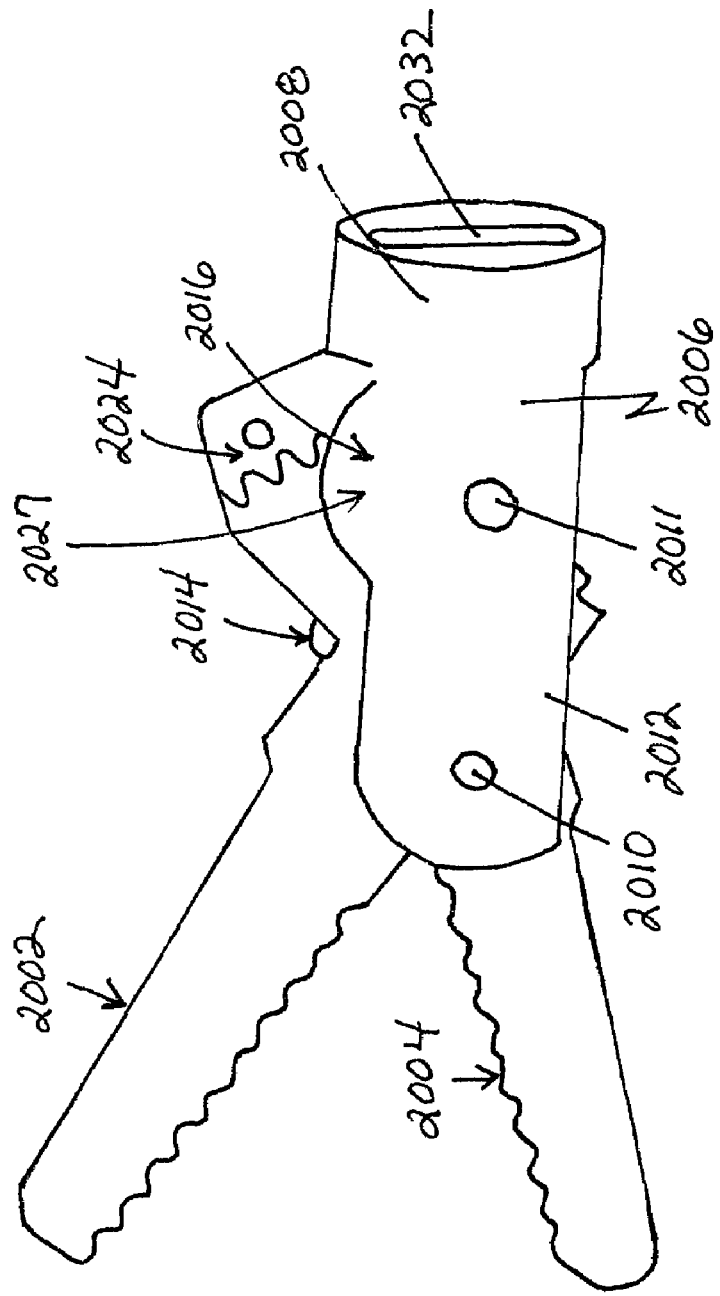
FIG. 53A is a perspective view of another embodiment of the invention with the end effector in an open position.
Figure 53B:
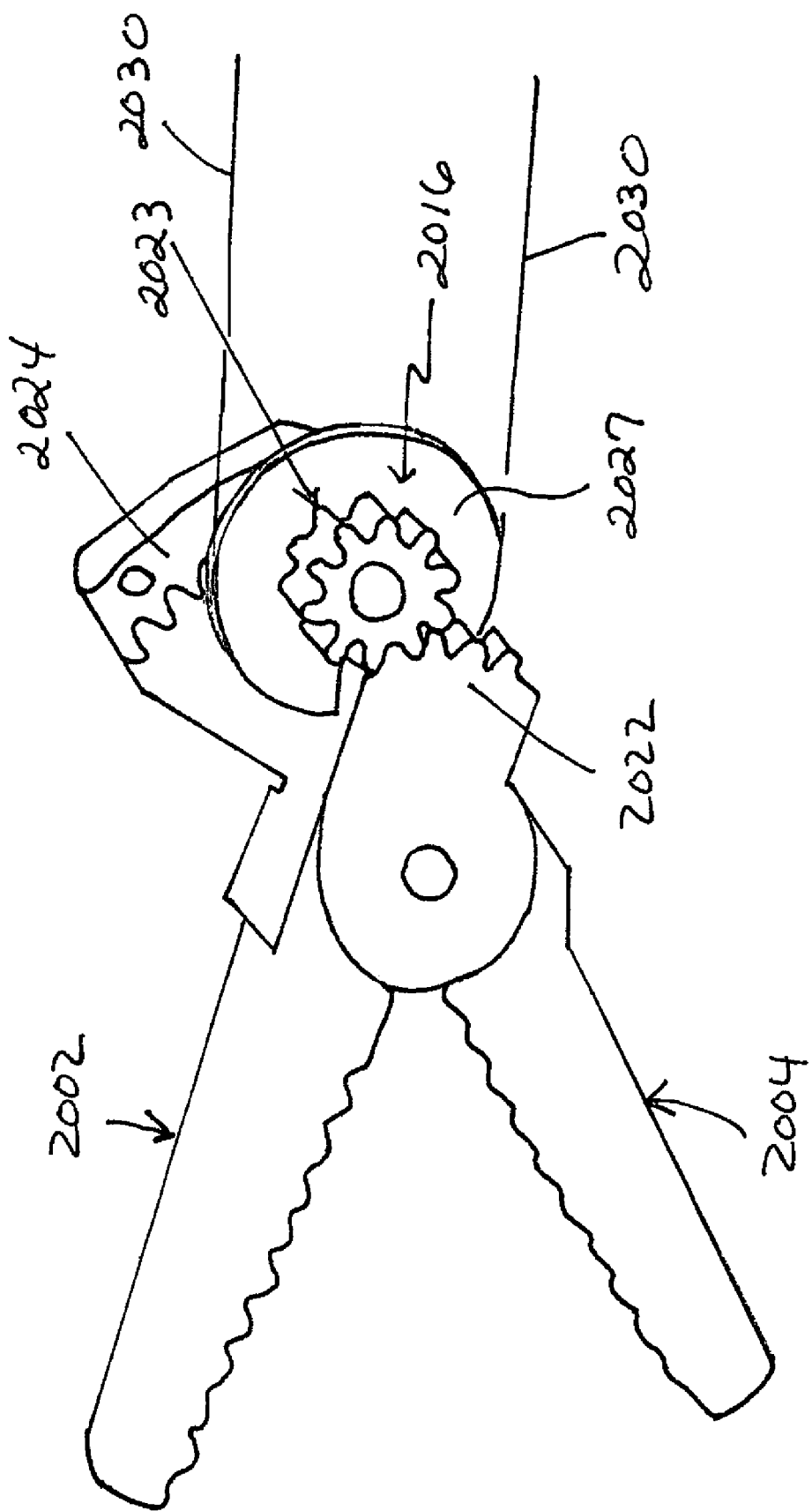
FIG. 53B is a perspective view with the tool in the same position as in FIG. 53A but with part of the structure removed to illustrate the internal structure of the end effector.
Figure 53C:
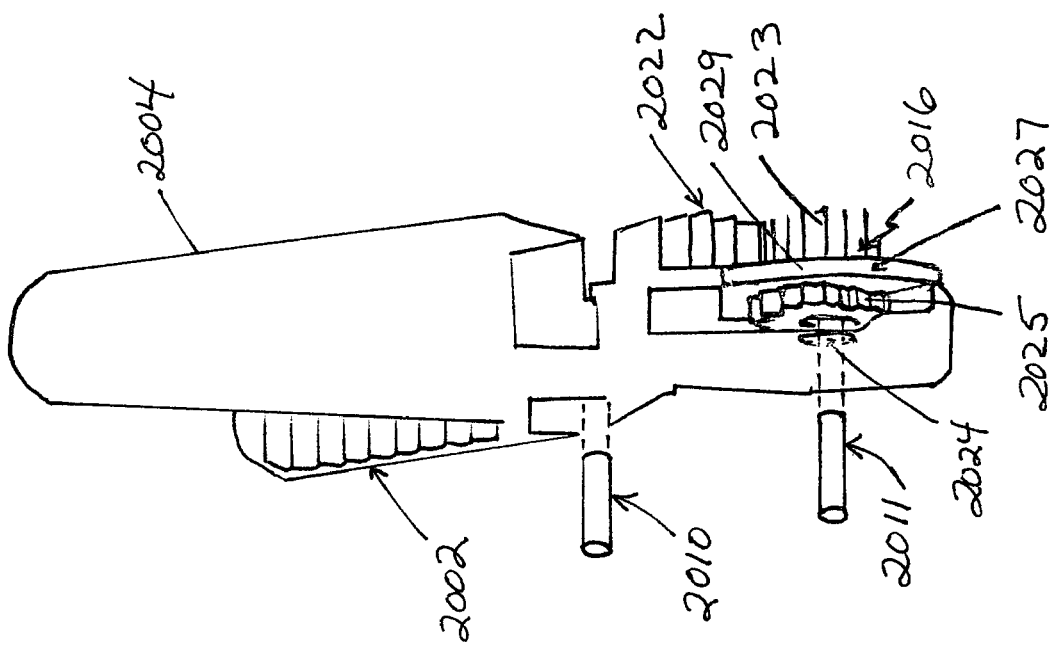
FIG. 53C is an end perspective view of the embodiment of FIGS. 53A and 53B showing further details.

Reference is now made to a further embodiment of the present invention shown in FIGS. 53A through 53C and illustrating a set of jaws that are adapted for operation from a cable arrangement that is termed a pull-pull cable set-up. The end effector construction in this further embodiment may be considered a blunt dissector. One form or shape of jaw is depicted, however, it is understood that other forms and shapes may also be used. This embodiment employs a gear arrangement for the transfer of force from the cable arrangement. Refer to FIGS. 53A through 53C. FIG. 53A is a perspective view with the end effector in an open position; FIG. 53B is a perspective view with the tool in the same position as in FIG. 53A but with part of the structure removed to illustrate the internal structure of the end effector; and FIG. 53C is an end perspective view showing further details.

The end effector construction shown in FIGS. 53A through 53C includes a pair of jaws 2002 and 2004 supported from a base 2006. One part of the base is the end piece 2008. The end piece 2008 has, extending therefrom, spaced legs 2012 and 2014 that each have passages for receiving the pivot pins 2010, 2011. The pin 2010 forms the basic pivot point between the jaws 2002 and 2004. The pin 2011 forms a second pivot point of the end effector, and is basically the pivot point for the gear member 2016 which interacts with the jaws. The gear member 2016 is disposed between the spaced apart legs 2012 and 2014, and engages between the respective jaws.

As illustrated in FIGS. 53A and 53B, each of the jaws has at its proximal end a gear rack adapted for engagement with the gear member 2016. FIGS. 53B and 53C show the gear rack 2022 associated with the jaw 2002. This gear rack is illustrated as having four teeth, but can have fewer or greater numbers of teeth. The gear rack 2022, as illustrated in FIG. 53B, engages with one of the gears of the gear member 2016, namely gear 2023. FIGS. 53A-53C show the gear rack 2024 associated with the jaw 2004. This gear rack may have six teeth, but also can have fewer or greater numbers of teeth. The gear rack 2024, as illustrated in FIG. 53C, engages with one of the gears of the gear member 2016, namely gear 2025. As noted from FIG. 53B, the gear racks are arranged so that the rack 2022 engages on the front side of the gear member 2016, while the gear rack 2024 engages on the rear side of the gear member 2016.

The gear member 2016 is supported by the pin 2011 between the base legs 2012 and 2014. This gear member 2016 has center plate 2027 that supports on either side thereof the gears 2023 and 2025. This is clearly illustrated in FIG. 53C. The gear 2023 is shown as somewhat thicker than the gear 2025, however, these gears may be of various different thickness and in different ratios of thickness. The gears 2023 and 2025 may also have different numbers of teeth but generally have a greater number of teeth than their corresponding respective engageable gear racks 2022 and 2024. The center plate 2027 is shown of larger diameter than the gears 2023 and 2025 and receives the cable 2030 which is attached to the plate member 2027. This attachment may be by securing in some manner such as by crimping or being retained in a hole or passage in the plate member 2027. The cable 2030 may be a single piece or multiple piece cable and is pulled in opposite directions to actuate (rotate) the plate member 2027 and thus operate the jaws. The plate member 2027 may have a peripheral slot 2029, as illustrated in FIG. 53C, about its diameter to hold the cable in place in the plate member 2027.

The particular jaw construction shown in FIGS. 53A-53C is characterized by improved grasping force, particularly upon full closure of the jaws. The cable may be connected to a pulley or the like at a more proximal end of the instrument shaft to which the end effector is attached. Also, proximal of the end effector one may provide a wrist mechanism or a remote controllable bendable section or sections to provide additional degrees of freedom of operation to the end effector. The gear arrangement described herein enables the transmission of a force via the cable to the gripping portion of the jaws with an improved ratio of applied force transmission. That is, the jaws have a good transmission ratio of the force applied to the cable relative to the force applied at the jaws to an object being held and manipulated. The embodiment in FIGS. 53A-53C also provides a maximum force transmission as the jaws are approaching a closed position.

In the embodiment described in FIGS. 53A-53C it is noted that it has been determined that there are certain dimensional considerations that have been found important in providing the desired force transmission. These parameters relate to such dimensions as the distance between the two pivot points, as represented by pins 2010 and 2011; the diameters of the gears and size of the related gear racks; the length of the jaws; and the desired full open dimension of the jaws. For a further analysis of the transmitted forces refer to the schematic jaw diagrams illustrated in FIGS. 54A and 54B. FIG. 54A shows the jaws in a closed position while FIG. 54B shows the jaws in a full open position.

In accordance with one embodiment of the invention the gear arrangement is constructed to fit within a 5 mm guide shaft when closed. Also, the jaws may have a desired full open position of 0.600". The input force is designated as $F_D$ while the jaw force is designated as $F_E$. The radii of the respective gear racks are designated as $r_{J1}$ and $r_{J2}$. The radii at the gear member 2016 are designated as $r_1$ and $r_D$. The length of each jaw is the same as measured from its pivot point and is designated as E. Based upon the foregoing parameters, as illustrated in FIGS. 54A and 54B, the following equations apply:

$$r_D F_D = r_1 F_1$$

$$F_1 = F_{J1}$$

$$r_{J1} F_{J1} = E F_E$$

$$r_{J1} (r_D/r_1) F_D = E F_E, \text{ thus}$$

$$F_E = (r_{J1}/E)(r_D/r_1) F_D$$

The jaw length E=0.6"

$r_D$=0.090", thus $$F_E = 0.15(r_{J1}/r_1) F_D$$

For $r_1$=0.040" and $r_{J1}$=0.197"

$$F_E = 0.74 F_D$$

From this analysis, and with the dimensions so selected, for say every 10 pounds applied at the cable there is a resultant 7.4 pounds applied at the jaws, thus providing an effective force transfer.

The relationship between the dimensions $r_{J1}$ and $r_{J2}$ is represented as follows:

$$r_{J2} = r_{J1} + 2r_1$$

So $r_{J2}$ is the constraint, not $r_{J1}$

For the above values, $r_{J1}$=0.197−0.08=0.117"

Figure 55A:
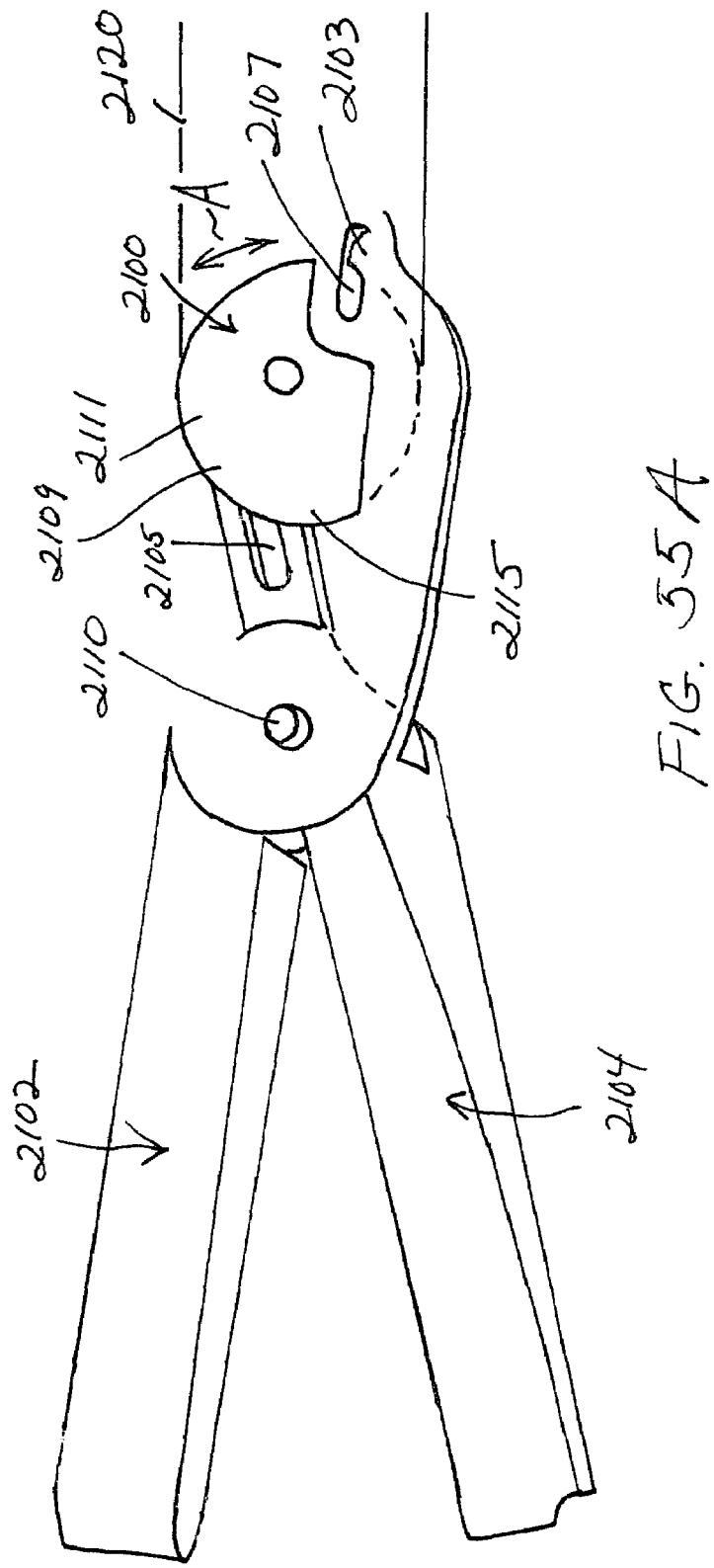
FIG. 55A is a perspective view of still another embodiment of the present invention with the base removed to show the internal mechanism.
Figure 55B:
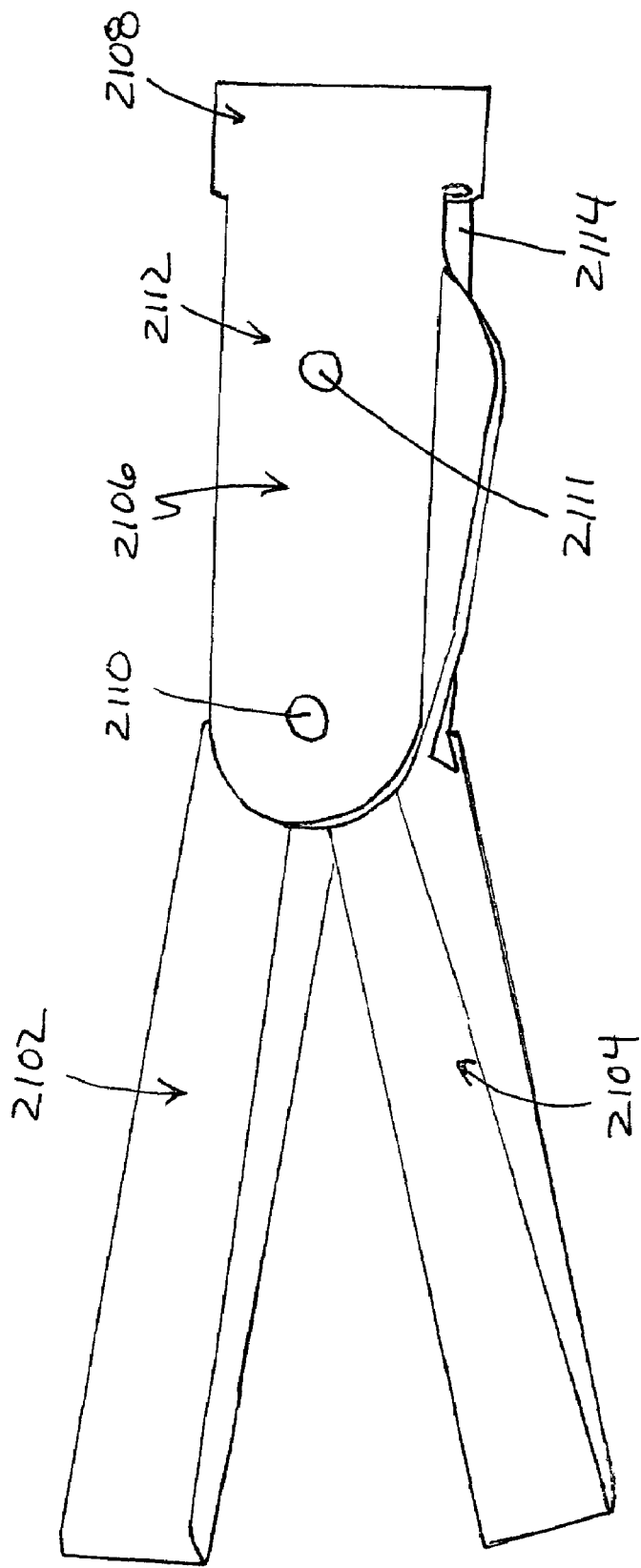
FIG. 55B shows the same perspective view as in FIG. 55A including the supporting base piece.

So for $r_{J2}$, jaw 2, then $F_E$=0.74$F_D$ $r_{J1}$, jaw 1, then $F_E$=0.44 $F_D$ Reference is now also made to FIGS. 55A and 55B for still another embodiment of the invention that employs a control wheel 2100 in place of the gear member of FIGS. 53A, 53B and 53C. FIGS. 55A and 55B illustrate a set of jaws that are adapted for operation from a cable arrangement that is termed a pull-pull cable set-up. This embodiment uses the rotating wheel 2100 for the transfer of motion from the cable arrangement to the jaws. FIG. 55A is a perspective view of this embodiment with the base removed to show the internal mechanism. FIG. 55B shows the same perspective view as in FIG. 55A including the supporting base piece.

The end effector construction shown in FIGS. 55A and 55B includes a pair of jaws 2102 and 2104 supported from a base 2106. One part of the base is the end piece 2108. The end piece 2108 may be provided with a proximal slot like the slot 2032 in FIG. 53A for accommodating a drive cable or tendon. The end piece 2108 has, extending therefrom, spaced legs 2112 and 2114 that each have passages for receiving the pivot pins 2110, 2111. The pin 2110 forms the basic pivot point between the jaws 2102 and 2104. The pin 2111 forms a second pivot point of the end effector, and is basically the pivot point for the rotating wheel 2100 which interacts with and drives the jaws. The control member 2100 is disposed between the spaced apart legs 2012 and 2014, and engages between proximal ends of the respective jaws.

Each of the jaws 2102 and 2104 has a jaw-like distal end as illustrated and also each has a proximal end, as most clearly shown in FIG. 55A, with corresponding actuation slots 2103 (in full solid outline) and 2105 (in partial full and dotted outline). Each of the slots 2103 and 2105 are of elongated shape and receive respective pins 2107 (shown in solid outline) and 2109 (shown in dotted outline) that extend from opposite side surfaces of the control wheel 2100. As the control wheel 2100 rotates the pins 2107 and 2109, sliding in their respective slots 2103 and 2105, cause an opening and closing of the jaws as the pins move in the slots. In FIG. 55A the length of the slots may be illustrated in a somewhat exaggerated manner, but these slots should be at least partially elongated so that the jaws do not bind-up during the transition between open and closed positions.

The control wheel 2100 is supported for rotation by means of the pin 2111 which is, in turn, supported in the base 2106, as is illustrated in FIG. 55B. The control wheel 2100 may have a peripheral slot 2115 like that illustrated in the earlier embodiment of FIGS. 53A-53C. The control wheel 2100 receives the cable 2120 which is attached thereto. This attachment may be by securing in some manner such as by crimping or being retained in a hole or passage in the control wheel 2100. The cable 2120 may be a single piece or multiple piece cable and is pulled in opposite directions to actuate (rotate) the control wheel 2100 and thus operate the jaws. The peripheral slot 2115 in the control wheel 2100 extends about its diameter to hold the cable in place in the control wheel 2100.

In FIG. 55A the double-headed arrow A illustrates the rotation of the control wheel 2100. In FIG. 55A the jaws may be considered as moving toward a closed position, in which case the control wheel 2100 is controlled via the cable or tendon 2120 to rotate counterclockwise. On the other hand, rotation of the control wheel 2100 in the opposite clockwise direction causes the jaws to open. The closing force is a function of positions of the pins 2107 and 2109. As the control wheel 2100 is rotated toward the full closed position, the pins 2107 and 2109 become aligned with a straight line connecting the support pins 2110 and 2111. This is a position of maximum force transfer from the control wheel to the jaws.

This invention can be implemented and combined with other applications, systems, and apparatuses, for example, those discussed in greater detail in U.S. Provisional Application No. 60/332,287, filed Nov. 21, 2001, the entire contents of which are incorporated herein by reference, as well as those discussed in greater detail in each of the following documents, all of which are incorporated herein by reference in their entirety:

U.S. Provisional Application Nos. 60/344,124 filed Dec. 21, 2001 and 60/382,532 filed May 22, 2002, continuation-in-part of U.S. application Ser. Nos. 10/014,143, 10/008,964, 10/013,046, 10/011,450, 10/008,457, 10/008,871, and 10/012,845 all filed Nov. 16, 2001, each of which claim the benefit of U.S. Provisional Application No. 60/279,087 filed Mar. 27, 2001, continuation-in-part of U.S. application Ser. No. 09/827,643 filed Apr. 6, 2001, which claims the benefit of U.S. Provisional Application Nos. 60/257,869 filed Dec. 21, 2000 and 60/195,264 filed Apr. 7, 2000, U.S. Pat. Nos. 6,197,017, 6,432,112 and 6,554,844, PCT application Serial No. PCT/US00/12553 filed May 9, 2000, U.S. application Ser. Nos. 10/023,024, 10/011,371, 10/011,449, 10/010,150, 10/022,038, and 10/012,586, all filed Nov. 16, 2001, and U.S. application Ser. Nos. 10/034,871 filed Dec. 21, 2001, Ser. No. 10/270,741 filed Oct. 11, 2002, Ser. No. 10/270,743 filed Oct. 11, 2002, Ser. No. 10/270,740 filed Oct. 11, 2002, Ser. No. 10/077,233 filed Feb. 15, 2002, Ser. No. 10/097,923 filed Mar. 15, 2002, Ser. No. 09/783,637 filed Feb. 14, 2001, Ser.

No. 10/299,588 filed Nov. 18, 2002 which, in turn, claims priority to Provisional Application No. 60/332,287 filed Nov. 21, 2001; Provisional Application No. 60/344,124 filed Dec. 21, 2001; and Provisional Application No. 60/382,532 filed May 22, 2002, Ser. No. 10/302,804 filed Nov. 21, 2002, and Ser. No. 10/639,785 filed Aug. 12, 2003.

While this invention has been particularly shown and described with references to preferred embodiments thereof, it will be understood by those skilled in the art that various changes in form and details may be made therein without departing from the scope of the invention encompassed by the appended claims.

What is claimed is:

1. A robotically controlled medical instrument comprising:
    a first jaw;
    a second jaw;
    a drive mechanism including a linkage having a first end connected by a pivot joint to the first jaw and a second end provided with a pin positioned in a slot of the second jaw, the linkage providing increasing leverage to increase the force applied to an item grasped between the first and second jaws as the pin moves along the slot; and
    an electronic controller that controls the operation of the drive mechanism.

2. The medical instrument of claim 1 wherein the slot has a curved segment and a straight segment.

3. The medical instrument of claim 1 wherein the drive mechanism includes a rotation piece connected to the first and second jaws by a second pivot joint, and a second linkage having a first end connected to the first linkage by the pin and a second end provided with a second pin positioned in the slot, rotation of the rotation piece causing a consequent rotation of the first jaw with respect to the second jaw, the first and second pins moving along the slot as the rotation piece rotates.

4. The medical instrument of claim 3 wherein the rotation piece is connected to a first drive cable, and the second jaw is connected to a second drive cable, respective tension being applied to the first and second drive cables to operate one or both of the first and second jaws.

5. The medical instrument of claim 4 further comprising a shaft, the first and second jaws being supported at the distal end of the shaft, and the first and second drive cables extending through the shaft.

6. The medical instrument of claim 1 further comprising an accommodating mechanism that allows continued movement of the drive mechanism towards a locked position even after the first and second jaws contact a larger item so that the drive mechanism can move to the locked position when grasping items of different sizes.

7. The medical instrument of claim 6 wherein the accommodating mechanism is an extended end segment of the slot extending from the straight segment, the pin residing in the end segment when the first and second jaws grasp an item, the extent to which being dependent upon the size of the item being grasped.

8. The medical instrument of claim 6 wherein the accommodating mechanism is a compliance member.

9. The medical instrument of claim 8 wherein the compliance member is resilient member interposed between the linkage and the first jaw, the resilient member being compressed when the first and second jaws grasp an item, the extent of the compression of the resilient member being dependent on the size of the item being grasped.

10. The medical instrument of claim 8 wherein the compliance member is a hinge in one of the first and second jaws about which the respective jaw flexes, the amount of flexing being dependent upon the size of an item being grasped.

11. The medical instrument of claim 10 wherein the hinge is located below the furthest extent of a gap that extends into the respective jaw.

12. A robotically controlled medical instrument comprising:
    a first jaw;
    a second jaw;
    a drive mechanism which increases the force applied to an item grasped between the first and second jaws, the drive mechanism and the first and second jaws being provided with an accommodating mechanism that allows continued movement of the drive mechanism towards a locked position even after the first and second jaws contact a larger item so that the drive mechanism can move to the locked position when grasping items of different sizes, wherein the drive mechanism includes a linkage having a first end connected by a pivot joint to the first jaw and a second end provided with a pin positioned in a slot of the second jaw, the slot having a curved segment, a straight segment extending from the curved segment, and an extended end segment extending from the straight segment, the accommodating mechanism being the end segment, the pin residing in the end segment when the first and second jaws grasp an item, the extent to which being dependent upon the size of the item being grasped; and
    an electronic controller that controls the operation of the drive mechanism.

13. The medical instrument of claim 12 wherein the first jaw is coupled to a first drive cable, and the second jaw is coupled to a second drive cable, respective tension being applied to the first and second drive cables to operate the first and second jaws.

14. The medical instrument of claim 13 wherein the amount of tension being applied to the respective cables is controlled with the electronic controller coupled with a user interface operated by a user.

15. The medical instrument of claim 12 wherein the accommodating mechanism is a compliance member.

16. The medical instrument of claim 15 wherein the drive mechanism increases leverage through the linkage connected to the first jaw by the pivot joint, the compliance member being a resilient member interposed between the linkage and the first jaw, and being compressed when the first and second jaws grasp an item, the extent of the compression of the resilient member being dependent on the size of the item being grasped.

17. The medical instrument of claim 15 wherein the compliance member is a hinge in one of the first and second jaws about which the respective jaw flexes, the amount of flexing being dependent upon the size of an item being grasped.

18. The medical instrument of claim 17 wherein the hinge is located below the furthest extent of a gap that extends into the respective jaw.

19. A robotically controlled medical instrument comprising:
    an instrument shaft having proximal and distal ends;
    a tool supported from the distal end of said instrument shaft and useable in performing a medical procedure on a subject, said tool constructed and arranged so to be capable of receiving different size items and including a pair of work members, a drive mechanism which increases the force applied to an item grasped between the pair of work members, and an accommodating mechanism interacting with said drive mechanism and the pair of work members and that allows the pair of work members to be closed beyond a maximum grasping position so that the pair of work members can grasp items of various sizes;

a rotation piece coupling with one of said pair of work members and a pair of linkages one engaged with the rotating piece, and the other engaged with one of said pair of work members, said pair of linkages also pivotally supported relative to each other;

a robotic controller coupled to said instrument shaft for remotely effecting control of said tool.

20. The medical instrument of claim 19 including at least one drive cable extending via said instrument shaft for operating the rotating piece, and the other for operating the other work member.

21. The medical instrument of claim 19 wherein the accommodating mechanism comprises a compliance member.

22. The medical instrument of claim 21 wherein the drive mechanism increases leverage through a linkage connected to a first work member by a pivot joint, the compliance member being a resilient member interposed between the linkage and the first work member, and being compressed when the first work member and a second work member grasp an item, the extent of the compression of the resilient member being dependent on the size of the item being grasped.

23. The medical instrument of claim 21 wherein the compliance member is a hinge in one of the pair of work members about which the respective work member flexes, the amount of flexing being dependent upon the size of an item being grasped.

24. The medical instrument of claim 19 wherein the force applied by the first and second work members beyond the maximum grasping position is proportional to the size of the item being grasped.

25. A robotically controlled medical instrument comprising:

an instrument shaft having proximal and distal ends;

a tool supported from the distal end of said instrument shaft and useable in performing a medical procedure on a subject; said tool constructed and arranged so to be capable of receiving different size items and including a pair of work members, a drive mechanism which increases the force applied to an item grasped between the pair of work members, and an accommodating mechanism interacting with said drive mechanism and pair of work members and that allows the pair of work members to be closed beyond a maximum grasping position so that the pair of work members can grasp items of various sizes, wherein the drive mechanism includes a linkage having a first end connected by a pivot joint to a first work member and a second end provided with a pin positioned in a slot of a second work member, the slot having a curved segment, a straight segment extending from the curved segment, and an extended end segment extending from the straight segment, the accommodating mechanism being the end segment, the pin residing in the end segment when the first and second work members grasp an item, the extent to which being dependent upon the size of the item being grasped; and a robotic controller coupled to said instrument shaft for remotely effecting control of said tool.

26. A method of grasping an item with a robotically controlled surgical tool comprising:

positioning the item between a first jaw and a second jaw of the tool, wherein the tool includes a drive mechanism, and wherein the drive mechanism includes a linkage having a first end connected by a pivot joint to the first jaw and a second end provided with a pin positioned in a slot of the second jaw, the slot having a curved segment, a straight segment extending from the curved segment, and an extended end segment extending from the straight segment that provides an accommodating mechanism, the pin residing in the end segment when the first and second jaws grasp an item, the extent to which being dependent upon the size of the item being grasped;

moving the first and second jaws to an initial contact position for grasping the item; and increasing leverage to the first and second jaws beyond the initial contact position to increase the force applied to the item grasped between the first and second jaws with the magnitude of applied force being proportional to the size of the item being grasped.

27. The method of claim 26 wherein the applied force is directly proportional to the diameter of the item being grasped.

28. The method of claim 26 wherein the proportional force is applied with the use of a resilient member associated with the first and second jaws.

29. The method of claim 26 wherein the proportional force is applied with the use of at least one of the first and second jaws having a closable gap.

* * * * *